US009206159B2

(12) United States Patent
Long et al.

(10) Patent No.: US 9,206,159 B2
(45) Date of Patent: Dec. 8, 2015

(54) PIPERAZINE-PIPERIDINE COMPOUNDS AS HEPATITIS C VIRUS INHIBITORS

(71) Applicants: Daniel D. Long, San Francisco, CA (US); Robert Murray McKinnell, Millbrae, CA (US); Lori Jean Van Orden, San Francisco, CA (US); Gavin Ogawa, San Francisco, CA (US); Donna Wilton, San Francisco, CA (US)

(72) Inventors: Daniel D. Long, San Francisco, CA (US); Robert Murray McKinnell, Millbrae, CA (US); Lori Jean Van Orden, San Francisco, CA (US); Gavin Ogawa, San Francisco, CA (US); Donna Wilton, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 401 days.

(21) Appl. No.: 13/869,199

(22) Filed: Apr. 24, 2013

(65) Prior Publication Data
US 2013/0287730 A1 Oct. 31, 2013

Related U.S. Application Data

(60) Provisional application No. 61/774,033, filed on Mar. 7, 2013, provisional application No. 61/637,959, filed on Apr. 25, 2012.

(51) Int. Cl.
C07D 401/14 (2006.01)
A61K 31/496 (2006.01)
A61K 31/506 (2006.01)
A61K 31/55 (2006.01)
C07D 487/08 (2006.01)
C07D 405/14 (2006.01)
A61K 45/06 (2006.01)

(52) U.S. Cl.
CPC ............ *C07D 401/14* (2013.01); *A61K 31/496* (2013.01); *A61K 31/506* (2013.01); *A61K 31/55* (2013.01); *A61K 45/06* (2013.01); *C07D 405/14* (2013.01); *C07D 487/08* (2013.01)

(58) Field of Classification Search
CPC ... C07D 401/14; C07D 405/14; C07D 487/08
See application file for complete search history.

(56) References Cited

U.S. PATENT DOCUMENTS

| 7,659,270 | B2 | 2/2010 | Bachand et al. |
| 8,088,368 | B2 | 1/2012 | Guo et al. |
| 8,147,818 | B2 | 4/2012 | Bachand et al. |
| 8,303,944 | B2 | 11/2012 | Bachand et al. |
| 2008/0050336 | A1 | 2/2008 | Bachand et al. |
| 2010/0215618 | A1 | 8/2010 | Carter et al. |
| 2011/0064695 | A1 | 3/2011 | Qiu et al. |
| 2011/0064698 | A1 | 3/2011 | Or et al. |
| 2011/0077280 | A1 | 3/2011 | Bender et al. |
| 2011/0142798 | A1 | 6/2011 | Qiu et al. |
| 2011/0152237 | A1 | 6/2011 | Chen et al. |
| 2011/0223134 | A1 | 9/2011 | Nair et al. |
| 2011/0274648 | A1 | 11/2011 | Lavoie et al. |
| 2011/0286961 | A1 | 11/2011 | Belema et al. |
| 2011/0300104 | A1 | 12/2011 | Qiu et al. |
| 2012/0040977 | A1 | 2/2012 | Li et al. |
| 2012/0114600 | A1 | 5/2012 | McKinnell et al. |
| 2012/0195857 | A1 | 8/2012 | Belema et al. |
| 2013/0028859 | A1 | 1/2013 | Bender et al. |
| 2013/0115194 | A1 | 5/2013 | Long et al. |

FOREIGN PATENT DOCUMENTS

| WO | 2011/079327 A1 | 6/2011 |
| WO | 2011/091446 A1 | 7/2011 |
| WO | 2012/048421 A1 | 4/2012 |

OTHER PUBLICATIONS

International Search Report for PCT/US2013/037920 dated Jun. 13, 2013.

*Primary Examiner* — Samantha Shterengarts
(74) *Attorney, Agent, or Firm* — Jeffrey A. Hagenah; Roberta P. Saxon

(57) ABSTRACT

The invention provides compounds of formula (I):

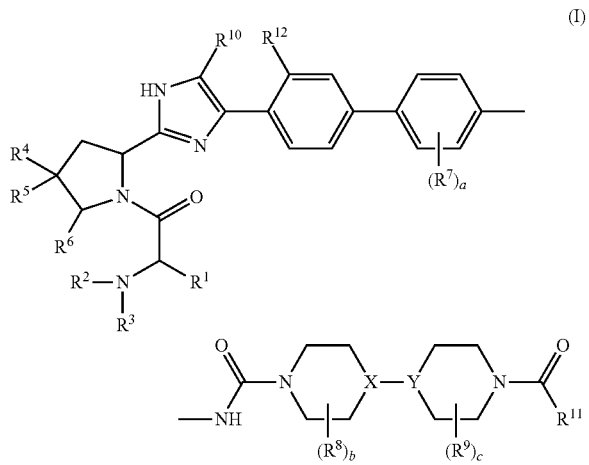

wherein the variables are defined in the specification, or a pharmaceutically-acceptable salt thereof, that are inhibitors of replication of the hepatitis C virus. The invention also provides pharmaceutical compositions comprising such compounds, methods of using such compounds to treat hepatitis C viral infections, and processes and intermediates useful for preparing such compounds.

21 Claims, No Drawings

PIPERAZINE-PIPERIDINE COMPOUNDS AS HEPATITIS C VIRUS INHIBITORS

CROSS-REFERENCE TO RELATED APPLICATIONS

This application claims the benefit of U.S. Provisional Application Nos. 61/637,959, filed on Apr. 25, 2012 and 61/774,033, filed on Mar. 7, 2013, the disclosures of which are incorporated herein by reference in their entirety.

BACKGROUND OF THE INVENTION

1. Field of the Invention

The invention is directed to compounds useful as inhibitors of replication of the hepatitis C virus (HCV). The invention is also directed to pharmaceutical compositions comprising such compounds, methods of using such compounds to treat HCV infection, and processes and intermediates useful for preparing such compounds.

2. State of the Art

Recent estimates place the number of people infected with the hepatitis C virus (HCV) worldwide at more than 170 million, including 3 million people in the United States. The infection rate is thought to be roughly 4 to 5 times that of the human immunodeficiency virus (HIV). While in some individuals, the natural immune response is able to overcome the virus, in the majority of cases, a chronic infection is established, leading to increased risk of developing cirrhosis of the liver and hepatocellular carcinomas. Infection with hepatitis C, therefore, presents a serious public health problem.

Prior to mid-2011, the accepted standard of care for HCV involved the use of a pegylated interferon which is believed to act by boosting the body's immune response, together with ribavirin. Unfortunately, the course of treatment is lengthy, typically 48 weeks, often accompanied by serious adverse side effects, including depression, flu-like symptoms, fatigue, and hemolytic anemia, and ineffective in up to 50% of patients. In mid-2011, two HCV protease inhibitors were approved in the United States to be used in combination with interferon and ribavirin. Although better cure rates have been reported, the course of therapy is still lengthy and accompanied by undesirable side effects. Accordingly, there remains a serious unmet need in HCV treatment.

The virus responsible for HCV infection has been identified as a positive-strand RNA virus belonging to the family Flaviviridae. The HCV genome encodes a polyprotein that during the viral lifecycle is cleaved into ten individual proteins, including both structural and non-structural proteins. The six non-structural proteins, denoted as NS2, NS3, NS4A, NS4B, NS5A, and NS5B have been shown to be required for RNA replication. In particular, the NS5A protein appears to play a significant role in viral replication, as well as in modulation of the physiology of the host cell. Effects of NS5A on interferon signaling, regulation of cell growth and apoptosis have also been identified. (Macdonald et al., *Journal of General Virology* (2004), 85, 2485-2502.) Compounds which inhibit the function of the NS5A protein are expected to provide a new approach to HCV therapy.

SUMMARY OF THE INVENTION

In one aspect, the invention provides novel compounds which inhibit replication of the HCV virus.

Accordingly, the invention provides a compound of formula (I):

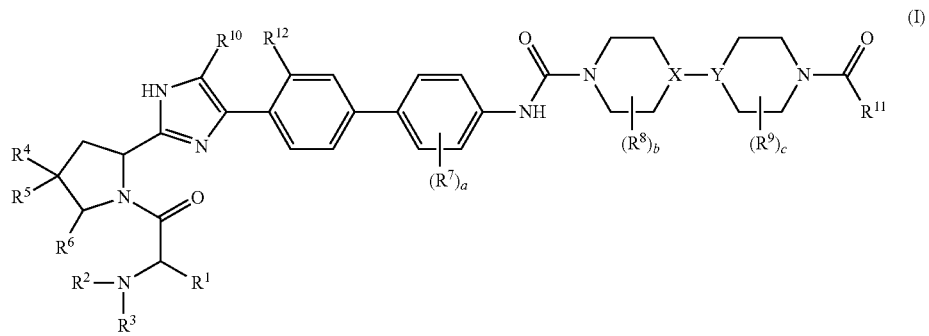

wherein $R^1$ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —$OR^a$, amino, —$SR^e$, heterocycle, or heteroaryl, $C_{1-6}$alkoxy is optionally substituted with —$OR^a$, and heterocycle is optionally substituted with —$OR^a$, amino, or —C(O)O$C_{1-6}$alkyl, or with one or two $C_{1-3}$alkyl;

$R^2$ is selected from hydrogen and $C_{1-6}$alkyl;

$R^3$ is selected from hydrogen, $C_{1-6}$alkyl, —C(O)O$C_{1-6}$alkyl, —C(O)N$R^m R^n$, —C(O)$C_{3-6}$cycloalkyl, and —S(O)$_2 C_{1-3}$alkyl;

$R^4$, $R^5$, and $R^6$ are each hydrogen;

or $R^4$ is selected from $C_{1-6}$alkyl, —N$R^b R^c$, —$OR^d$, —CN, —C(O)N$R^a R^b$, and halo; and $R^5$ and $R^6$ are hydrogen;

or $R^4$ and $R^5$ are independently $C_{1-6}$alkyl or halo and $R^6$ is hydrogen;

or $R^4$ and $R^5$ taken together form —O—(CH$_2$)$_2$—O— and $R^6$ is hydrogen;

or $R^4$ is hydrogen and $R^5$ and $R^6$ taken together form —(CH$_2$)$_n$—, wherein n is 1, 2, 3, or 4;

or $R^4$ and $R^5$ are hydrogen, and $R^6$ is $C_{1-6}$alkyl, $R^7$ is selected from halo, $C_{1-3}$alkyl, and $C_{1-3}$alkoxy wherein $C_{1-3}$alkyl and $C_{1-3}$alkoxy are optionally substituted with one, two, three, four, or five halo;

a is 0, 1, or 2;

$R^8$ is $C_{1-3}$alkyl optionally substituted with —$OR^h$;

b is 0, 1 or 2;

or when b is 2, two $R^8$ can be joined to form —(CH$_2$)$_2$—;

$R^9$ is $C_{1-3}$alkyl;

c is 0, 1 or 2;

$R^{10}$ is hydrogen, halo, or $C_{1-3}$alkyl substituted with one, two, or three halo, or with —$OR^h$;

$R^{11}$ is selected from $C_{1-6}$alkyl, $C_{3-10}$cycloalkyl, $C_{1-6}$alkoxy, —N$R^f R^g$, heteroaryl, heterocycle, and —CH$_2$-heteroaryl;

wherein:
C$_{1-6}$alkyl is optionally substituted with one or two substituents independently selected from —OR$^h$, —NR$^j$R$^k$, and phenyl;
C$_{1-6}$alkoxy is optionally substituted with —OR$^h$ or with phenyl;
any C$_{3-10}$cycloalkyl is optionally substituted with one or two substituents independently selected from C$_{1-3}$alkyl, —CD$_3$, halo, and —OR$^h$;
any heterocycle is optionally substituted with one, two, or three substituents independently selected from C$_{1-3}$alkyl, halo, —C(O)OC$_{1-3}$alkyl, and —C(O)C$_{1-6}$alkyl, wherein any —C(O)C$_{1-6}$alkyl is optionally substituted with —NHC(O)OC$_{1-3}$alkyl;
any heteroaryl is optionally substituted with one or two C$_{1-3}$alkyl;
R$^{12}$ is hydrogen or R$^{10}$ and R$^{12}$ taken together form —CH=CH— or —(CH$_2$)$_2$—;
R$^a$, R$^b$, R$^c$, R$^d$, R$^e$, R$^f$, R$^h$, R$^j$, R$^m$, and R$^n$ are each independently hydrogen or C$_{1-3}$alkyl;
R$^g$ is selected from hydrogen, C$_{1-6}$alkyl, and C$_{3-6}$cycloalkyl;
R$^k$ is selected from hydrogen, —C(O)C$_{1-3}$alkyl, —C(O)OC$_{1-3}$alkyl, —C(O)ONR$^b$R$^c$; and —C(O)NR$^b$R$^c$; and
X is N and Y is CH or X is CH and Y is N;
provided that when X is CH, b is 0 and when Y is CH, c is 0;
or a pharmaceutically-acceptable salt or stereoisomer thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier. In addition, the invention provides a pharmaceutical composition comprising a compound of the invention, a pharmaceutically-acceptable carrier and one or more other therapeutic agents useful for treating hepatitis C viral infections.

The invention also provides a method of treating a hepatitis C viral infection in a mammal, the method comprising administering to the mammal a therapeutically effective amount of a compound or of a pharmaceutical composition of the invention. In addition, the invention provides a method of treating a hepatitis C viral infection in a mammal, the method comprising administering to the mammal a compound or a pharmaceutical composition of the invention and one or more other therapeutic agents useful for treating hepatitis C viral infections. Further, the invention provides a method of inhibiting replication of the hepatitis C virus in a mammal, the method comprising administering a compound or a pharmaceutical composition of the invention.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a hepatitis C viral infection in a mammal.

DETAILED DESCRIPTION OF THE INVENTION

Among other aspects, the invention provides inhibitors of HCV replication of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, R$^1$ is selected from C$_{1-6}$alkyl, C$_{1-6}$alkoxy, phenyl, C$_{3-6}$cycloalkyl, heterocycle, and heteroaryl, wherein C$_{1-6}$alkyl is optionally substituted with —OR$^a$, amino, —SR$^c$, heterocycle, or heteroaryl, C$_{1-6}$alkoxy is optionally substituted with —OR$^a$, and heterocycle is optionally substituted with —OR$^a$, amino, or —C(O)OC$_{1-6}$alkyl, or with one or two C$_{1-3}$alkyl.

In another specific aspect, R$^1$ is selected from C$_{1-6}$alkyl, phenyl, and heterocycle, wherein C$_{1-6}$alkyl is optionally substituted with —OR$^a$, and heterocycle has six ring atoms and is optionally substituted with —OR$^a$ or amino or with one or two methyl.

In another specific aspect, R$^1$ is selected from C$_{1-6}$alkyl, phenyl, and tetrahydropyranyl, wherein C$_{1-6}$alkyl is optionally substituted with —OR$^a$; wherein R$^a$ is hydrogen or C$_{1-3}$alkyl.

In another specific aspect, R$^1$ is C$_{1-6}$alkyl, optionally substituted with hydroxy or methoxy, or tetrahydropyran. In another specific aspect, R$^1$ is selected from C$_{1-6}$alkyl and phenyl.

In a specific aspect, R$^1$ is C$_{1-3}$alkyl.
In another specific aspect, R$^1$ is isopropyl.
In yet another specific aspect, R$^1$ is phenyl.
In still another specific aspect, R$^1$ is tetrahydropyranyl.
In still another specific aspect, R$^1$ is tetrahydropyran-4-yl.
In a specific aspect, R$^2$ is hydrogen or C$_{1-6}$alkyl.
In other specific aspects, R$^2$ is hydrogen or C$_{1-3}$alkyl; or R$^2$ is hydrogen.

In a specific aspect, R$^3$ is selected from hydrogen, C$_{1-6}$alkyl, —C(O)OC$_{1-6}$alkyl, —C(O)NR$^m$R$^n$, —C(O)C$_{3-6}$cycloalkyl, and —S(O)$_2$C$_{1-3}$alkyl;
In another specific aspect, R$^3$ is selected from hydrogen, C$_{1-6}$alkyl, and —C(O)OC$_{1-6}$alkyl.
In yet another specific aspect, R$^3$ is —C(O)OC$_{1-3}$alkyl.
In a specific aspect, R$^1$ is C$_{1-6}$alkyl, R$^2$ is hydrogen, and R$^3$ is —C(O)OC$_{1-6}$alkyl.
In another specific aspect, R$^1$ is isopropyl, R$^2$ is hydrogen, and R$^3$ is —C(O)OCH$_3$.
In yet other specific aspects, R$^1$ is phenyl, R$^2$ is hydrogen, and R$^3$ is —C(O)OC$_{1-3}$alkyl; or R$^1$ is tetrahydropyranyl, R$^2$ is hydrogen, and R$^3$ is —C(O)OC$_{1-3}$alkyl.

In a specific aspect, R$^4$, R$^5$, and R$^6$ are each hydrogen; or R$^4$ is selected from C$_{1-6}$alkyl, —NR$^b$R$^c$, —OR$^d$, —CN, —C(O)NR$^a$R$^b$ and halo; and R$^5$ and R$^6$ are hydrogen; or R$^4$ and R$^5$ are independently C$_{1-6}$alkyl or halo and R$^6$ is hydrogen; or R$^4$ and R$^5$ taken together form —O—(CH$_2$)$_2$—O— and R$^6$ is hydrogen; or R$^4$ is hydrogen and R$^5$ and R$^6$ taken together form —(CH$_2$)$_n$—, wherein n is 1, 2, 3, or 4; or R$^4$ and R$^5$ are hydrogen, and R$^6$ is C$_{1-6}$alkyl.

In a specific aspect, R$^4$, R$^5$, and R$^6$ are each hydrogen.
In another specific aspect, R$^4$ is selected from C$_{1-6}$alkyl, —OR$^d$, halo, and —C(O)NR$^a$R$^b$ and R$^5$ and R$^6$ are hydrogen.
In another specific aspect, R$^4$ is selected from methyl, methoxy, fluoro, and —C(O)NH$_2$, and R$^5$ and R$^6$ are hydrogen.
In still another aspect, R$^4$ is methyl or methoxy, and R$^5$ and R$^6$ are hydrogen.
In a further aspect, R$^4$ is methyl and R$^5$ and R$^6$ are hydrogen.
In another specific aspect, R$^4$ and R$^5$ are independently C$_{1-6}$alkyl and R$^6$ is hydrogen.

In yet another specific aspect, $R^4$ and $R^5$ taken together form —O—$(CH_2)_2$—O— and $R^6$ is hydrogen.

In additional aspects, $R^4$ is hydrogen and $R^5$ and $R^6$ taken together form —$(CH_2)_n$—, wherein n is 1 or 4; or $R^4$ is hydrogen and $R^5$ and $R^6$ taken together form —$(CH_2)_4$—.

In still further aspects, $R^4$ and $R^5$ are each hydrogen and $R^6$ is $C_{1-6}$alkyl, or $R^4$ and $R^5$ are each hydrogen and $R^6$ is methyl.

In a specific aspect, $R^7$ is selected from halo, $C_{1-3}$alkyl, and $C_{1-3}$alkoxy wherein $C_{1-6}$alkyl and $C_{1-6}$alkoxy are optionally substituted with one, two, three, four, or five halo.

In another specific aspect $R^7$ is selected from halo, $C_{1-3}$alkyl, and $C_{1-3}$alkoxy wherein $C_{1-6}$alkyl and $C_{1-6}$alkoxy are substituted with one, two, or three halo.

In yet another specific aspect, $R^7$ is selected from fluoro, chloro, —$CF_3$, and —$OCF_3$.

In still another aspect, $R^7$ is —$OCF_3$.

In a specific aspect, $R^8$ is $C_{1-3}$alkyl.

In another specific aspect, $R^8$ is methyl.

In a specific aspect, $R^9$ is $C_{1-3}$alkyl.

In another specific aspect, $R^9$ is methyl.

In a specific aspect, $R^{10}$ is hydrogen, halo, or $C_{1-3}$alkyl substituted with one, two, or three halo, or with —$OR^h$.

In other specific aspects, $R^{10}$ is hydrogen or halo; or $R^{10}$ is hydrogen, chloro, or fluoro; or $R^{10}$ is hydrogen or —$CH_2OH$.

In another specific aspect, $R^{10}$ is chloro.

In yet another specific aspect, $R^{10}$ is hydrogen.

In a still further aspect, $R^{10}$ is —$CH_2OH$.

In a specific aspect, $R^{11}$ is defined as in formula (I).

In another specific aspect, $R^{11}$ is selected from $C_{1-6}$alkyl, $C_{3-6}$cycloalkyl, $C_{1-6}$alkoxy, —$NR^fR^g$, heteroaryl, heterocycle, and —$CH_2$-heteroaryl; wherein any heteroaryl or heterocycle has 5 or 6 ring atoms; $C_{1-6}$alkyl is optionally substituted with one or two substituents independently selected from —$OR^h$ and —$NR^jR^k$; any $C_{3-6}$cycloalkyl is optionally substituted with one or two $C_{1-3}$alkyl or halo; any heterocycle is optionally substituted with one, or two substituents independently selected from $C_{1-3}$alkyl and —$C(O)C_{1-6}$alkyl, wherein any —$C(O)C_{1-6}$alkyl is optionally substituted with —$NHC(O)OC_{1-3}$alkyl, In yet another aspect, $R^{11}$ is selected from $C_{1-6}$alkyl, $C_{3-6}$cycloalkyl, and $C_{1-6}$alkoxy wherein $C_{1-6}$alkyl is optionally substituted with —$OR^h$ and $C_{3-6}$cycloalkyl is optionally substituted with one or two $C_{1-3}$alkyl;

In still another aspect, $R^{11}$ is selected from tert-butyl, cyclopropyl, 2,2-dimethylcyclopropyl, cyclobutyl, 2,2-dimethylcyclobutyl, 3-hydroxy-2,2-dimethylpropyl, and tert-butoxy.

In a specific aspect, $R^{12}$ is hydrogen.

In another specific aspect, $R^{10}$ and $R^{12}$ taken together form —CH=CH— or —$(CH_2)_2$—.

In another specific aspect, $R^{10}$ and $R^{12}$ taken together form —CH=CH—.

In a specific aspect, a is 0, 1, or 2.

In another specific aspect, a is 1 or 2.

In another specific aspect, a is 1.

In a specific aspect, b is 0, 1, or 2.

In other specific aspects, b is 0 or b is 1.

In a specific aspect, c is 0, 1, or 2.

In other specific aspects, c is 0 or c is 1.

In a specific aspect, X is N, Y is CH, and c is 0.

In another specific aspect, X is CH, Y is N, and b is 0.

In another aspect, the invention provides compounds of formula (II):

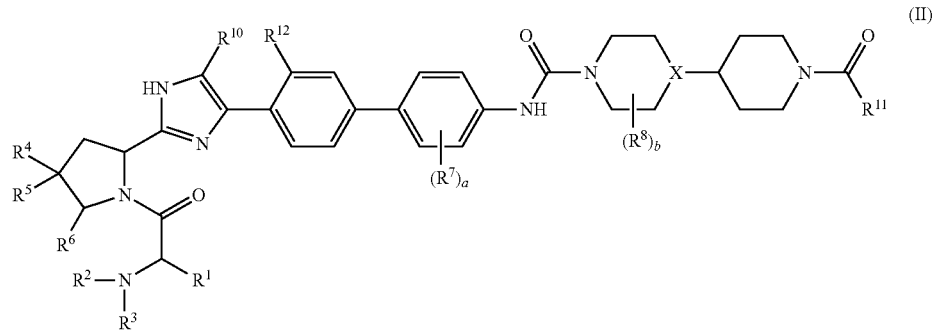

(II)

wherein the variables of formula (II) are as defined herein.

In another aspect, the invention provides compounds of formula (III)

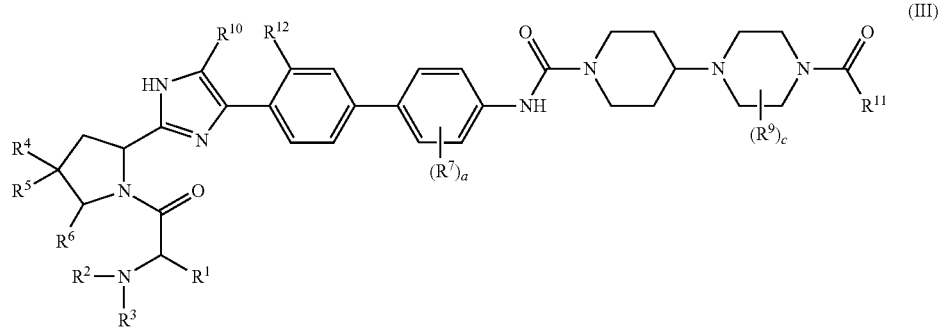

(III)

wherein the variables of formula (III) are as defined herein.

In yet another aspect, the invention provides compounds of formula (IV):

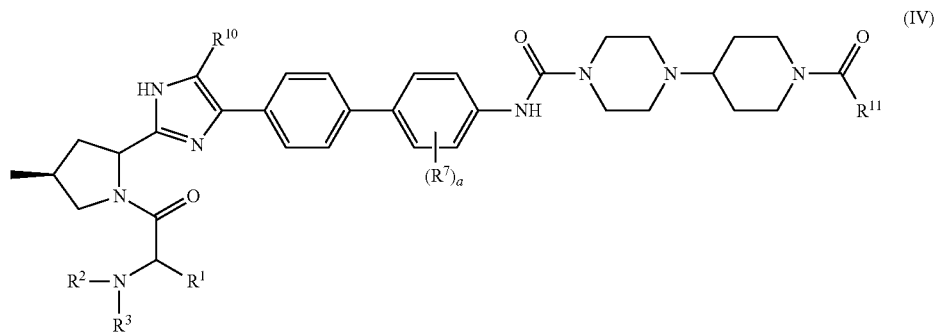

(IV)

wherein:
R¹ is selected from $C_{1-6}$alkyl optionally substituted with hydroxy or methoxy, tetrahydropyran and phenyl; R² is hydrogen; and R³ is —C(O)O$C_{1-6}$alkyl;
R² is hydrogen; and R³ is —C(O)O$C_{1-6}$alkyl;
R⁷ is selected from fluoro, chloro, —CF₃, and —OCF₃;
R¹¹ is selected from $C_{1-6}$alkyl, $C_{3-6}$cycloalkyl, and $C_{1-6}$alkoxy wherein $C_{1-6}$alkyl is optionally substituted with —OR$^h$ and $C_{3-6}$cycloalkyl is optionally substituted with one or two $C_{1-3}$alkyl;
R¹⁰ is hydrogen, chloro, or fluoro; and
a is 1 or 2;
or a pharmaceutically-acceptable salt thereof.

Included within this aspect are compounds wherein R¹¹ is selected from tert-butyl, cyclopropyl, 2,2-dimethylcyclopropyl, cyclobutyl, 2,2-dimethylcyclobutyl, 3-hydroxy-2,2-dimethylpropyl, and tert-butoxy.

In yet another aspect, the invention provides compounds of formula (V):

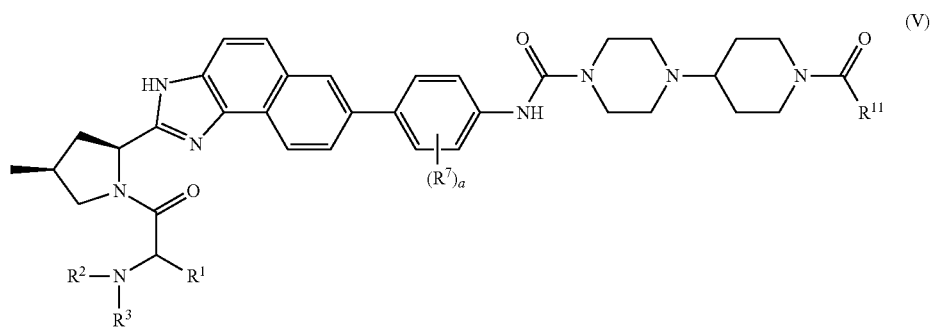

(V)

wherein:
R¹ is selected from $C_{1-6}$alkyl optionally substituted with hydroxy or methoxy, tetrahydropyran and phenyl; R² is hydrogen; and R³ is —C(O)O$C_{1-6}$alkyl;
R⁷ is selected from fluoro, chloro, —CF₃, and —OCF₃;
R¹¹ is selected from $C_{1-6}$alkyl, $C_{3-6}$cycloalkyl, and $C_{1-6}$alkoxy wherein $C_{1-6}$alkyl is optionally substituted with —OR$^h$ and $C_{3-6}$cycloalkyl is optionally substituted with one or two $C_{1-3}$alkyl; and
a is 1 or 2;
or a pharmaceutically-acceptable salt thereof.

Included within this aspect are compounds wherein R¹¹ is selected from tert-butyl, cyclopropyl, 2,2-dimethylcyclopropyl, cyclobutyl, 2,2-dimethylcyclobutyl, 3-hydroxy-2,2-dimethylpropyl, and tert-butoxy.

In one aspect, the invention provides the compounds of Examples 1-17 and Tables 1-9 below
In another aspect, the invention provides a compound selected from the following compounds
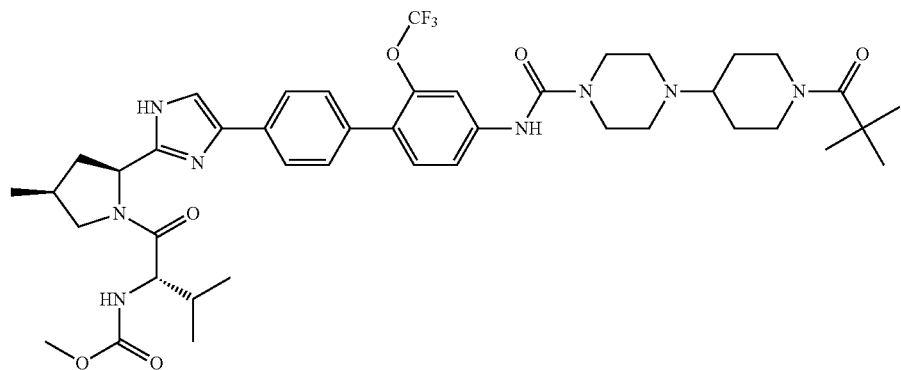
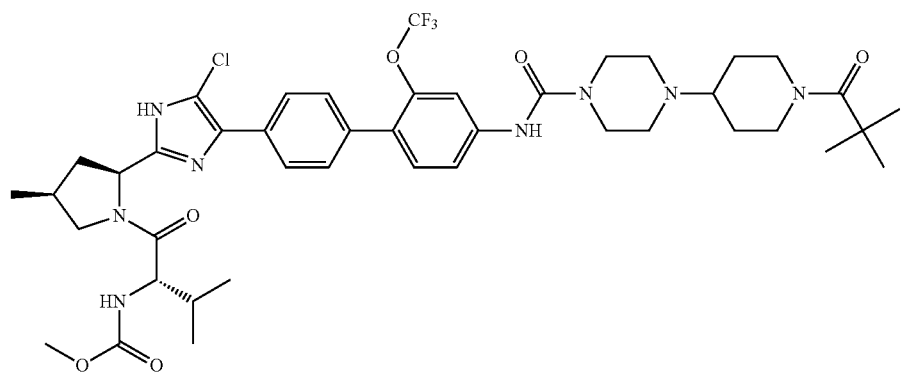
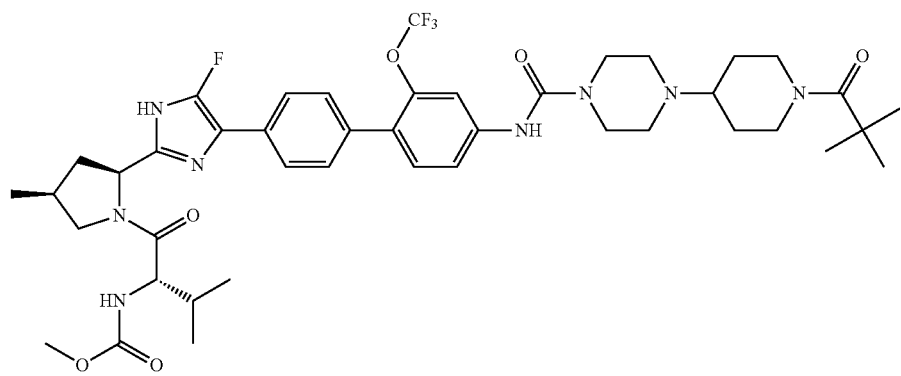
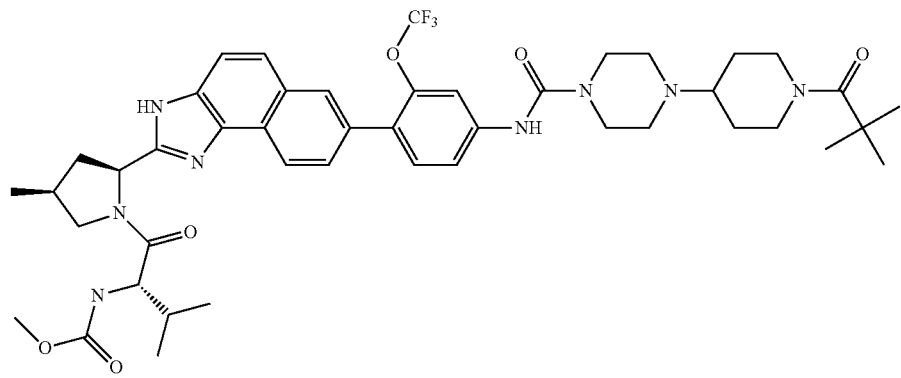

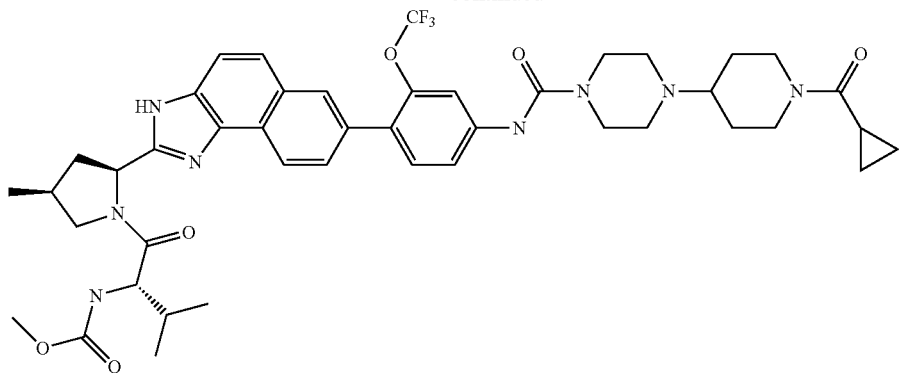
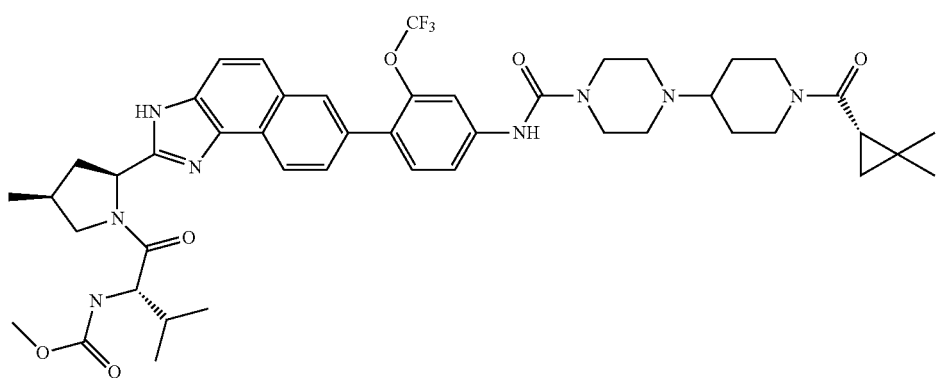
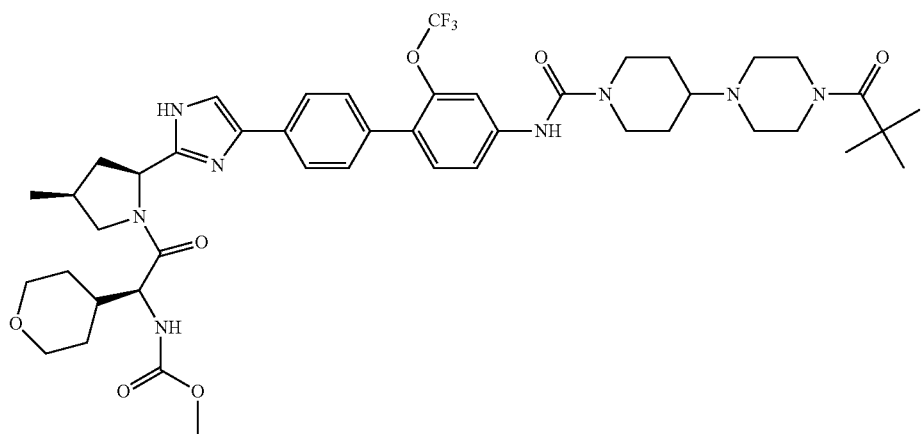
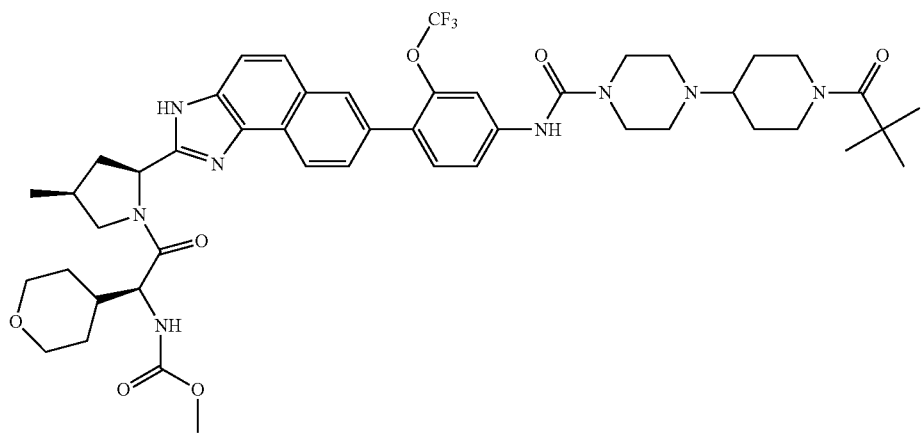

-continued
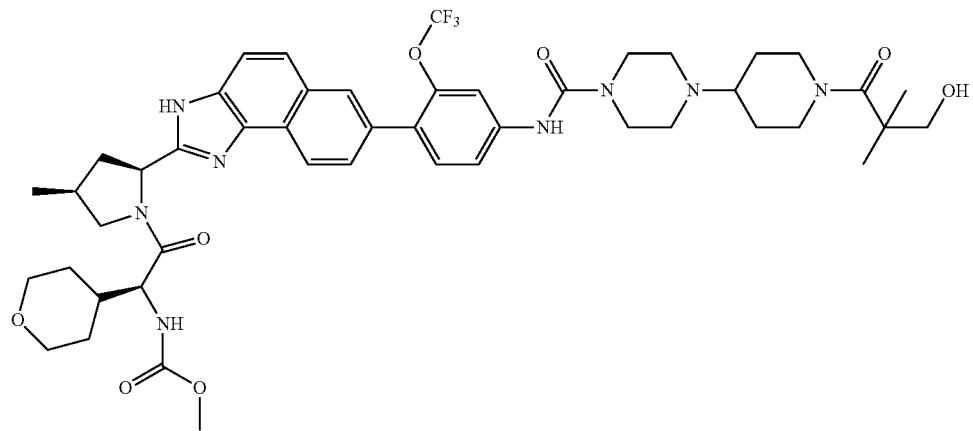
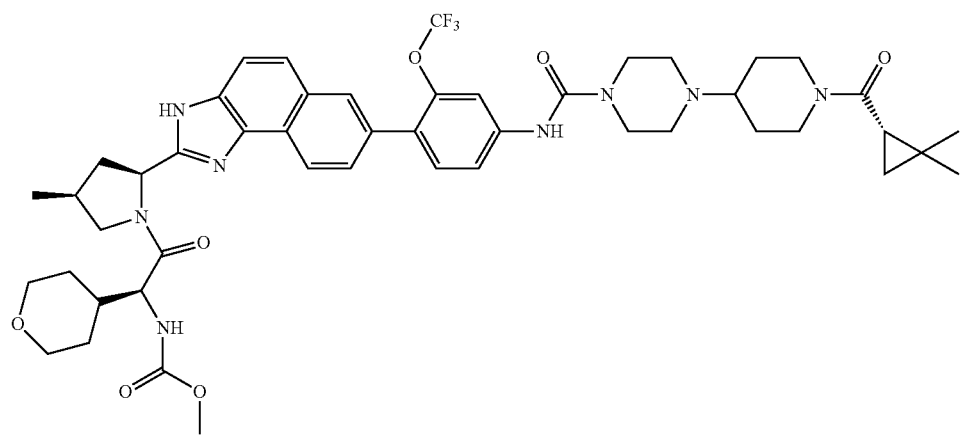
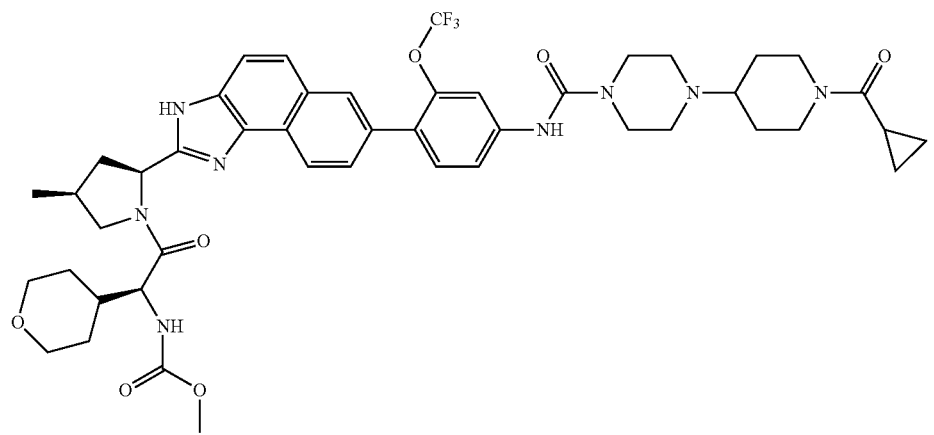

-continued

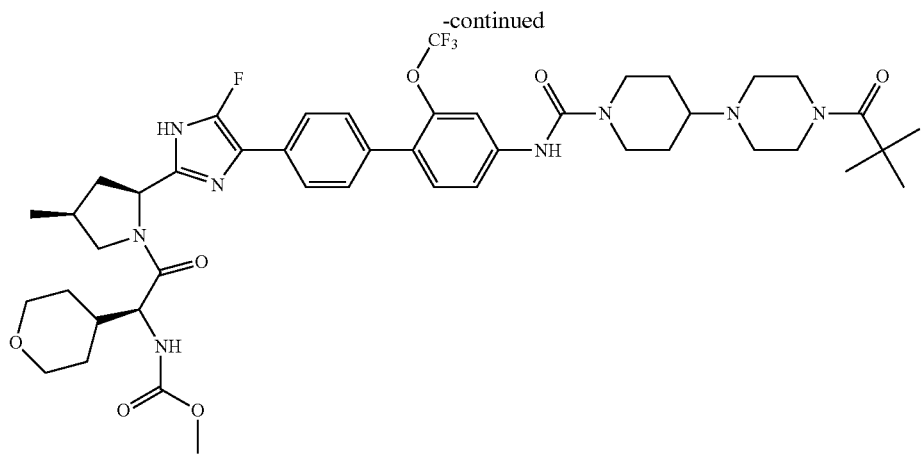

and pharmaceutically-acceptable salts thereof.

The chemical naming convention used herein is illustrated for the compound of Example 7:

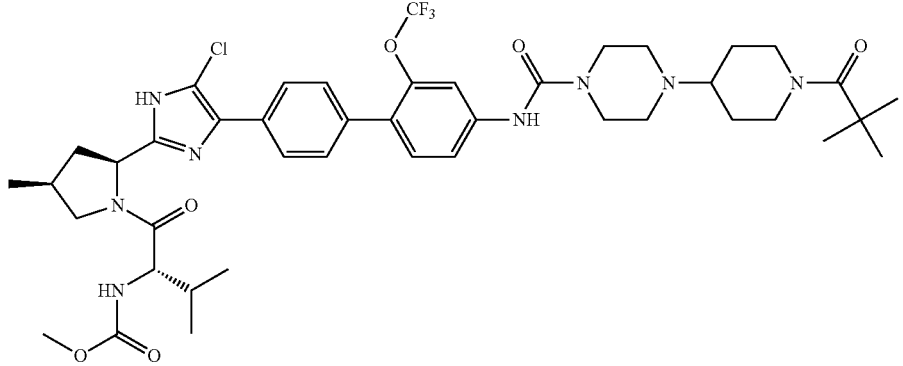 [SMILES: COC(=O)N[C@H](C(=O)N1C[C@@H](C)C[C@H]1c1nc(-c2ccc(-c3ccc(NC(=O)N4CCN(C5CCN(C(=O)C(C)(C)C)CC5)CC4)cc3OC(F)(F)F)cc2)c(Cl)[nH]1)C(C)C]

which is [(S)-1-((2S,4S)-2-{5-Chloro-4-[4'-({4-[1-(2,2-dimethyl-propionyl)-piperidin-4-yl]-piperazine-1-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester according to the IUPAC conventions as implemented in AutoNom software, (MDL Information Systems, GmbH, Frankfurt, Germany).

Furthermore, the imidazole moiety in the structure of formula (I) exists in tautomeric forms, illustrated below for a fragment of the compound of Example 2

A
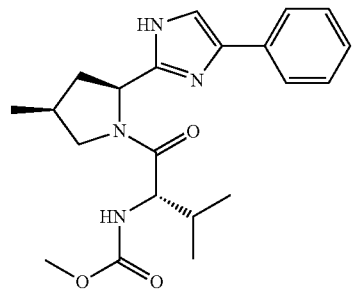

B
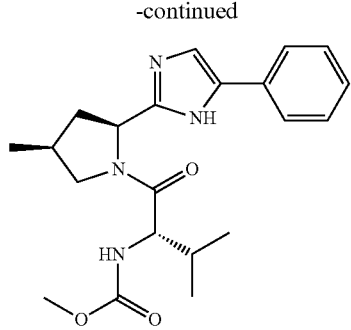

According to the IUPAC convention, these representations give rise to different numbering of the atoms of the imidazole moiety: {(S)-2-methyl-1-[(2S,4S)-4-methyl-2-(4-phenyl-1H-imidazol-2-yl)-pyrrolidine-1-carbonyl]-propyl}-carbamic acid methyl ester (structure A) vs. {(S)-2-methyl-1-[(2S,4S)-4-methyl-2-(5-phenyl-1H-imidazol-2-yl)-pyrrolidine-1-carbonyl]-propyl}-carbamic acid methyl ester (structure B).

Similarly, the napthimidazole structure where the variables $R^{10}$ and $R^{12}$ taken together form —CH=CH—, illustrated for a fragment of the compound of Example 15, exists in tautomeric forms:

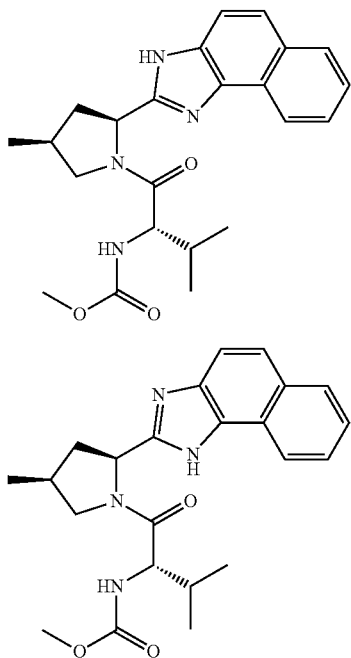

which also give rise to different numbering: {(S)-2-methyl-1-[(2S,4S)-4-methyl-2-(3H-naphtho[1,2-d]imidazol-2-yl)-pyrrolidine-1-carbonyl]-propyl}-carbamic acid methyl ester (structure C) vs. {(S)-2-methyl-1-[(2S,4S)-4-methyl-2-(1H-naphtho[1,2-d]imidazol-2-yl)-pyrrolidine-1-carbonyl]-propyl}-carbamic acid methyl ester (structure D). It will be understood that although structures are shown, or named, in a particular form, the invention also includes the tautomer thereof.

The compounds of the invention contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^2H$, $^3H$, $^{11}C$, $^{13}C$, $^{14}C$, $^{13}N$, $^{15}N$, $^{15}O$, $^{17}O$, $^{18}O$, $^{35}S$, $^{36}Cl$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like When a specific number of carbon atoms are intended for a particular term, the number of carbon atoms is shown preceding the term. For example, the term "$C_{1-3}$alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, etc.

The term "heteroaryl" or "heteroaryl ring" means a monovalent aromatic group having from 5 to 10 total ring atoms, wherein the ring contains from 1 to 9 carbon ring atoms and from 1 to 4 ring heteroatoms selected from nitrogen, oxygen, and sulfur. Heteroaryl groups may be monocyclic or multicyclic. Representative heteroaryl groups include, by way of example, pyrroyl, isoxazolyl, isothiazolyl, pyrazolyl, oxazolyl, oxadiazolyl, thiadiazolyl, thiazolyl, imidazolyl, triazolyl, tetrazolyl, furanyl, triazinyl, thienyl, pyridyl (or, equivalently, pyridinyl), pyrimidyl, pyridazinyl, pyrazinyl, indolyl, benzofuranyl, benzothienyl, benzimidazolyl, benzthiazolyl, and the like, where the point of attachment is at any available carbon or nitrogen ring atom. Where the context makes the point of attachment of the heteroaryl group evident, such groups may alternatively be referred to as a non-valent species, i.e. pyrrole, isoxazole, isothiazole, pyrazole, imidazole, etc.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition in a patient (such as hepatitis C viral infection), such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like. Numerous protecting groups, and their introduction and removal, are described in T. W. Greene and G. M. Wuts, *Protecting Groups in Organic Synthesis*, Third Edition, Wiley, New York.

General Synthetic Procedures

Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

In one exemplary method of synthesis, compounds of formula (1-6) in which X is N and Y is CH are prepared as shown in Scheme 1:

Scheme 1

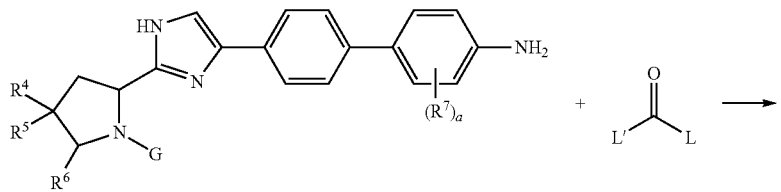

1-1

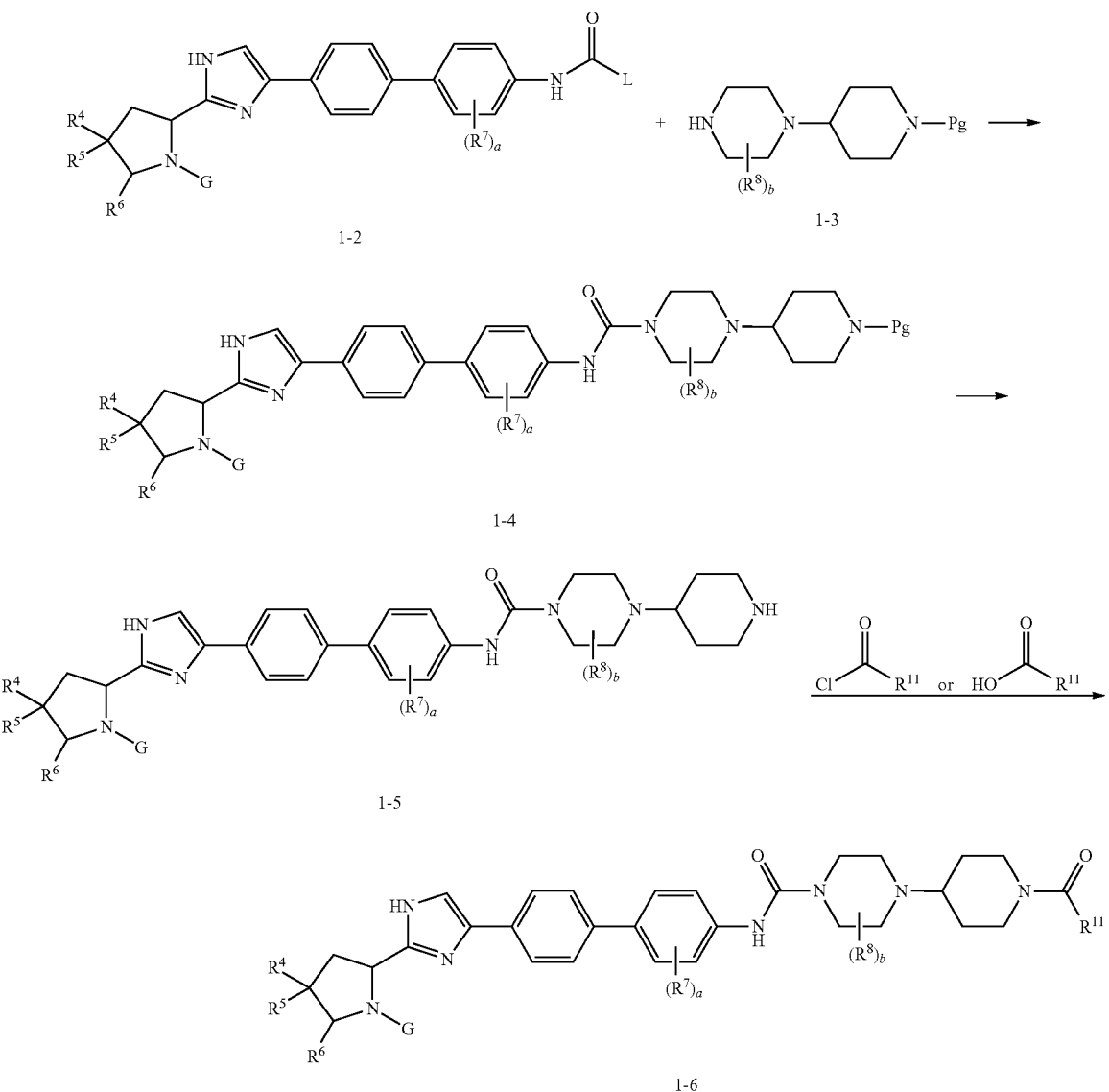

where G represents the group

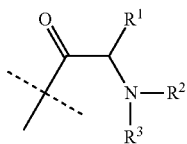

L and L' represent leaving groups, and Pg represents an amino-protecting group. For example, 1,1'-carbonyldiimidazole (CDI) or 4-nitrophenyl chloroformate or triphospgene may be used as the acylating agent, L-C(O)-L'. Aniline intermediate 1-1 is reacted with the acylating agent to form the adduct 1-2 which is reacted with a protected piperazine-piperidine intermediate 1-3 to form a protected intermediate 1-4. Intermediate 1-4 is then deprotected, for example, by treatment with an acid to provide compound 1-5, which is reacted with an acid chloride in the presence of base or with a carboxylic acid under amide bond formation conditions to prepare a compound of the invention of formula 1-6. The amide bond formation reaction may utilize coupling agents such as N,N,N',N'-tetramethyl-O-(7-azabenzotriazol-1-yl) uronium hexafluorophosphate (HATU), or as 1,3-dicyclohexylcarbodiimide (DCC), 1-(3-dimethylaminopropyl)-3-ethylcarbodiimide (EDC), or other coupling agents known in the art.

Protected intermediate 1-4 may also be conveniently prepared by alternative processes, for example, by the Suzuki coupling reaction in the presence of a palladium catalyst (Miyaura and Suzuki, *Chem. Rev.* 1995, 95, 2457-2483). As shown in Scheme 2 below, either coupling partner may bear the boronate moiety. Alternatively, a boronic acid reagent may be used in place of a boronate reagent, such as the pinacol boronate depicted below.

Scheme 2

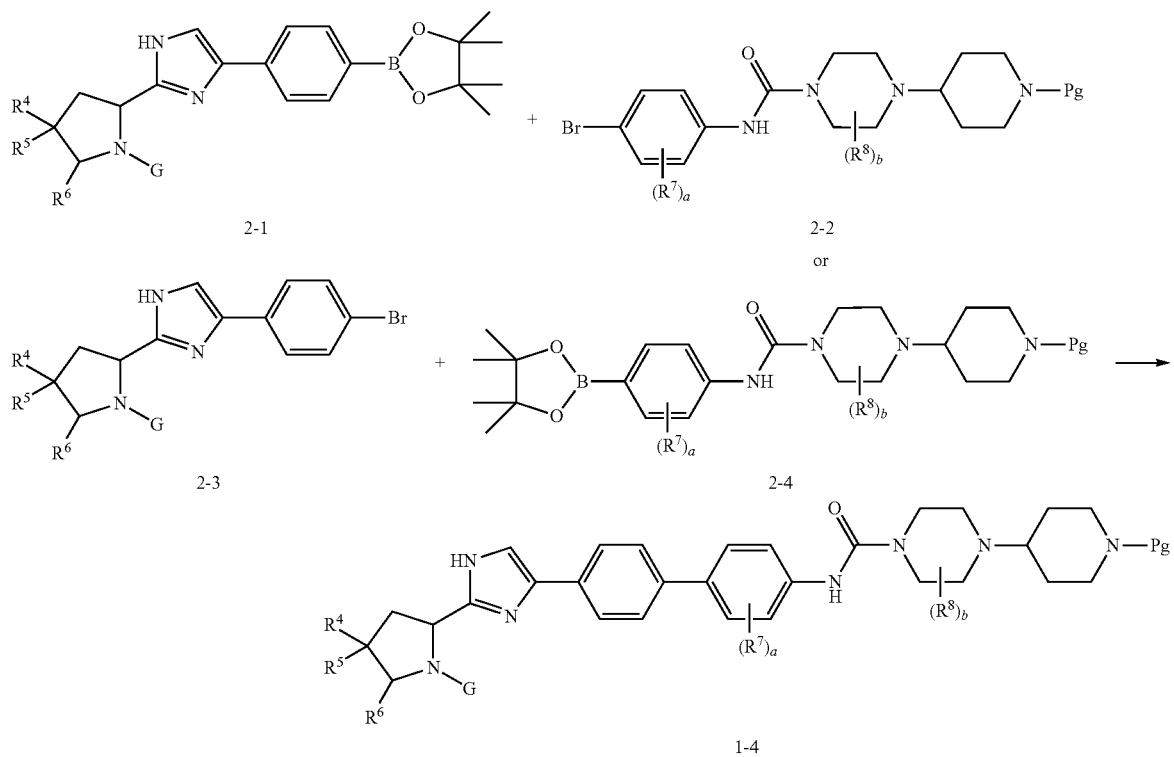

If protected intermediate 2-2 were replaced by an intermediate 2-2'

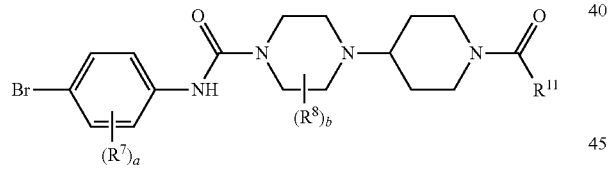

then the Suzuki coupling of the boronate 2-1 in the first line of Scheme 2 would directly provide a final compound of the invention. Similarly, if the protected intermediate 2-4 were replaced by an intermediate 2-4',

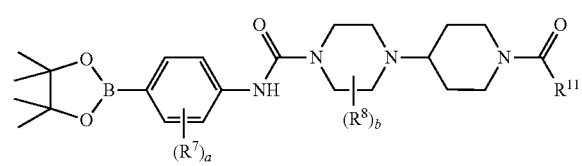

then the Suzuki coupling of the bromo intermediate 2-3 in the second line of Scheme 2 would directly provide a final compound of the invention.

As described in the examples below, napthimidazole compounds of the invention, of formula (V), may be prepared by a Suzuki coupling reaction analogous to that of the first line of Scheme 2, in which a suitable boronate intermediate corresponding to 2-1 is reacted with intermediate 2-2.

Compounds of the invention in which $R^{10}$ is chloro or fluoro are conveniently prepared by the Suzuki reaction of an intermediate 2-3'

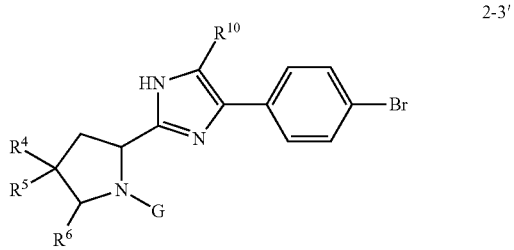

which may be prepared by reacting intermediate 2-3 with a chlorinating agent, such as N-chlorosuccinimide, or with a fluorinating agent, such as 1-fluoro-4-hydroxy-1,4-diazoniabicyclo[2.2.2]octane bis(tetrafluoroborate).

The bromo intermediate 2-2 may be prepared, for example, by reactions analogous to the acylation and leaving group replacement steps of Scheme 1 as shown in Scheme 3 below.

Scheme 3

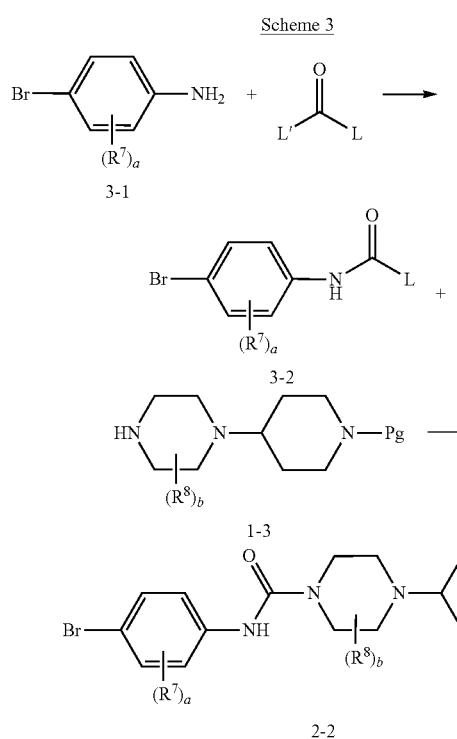

The protected piperazine-piperidine intermediate 1-3 may be prepared by the reductive amination of a protected piperazine with a protected carboxy piperidine as shown in Scheme 4 below where Pg' and Pg represent amino-protecting groups removable under different conditions. For example, to provide an intermediate 1-3 where Pg is Boc, it is useful to use Cbz as protecting group Pg'.

Scheme 4

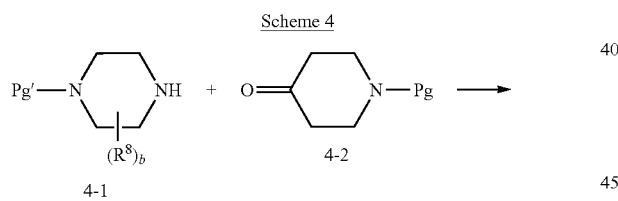

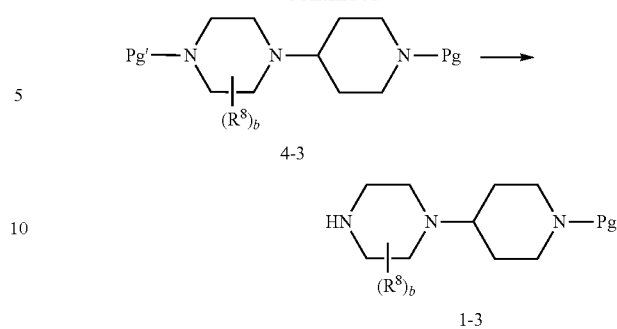

Compounds of the invention in which X is CH and Y is N may be prepared by reactions analogous to the reactions of Schemes 1 to 4 in which the intermediate 1-3 is replaced by a protected piperidine-piperazine intermediate 5-4 which may be prepared as shown in Scheme 5.

Scheme 5

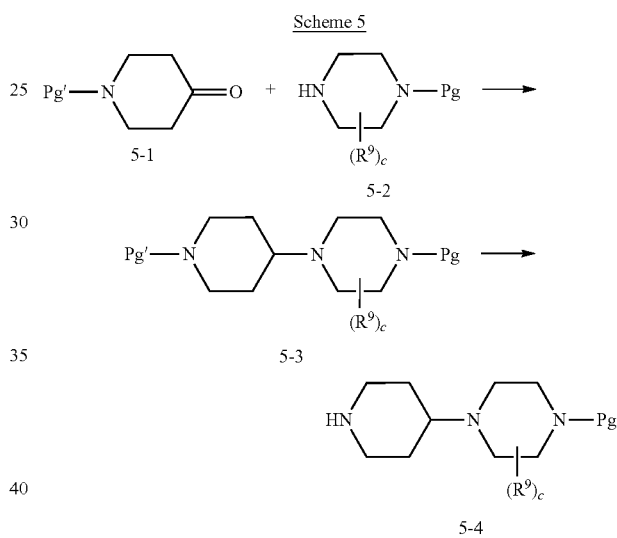

The biaryl aniline intermediate 1-1 may be prepared by the Suzuki coupling reaction of Scheme 6, where, as shown, either coupling partner may bear the boronate moiety.

Scheme 6

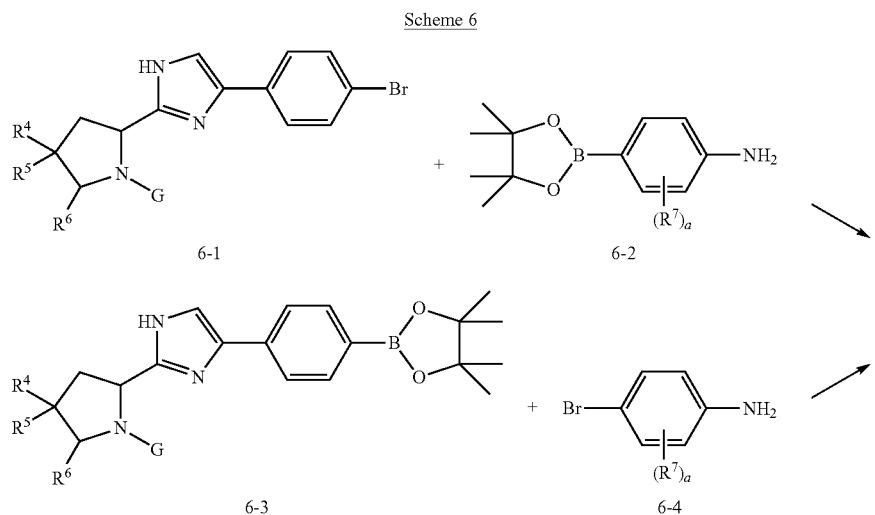

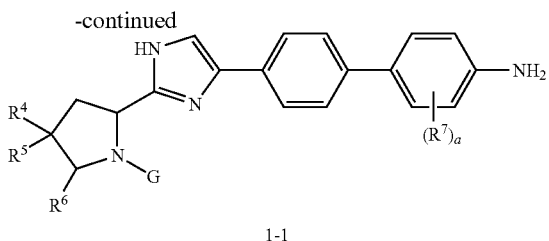

1-1

Intermediates 6-1 and 6-3 used in the Suzuki reaction of Scheme 6 may be prepared, for example, as shown in Schemes 7 and 8.

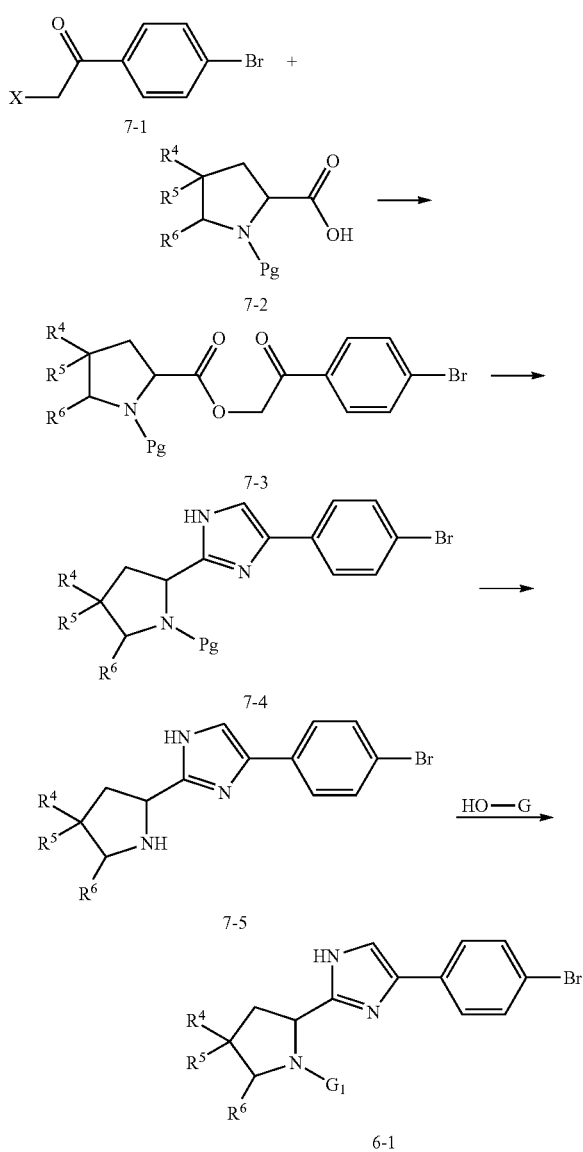

Reagent 7-1, where X represents bromo or chloro is reacted with a protected proline carboxylic acid 7-2 to provide intermediate 7-3 which is converted to intermediate 7-4 in the presence of an excess of ammonium acetate. The ring closure reaction typically is performed at a temperature between about 100° C. and about 120° C. for a period of about 4 to about 24 hours. To provide compound 6-1, intermediate 7-4 is typically deprotected and coupled with a reagent HO-G to provide compound 6-1.

Finally, to provide boronate intermediate 6-3, intermediate 6-1 is reacted with 8-1 in the presence of a palladium catalyst as shown in Scheme 8.

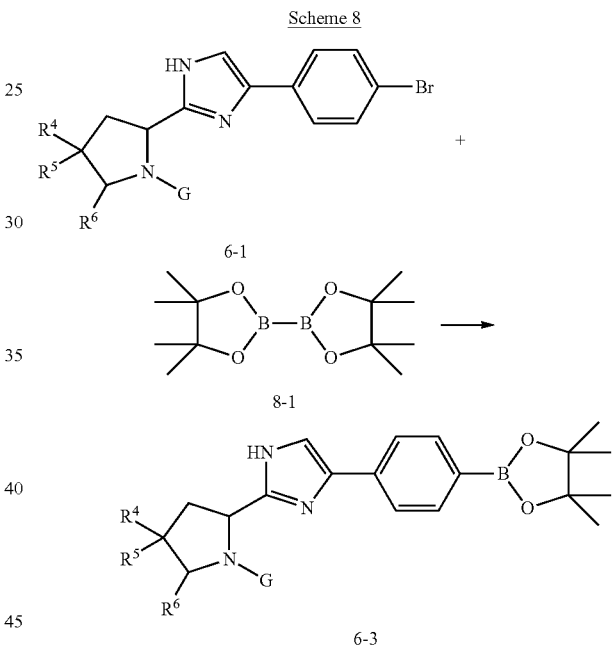

Details regarding specific reaction conditions and other procedures for preparing representative compounds of the invention or intermediates thereto are described in the examples below.

Thus, in one of its method aspects, the invention provides the processes of Schemes 1-5 and variations thereto described above as well as the processes exemplified below.

It will further be understood, this disclosure encompasses compounds of formula (I) when prepared by synthetic processes such as those described above and below or by metabolic processes including those occurring in vivo in human or animal body or in vitro.

Pharmaceutical Compositions

The compounds of the invention and pharmaceutically-acceptable salts thereof are typically used in the form of a pharmaceutical composition or formulation. Such pharmaceutical compositions may be administered to a patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formulas (II), (III), (IV), and (V) and pharmaceutically-acceptable salts thereof.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acidmethacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following non-limiting examples illustrate representative pharmaceutical compositions of the present invention.

Oral Solid Dosage Form

A compound of the invention is dissolved in polyethylene glycol acidified to pH≤2 with optional heating to form a solution comprising 10% w/w or 40% w/w active agent. The solution is spray dried to form a powder. The resulting powder is loaded into capsules, for example gelatin or hydroxypropyl methylcellulose capsules, to provide a unit dosage of 14 mg or 56 mg, respectively, active agent per capsule.

Oral Liquid Formulation

A compound of the invention (100 mg) is added to a mixture of ethanol (5 mL), propylene glycol (10 mL), and polyethylene glycol (25 mL). Once dissolution is achieved, acidified distilled water (q.s. to 100 mL) is added to provide a liquid formulation at a concentration of 1 mg/mL active agent.

Lipid Emulsion Formulation

A lipid emulsion formulation comprising a compound of the invention (10%), oleic acid (78%) polyethylene glycol (10%), and polysorbate 20 (2%) w/w is formed by adding a compound of the invention to a mixture of the remaining ingredients.

Lipid Emulsion Formulation

A lipid emulsion formulation comprising a compound of the invention (10%) and oleic acid (90%) w/w is formed by adding a compound of the invention to oleic acid.

Micro-Emulsion Formulation

A compound of the invention (1 g) is dissolved in a mixture of ethanol (2 mL), propylene glycol (2 mL), polyethylene glycol 400 (4 mL), and polyethylene glycol-15-hydroxystearate (4 mL). Acidified distilled water (q.s. to 100 mL) is added to form a self-emulsifying micro-emulsion formulation.

Utility

The compounds of the invention have been shown to inhibit viral replication in HCV replicon assays and therefore are expected to be useful for the treatment of hepatitis C viral infections.

In one aspect, therefore, the invention provides a method of inhibiting replication of the hepatitis C virus in a mammal (e.g., a human), the method comprising administering to the mammal a therapeutically-effective amount of a compound of the invention or of a pharmaceutical composition comprising a pharmaceutically-acceptable carrier and a compound of the invention.

The invention further provides a method of treating hepatitis C viral infections in a mammal (e.g., a human), the method comprising administering to the mammal a therapeutically-effective amount of compound of the invention or of a pharmaceutical composition comprising a pharmaceutically-acceptable carrier and a compound of the invention.

The compounds of the invention may inhibit viral replication by inhibiting the function of the NS5A protein encoded by the HCV genome. In one aspect, therefore, the invention provides a method of inhibiting the NS5A protein of HCV in a mammal, the method comprising administering to the mammal, a compound or a composition of the invention.

When used to treat HCV infections, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating HCV infections will range from about 1 to about 2000 mg/day of active agent, including from about 5 to about 300 mg/day and from about 10 to about 200 mg per day of active agent for an average 70 kg human.

Combination Therapy

Compounds of the invention may also be used in combination with one or more agents which act by the same mechanism or by different mechanisms to effect treatment of HCV. Useful classes of agents for combination therapy include, but are not limited to, HCV NS3 protease inhibitors, HCV NS5B nucleoside and non-nucleoside polymerase inhibitors, helicase inhibitors, NS4B protein inhibitors, HCV viral entry inhibitors, cyclophyllin inhibitors, toll-like receptor agonists, inhibitors of heat shock proteins, interfering RNA, antisense RNA, HCV internal ribosome entry site (IRES) inhibitors, thiazolides, nucleoside analogs such as ribavirin and related compounds, interferons and other immunomodulatory agents, inosine 5'-monophosphate dehydrogenase (IMPDH) inhibitors, and other NS5A protein inhibitors. Agents which act to inhibit HCV replication by any other mechanism may also be used in combination with the present compounds.

HCV NS3 protease inhibitors which may be used in combination therapy include, but are not limited to, Incivek® (telaprevir, VX-950), boceprevir (SCH-503034), simeprevir (TMC-435), narlaprevir (SCH-900518), vaniprevir (MK-7009), danoprevir (ITMN-191, R-7227), BI-201335, ABT-450/r, asunaprevir (BMS-650032), GS-9256, GS-9451, sovaprevir (ACH-1625), ACH-2684, BMS-605339, VX-985, PHX-1766, BMS-791325, IDX-320, and MK-5172.

Examples of HCV NS5B nucleoside polymerase inhibitors include, but are not limited to, mericitabine (RG7128), IDX-184, sofosbuvir (GS-7977, PSI-7977), PSI-7851, PSI-938, BMS-986094 (INX-189, INX-08189), RG7348, MK-0608, TMC-649128, HCV-796, and ALS-2200 (VX-135), while, non-nucleoside HCV NS5B polymerase inhibitors, include but are not limited to, filibuvir (PF-8685540), tegobuvir (GS-9190), VX-222, VX-759, setrobuvir (ANA-598), ABT-072, ABT-333, BI-207127, BMS-791325, MK-3281, IDX-37, BMS-824393, TMC-647055.

A wide variety of interferons and pegylated interferons, including alpha, beta, omega, and gamma interferons, having antiviral, antiproliferative or immunomodulatory effects, can be combined with the present compounds. Representative examples include, but are not limited to, Intron® A (interferon-alpha2b), Actimmune® (interferon-gamma-1b), Alferon N, Advaferon, Roferon-A (interferon alpha-2a), PegIntron® (peginterferon-alpha 2b), Alfaferone, Pegasys® (peginterferon alpha-2a), Alfanative (interferon alpha), Zalbin™ (albinterferon alpha-2b), Infergon® (interferon alfacon-1), Omega DUROS® (omega interferon), Locteron™ (interferon alpha), PEG-rIL-29 (pegylated interferon lambda), and Rebif® (interferon beta-1a).

Nucleoside analog antiviral agents include, but are not limited to, ribavirin (Copegus®, Rebetol®, Virazole®) and Viramidine (taribavirin). Interferons and ribavirin are also provided in in the form of kits which include, for example, but are not limited to, Rebetron® (interferon alpha-2b/ribavirin) and Pegetron® (Peginterferon alpha-2b/ribavirin).

Useful compounds acting by other mechanisms include, but are not limited to: cyclophilin inhibitors, such as DEB-025, SCY-635, NIM-811, and cyclosporine and derivatives; toll-like receptor agonists, such as resiquimod, IMO-2125, and ANA-773, HCV viral entry inhibitors, such as civacir, thiazolides, such as nitazoxanide, and broad-spectrum viral inhibitors, such as, inosine-5'-monophosphate dehydrogenase (IMPDH) inhibitors.

In addition, compounds of the invention may be combined with an NS5A inhibitor, for example, daclatasvir (BMS-790052), AZD-7295, PPI-461, PPI-1301, GS-5885, GSK2336805, ABT-267, ACH-2928, ACH-3102, EDP-239, IDX-719, MK-8742, or PPI-668.

In another aspect, therefore, the invention provides a therapeutic combination for use in the treatment of hepatitis C viral infections, the combination comprising a compound of the invention and one or more other therapeutic agents useful for treating HCV. For example, the invention provides a combination comprising a compound of the invention and one or more agents selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin and related nucleoside analogs. Also provided, therefore, is a pharmaceutical composition comprising a compound of the invention and one or more other therapeutic agents useful for treating HCV.

Further, in a method aspect, the invention provides a method of treating a hepatitis C viral infection in a mammal, the method comprising administering to the mammal a compound of the invention and one or more other therapeutic agents useful for treating HCV.

In another method aspect, the invention provides a method of inhibiting replication of the hepatitis C virus in a mammal, the method comprising administering to the mammal a compound of the invention and one or more other therapeutic agents useful for inhibiting replication of the hepatitis C virus.

For example, in one method aspect, the invention provides a method of treating a hepatitis C viral infection in a mammal, the method comprising administering to the mammal a compound of the invention, an interferon or pegylated interferon, and ribavirin.

In another exemplary method aspect, the invention provides a method of treating a hepatitis C viral infection in a mammal, the method comprising administering to the mammal a compound of the invention, an interferon or pegylated interferon, ribavirin, and an HCV NS3 protease inhibitor.

In still another method aspect, the invention provides a method of treating a hepatitis C viral infection in a mammal, the method comprising administering to the mammal a compound of the invention, an HCV NS3 protease inhibitor, and ribavirin.

Still other all-oral combination therapies useful in other method aspects, include, for example, a compound of the invention and an HCV NS3 protease inhibitor, a compound of the invention and an HCV NS5B nucleoside polymerase inhibitor, a compound of the invention, an HCV NS5B nucleoside polymerase inhibitor, and ribavirin; a compound of the invention, an HCV NS3 protease inhibitor, and an HCV NS5B nucleoside polymerase inhibitor; a compound of the invention, an HCV NS3 protease inhibitor, an HCV NS5B nucleoside polymerase inhibitor and ribavirin; a compound of the invention, an HCV NS3 protease inhibitor, and an HCV NS5B non-nucleoside polymerase inhibitor; and a compound of the invention, an HCV NS3 protease inhibitor, an HCV NS5B non-nucleoside polymerase inhibitor and ribavirin.

In another method aspect, the invention provides a method of inhibiting replication of the hepatitis C virus in a mammal, using a compound of the invention in combination with other agents, as described above.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Finally, the compounds of the invention may also find utility as research tools, for example, for discovering new HCV NS5A protein inhibitors or explicating mechanisms of HCV replication.

Compounds of the invention have been demonstrated to be potent inhibitors of HCV replication in HCV replicon assays, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
AcOH=acetic acid
CDI=1,1'-carbonyldiimidazole
DCM=dichloromethane
DIPEA=N,N-diisopropylethylamine
DMA=N,N-dimethylacetamide
DMF=N,N-dimethylformamide
DMSO=dimethyl sulfoxide
EDC=N-(3-dimethylaminopropyl)-N-ethylcarbodiimide hydrochloride
EtOAc=ethyl acetate
Et$_3$N=triethylamine
h=hour(s)
HATU=N,N,N',N'-tetramethyl-O-(7-azabenzotriazol-1-yl)uronium hexafluorophosphate
HCTU=2-(6-chloro-1H-benzotriazole-1-yl)-1,1,3,3-tetramethylaminium hexafluorophosphate
HOAt=1-hydroxy-7-azabenzotriazole
IPA=isopropylalcohol
MeOH=methanol
min=minute(s)
Pd$_2$(dba)$_3$=tris(dibenzylideneacetone)dipalladium(0)
Pd(dppf)Cl$_2$=dichloro(1,1'-bis(diphenylphosphino)-ferrocene)dipalladium(II)
MTBE=methyl tert-butyl ether
RT=room temperature
TFA=trifluoroacetic acid
THF=tetrahydrofuran
bis(pinacolato)diboron=4,4,5,5,4',4',5',5'-octamethyl-[2,2']bi[[1,3,2]dioxaborolanyl]

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument.

General Preparative HPLC Conditions
Column: C18, 5 µm. 21.2×150 mm or C18, 5 µm 21×250 or C14 21×150
Column temperature: Room Temperature
Flow rate: 20.0 mL/min
Mobile Phases: A=Water+0.05% TFA B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Preparation 1

4-(4-bromo-phenyl)-2-(S)-pyrrolidin-2-yl-1H-imidazole

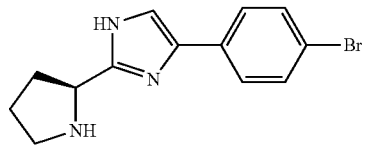 [SMILES: Brc1ccc(-c2c[nH]c([C@@H]3CCCN3)n2)cc1]

(a) 2-Bromo-1-(4-bromo-phenyl)-ethanone

Bromine (80 g, 500 mmol) was added dropwise to a solution of 1-(4-bromo-phenyl)-ethanone (100 g, 500 mmol) in dichloromethane (1500 mL) at ambient temperature. The reaction mixture was stirred for 3 h and then concentrated. The residue was washed with dichloromethane (100 mL) to give the crude title compound (120 g, 86% yield) as a white solid. $^1$H NMR (CDCl$_3$, 400 MHz) δ (ppm): 7.78 (d, J=8.4 Hz, 2H), 7.57 (d, J=8.4 Hz, 2H), 4.32 (s, 2H).

(b) (S)-Pyrrolidine-1,2-dicarboxylic acid 2-[2-(4-bromo-phenyl)-2-oxo-ethyl]ester 1-tert-butyl ester Diisopropylethylamine (67 g, 518 mmol) was added dropwise to a solution of the product of the previous step (120 g, 432 mmol) and (S)-pyrrolidine-1,2-dicarboxylic acid 1-tert-butyl ester (L-Boc proline) (102 g, 475 mmol) in acetonitrile (2 L) at room temperature. The reaction mixture was stirred overnight and concentrated to dryness. The residue was dissolved in ethyl acetate (2 L) and washed with water (2 L). The organic layer was dried over sodium sulfate and concentrated to give crude title compound (178 g, 100% yield).

(c) (S)-2-[4-(4-Bromo-phenyl)-1H-imidazol-2-yl]-pyrrolidine-1-carboxylic acid tert-butyl ester A solution of the product of the previous step (178 g, 432 mmol) and ammonium acetate (500 g, 6.5 mol) in toluene (2

L) was heated at reflux overnight. The solvent was removed and the residue was dissolved in ethyl acetate (2 L) and washed with water (2 L). The organic layer was dried over sodium sulfate and concentrated. The residue was purified by silica gel column chromatography in 1:3 petroleum ether: ethyl acetate to give the title compound (120 g, 71% yield) as a yellow solid. $^1$H NMR (CDCl$_3$, 400 MHz) δ (ppm): 7.56 (s, 1H), 7.39 (d, J=8.0 Hz, 2H), 7.24 (m, 1H), 7.14 (s, 1H), 4.88 (m, 1H), 3.33 (m, 2H), 2.94 (s, 1H), 2.07 (m, 2H), 1.88 (m, 1H), 1.42 (s, 9H).

(d) 4-(4-Bromo-phenyl)-2-(S)-pyrrolidin-2-yl-1H-imidazole

To a solution of (S)-2-[4-(4-bromo-phenyl)-1H-imidazol-2-yl]-pyrrolidine-1-carboxylic acid tert-butyl ester (3 g, 7.6 mmol) in methanol (3 mL) was added 4N HCl in methanol (60 mL) at 0° C. The reaction mixture was stirred for 2 h and then concentrated to give crude hydrochloride salt of the title compound (2.51 g 100% yield) as a yellow solid.

Preparation 2

(S)-2-Methoxycarbonylamino-3-methyl-butyric acid

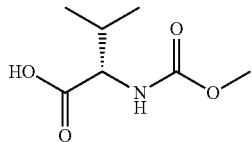

Methylchloroformate (14.5 mL, 0.188 mol) was added over 15 min to a cooled (0-6° C.) mixture of (S)-2-amino-3-methyl-butyric acid (20.0 g, 0.171 mol), NaOH (6.80 g, 0.171 mol) and sodium carbonate (18.1 g, 0.171 mol) in water (200 mL). The cooling bath was removed and the mixture was stirred at ambient temperature overnight. Conc. aqueous HCl (30 mL) was added to the reaction mixture to adjust pH to ~1. A solid formed and the mixture was stirred for 90 min. The mixture was filtered and the solid was dried overnight under reduced pressure at 40° C. t to provide the title intermediate (27.8 g, 93% yield). $^1$H NMR (CD$_3$OD, 400 MHz) δ (ppm) 4.87 (br. s, 2H), 4.05 (d, J=5.49, 1 H), 3.65 (s, 3 H), 2.25-2.05 (m, 1 H), 0.98 (d, J=6.87, 3 H), 0.94 (d, J=6.87, 3 H).

Preparation 3

((S)-1-{(S)-2-[4-(4-Bromo-phenyl)-1H-imidazol-2-yl]-pyrrolidine-1-carbonyl}-2-methyl-propyl)-carbamic acid methyl ester

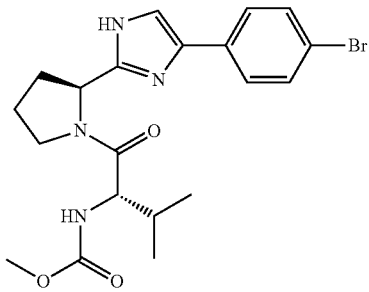 [SMILES: COC(=O)N[C@H](C(=O)N1CCC[C@H]1c1nc(-c2ccc(Br)cc2)c[nH]1)C(C)C]

Triethylamine (2.3 g, 11.4 mmol) was added to a solution of 4-(4-bromo-phenyl)-2-(S)-pyrrolidin-2-yl-1H-imidazole hydrochloride (2 g, 11.4 mol), (S)-2-methoxycarbonylamino-3-methyl-butyric acid (2.5 g, 7.6 mmol), and HATU (4.3 g, 11.4 mmol) in dimethylformamide (50 mL) at 0° C. under nitrogen. The reaction mixture was stirred at room temperature overnight and treated with ethyl acetate (100 mL) and water (1000 mL). The organic layer was washed with water (2×100 mL) and brine (100 mL), dried over anhydrous sodium sulfate and concentrated. The residue was purified by silica gel column chromatography in 1:1 petroleum ether: ethyl acetate to give the title compound (2.5 g 74% yield) as a yellow solid. $^1$H NMR (d$_6$-DMSO, 400 MHz) δ (ppm) 7.63 (d, J=8.8 Hz, 2H), 7.54 (m, 1H), 7.47 (m, 2H), 7.26 (d, J=8.4 Hz, 1H), 5.03 (m, 1H), 4.02 (t, J=8.4 Hz, 1H), 3.76 (m, 2H), 3.51 (s, 3H), 2.10 (m, 2H), 1.93 (m, 3H), 0.85 (d, J=6.8 Hz, 3H), 0.81 (d, J=6.8 Hz, 3H).

Preparation 4

[(S)-2-Methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester

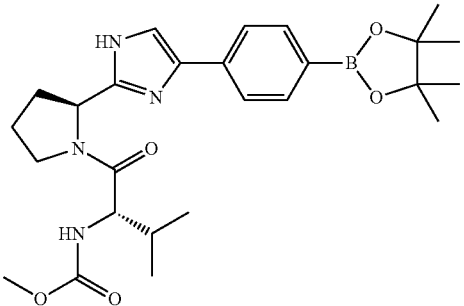

To a solution of ((S)-1-{(S)-2-[4-(4-bromo-phenyl)-1H-imidazol-2-yl]-pyrrolidine-1-carbonyl}-2-methyl-propyl)-carbamic acid methyl ester (50 g, 0.11 mol), 4,4,5,5,4',4',5',5'-octamethyl-[2,2']bi[[1,3,2]dioxaborolanyl](57 g, 0.22 mol) and potassium acetate (108 g, 1.1 mol) in dioxane (1000 mL) was added Pd(dppf)Cl$_2$.CH$_2$Cl$_2$ (4.5 g, 5.5 mmol) under nitrogen. The reaction mixture was stirred at 85° C. overnight and then ethyl acetate (100 mL) and water (1000 mL) were added. The organic layer was washed with water (2×1000 mL) and brine (1000 mL), dried over anhydrous Na$_2$SO$_4$ and concentrated. The residue was purified by silica gel column chromatography (1:1 petroleum ether:ethyl acetate) to give the title compound (22.5 g) as a yellow solid. $^1$H NMR (CDCl$_3$, 400 MHz) δ (ppm) 7.71 (m, 3H), 7.32 (m, 1H), 7.19 (m, 1H), 5.56 (m, 1H), 5.18 (m, 1H), 4.23 (m, 1H), 3.73 (m, 1H), 3.61 (s, 3H), 3.55 (m, 1H), 2.95 (m, 1H), 2.38 (s, 1H), 2.13 (m, 1H), 2.02 (m, 1H), 1.89 (m, 2H), 1.22 (s, 12H), 0.79 (d, 6H).

Preparation 5

((S)-1-{(S)-2-[4-(4'-Amino-2'-trifluoromethoxy-biphenyl-4-yl)-1H-imidazol-2-yl]-pyrrolidine-1-carbonyl}-2-methyl-propyl)-carbamic acid methyl ester

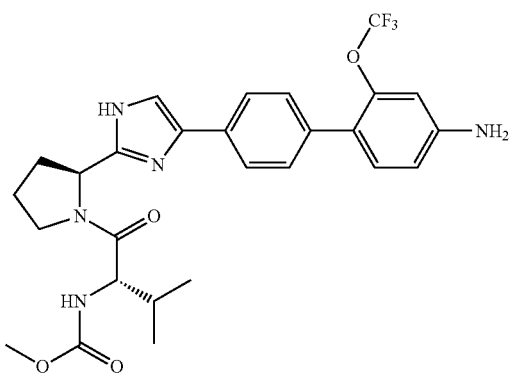 [SMILES: COC(=O)N[C@H](C(=O)N1CCC[C@H]1c1nc(-c2ccc(-c3ccc(N)cc3OC(F)(F)F)cc2)c[nH]1)C(C)C]

To a solution of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (1.80 g, 3.63 mmol) and 4-bromo-3-trifluoromethoxy-phenylamine (1.00 g, 3.90 mmol) dissolved in toluene (5.4 mL) and water (2.7 mL) was added potassium carbonate (2.50 g, 18.1 mmol). The reaction mixture was sparged with nitrogen. Tetrakis(triphenylphosphine)-palladium(0) (0.21 g, 0.18 mmol) was added and the reaction mixture was sparged with nitrogen and heated at 100° C. in a sealed tube overnight, diluted in ethyl acetate (100 mL) and washed with water, brine. The organic layer was dried over sodium sulfate, filtered, and concentrated to produce a red paste (6.5 g), which was purified by silica gel chromatography (120 g silica, 0-3% MeOH/DCM) to provide the title intermediate (1.05 g) and a second fraction which was purified by reverse phase HPLC to provide the di-TFA salt of the title intermediate (800 mg). (Total yield 80%).

Preparation 6

Cyclopropyl-[4-((S)-2-methyl-piperazin-1-yl)-piperidin-1-yl]-methanone

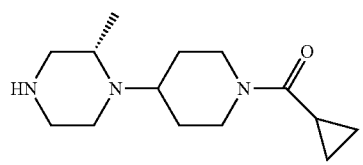 [SMILES: C[C@H]1CNCCN1C1CCN(C(=O)C2CC2)CC1]

To a mixture of (S)-3-methyl-piperazine-1-carboxylic acid tert-butyl ester (220 mg, 1.1 mmol) and 1-(cyclopropylcarbonyl)piperidin-4-one (150 mg, 0.9 mmol) in methanol (5 mL, 120 mmol) was added slowly trifluoroacetic acid (6.9 μL, 0.09 mmol) followed by sodium cyanoborohydride (56 mg, 0.9 mmol). The reaction mixture was stirred overnight at RT, concentrated by rotary evaporation, washed with 1 N NaOH (20 mL) and extracted with EtOAc (3×15 mL). Combined organic fractions were washed with brine, dried with sodium sulfate, and concentrated by rotary evaporation to afford a white solid (320 mg). A mixture of the white solid in 4 M HCl in 1,4-dioxane (5 mL) was stirred at RT for 30 min and concentrated to provide the di-HCl salt of the title intermediate (180 mg, 62% yield) as a white suspension.

Preparation 7

(2S,4S)-2-[4-(4-Bromo-phenyl)-1H-imidazol-2-yl]-4-methyl-pyrrolidine-1-carboxylic acid tert-butyl ester

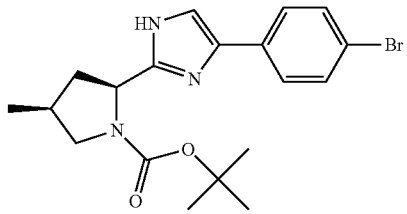 [SMILES: C[C@H]1C[C@@H](c2nc(-c3ccc(Br)cc3)c[nH]2)N(C(=O)OC(C)(C)C)C1]

(a) (S)-Pyrrolidine-1,2-dicarboxylic acid 2-[2-(4-bromo-phenyl)-2-oxo-ethyl]ester 1-tert-butyl ester To a mixture of p-bromophenacyl bromide (242 mg, 0.87 mmol) in DCM (1.5 mL) and DMA (1.5 mL), under nitrogen, was added (2S,4S)-4-methyl-pyrrolidine-1,2-dicarboxylic acid 1-tert-butyl ester (200 mg, 0.87 mmol) and N,N-diisopropylethylamine (531.8 μL, 3.05 mmol) and the resulting mixture was stirred at 35° C. for 3 h, concentrated under vacuum, dissolved in DCM (30 mL), and washed with water (2×5 ml). The organic layer was dried over magnesium sulfate, filtered, and concentrated under vacuum to provide the title intermediate.

(b) (2S,4S)-2-[4-(4-Bromo-phenyl)-1H-imidazol-2-yl]-4-methyl-pyrrolidine-1-carboxylic acid tert-butyl ester The product of the previous step was dissolved in toluene (20.0 mL), ammonium acetate (1.345 g, 17.45 mmol) was added, and resulting mixture was stirred at 95° C. overnight, concentrated and purified by silica gel chromatography (24 g silica, 0-80% EtOAc/hexanes)) to give the title product (265 mg) (m/z): $[M+H]^+$ calcd for $C_{19}H_{24}BrN_3O_2$ 406.11, 408.11 found 408.5.

Preparation 8

5-(4-Bromo-phenyl)-2-((2S,4S)-4-methyl-pyrrolidin-2-yl)-1H-imidazole

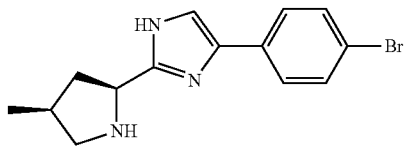 [SMILES: C[C@@H]1CN[C@H](c2nc(-c3ccc(Br)cc3)c[nH]2)C1]

A mixture of (2S,4S)-2-[4-(4-bromo-phenyl)-1H-imidazol-2-yl]-4-methyl-pyrrolidine-1-carboxylic acid tert-butyl ester (265 mg, Preparation 7) and 4 M HCl in 1,4-dioxane (2.0 mL) was left for 1 h and then concentrated by rotary evaporation to provide the di-HCl salt of the title intermediate (224 mg, 68% yield). (m/z): [M+H]+ calcd for $C_{14}H_{16}BrN_3$ 306.06, 308.06 found 306.3.

Preparation 9

((S)-1-{(2S,4S)-2-[5-(4-Bromo-phenyl)-1H-imidazol-2-yl]-4-methyl-pyrrolidine-1-carbonyl}-2-methyl-propyl)-carbamic acid methyl ester

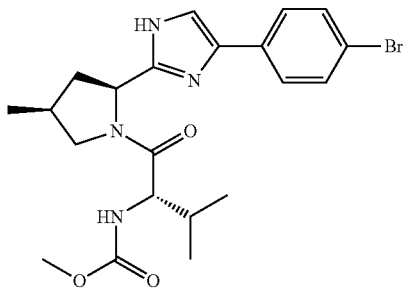 [SMILES: COC(=O)N[C@H](C(=O)N1C[C@@H](C)C[C@H]1c1nc(-c2ccc(Br)cc2)c[nH]1)C(C)C]

A mixture of (S)-2-methoxycarbonylamino-3-methyl-butyric acid (103 mg, 0.59 mmol, Preparation 2) and HATU (270 mg, 0.71 mmol) were stirred in DMA (2 mL) for 10 min and then 5-(4-bromo-phenyl)-2-((2S,4S)-4-methyl-pyrrolidin-2-yl)-1H-imidazole 2 HCl (224 mg, 0.59 mmol, Preparation 8) and N,N-diisopropylethylamine (0.31 mL, 1.8 mmol) were added. The resulting mixture was stirred at RT overnight, diluted with ethyl acetate (50 mL), and washed with water (2×5 mL). The organic layer was dried over magnesium sulfate, filtered, concentrated and purified by silica gel chromatography (0-100% EtOAc/hexanes)). Fractions with desired product were combined and concentrated to give the title compound (183 mg, 66% yield) (m/z): [M+H]+ calcd for $C_{21}H_{27}BrN_4O_3$ 463.13, 465.12 found 465.3.

Preparation 10

[(S)-2-Methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester

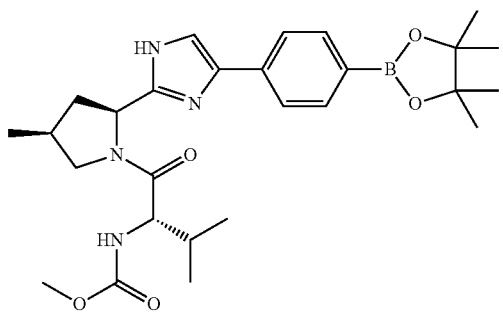

To a solution of ((S)-1-{(2S,4S)-2-[4-(4-bromo-phenyl)-1H-imidazol-2-yl]-4-methyl-pyrrolidine-1-carbonyl}-2-methyl-propyl)-carbamic acid methyl ester (183 mg, 0.39 mmol; Preparation 9) and 4,4,5,5,4',4',5',5'-octamethyl-[2,2']bi[[1,3,2]dioxaborolanyl] (120 mg, 0.47 mmol) in 1,4-dioxane (5 mL) was added potassium acetate (56 mg, 0.59 mmol). The resulting mixture was sparged with nitrogen, Pd(dppf)Cl₂.CH₂Cl₂ (27 mg, 0.033 mmol) was added, and the reaction mixture was capped and heated at 100° C. overnight. The reaction was cooled to RT and partitioned between EtOAc (50 mL) and water (10 mL). The organic layer was washed with water (5 mL), brine (2 mL), dried over magnesium sulfate, filtered, and concentrated to give a dark-brown oil, which was purified by silica gel chromatography (24 g silica gel, 0-100% EtOAc/hexanes). Fractions with desired product were combined and dried to give the title compound (94 mg, 47% yield) as a white foam. (m/z): [M+H]+ calcd for $C_{27}H_{39}BN_4O_5$ 511.30 found 511.7.

Preparation 11

4-Bromo-2-chloro-5-trifluoromethoxy-phenylamine

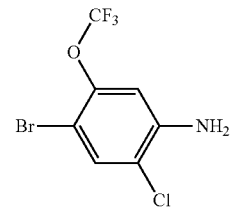 [SMILES: Nc1cc(OC(F)(F)F)c(Br)cc1Cl]

To a mixture of 4-bromo-3-trifluoromethoxy-phenylamine (2.0 g, 7.8 mmol) in ACN (60 mL) was slowly added a solution of N-chlorosuccinimide (1.0 g, 7.8 mmol) in ACN (40 mL). The reaction mixture was heated to at 60° C. overnight and extracted with ethyl acetate/water. The organic layer was dried over sodium sulfate and purified by silica gel chromatography (40 g silica, 100% hexanes to 10% EtOAc:hexanes) to produce the desired product as an orange colored oil (1.4 g, 64% yield).

Preparation 12

4-piperazin-1-yl-piperidine-1-carboxylic acid tert-butyl ester

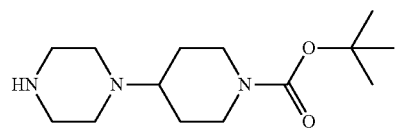 [SMILES: CC(C)(C)OC(=O)N1CCC(N2CCNCC2)CC1]

(a) 4-(1-tert-Butoxycarbonyl-piperidin-4-yl)-piperazine-1-carboxylic acid benzyl ester A mixture of piperazine-1-carboxylic acid benzyl ester (6.6 g, 29.96 mmol) and 4-oxo-piperidine-1-carboxylic acid tert-butyl ester in dichloroethane (150 mL) containing two drops of acetic acid was stirred at RT for 1 h and then sodium triacetoxyborohydride (19.05 g, 89.89 mmol) was added in portions. The reaction mixture was stirred at RT overnight, water (150 mL) was added, and the reaction mixture was stirred at RT for 2 h. The reaction mixture was extracted with DCM (4×30 mL). Combined organic layers were dried over sodium sulfate, filtered, concentrated under reduced pressure, and purified by silica gel chromatography (20-30% EtOAc/ petroleum ether) to provide the title intermediate (9 g, 74% yield) as a colorless oil. (m/z): $[M+H]^+$ calcd for $C_{22}H_{33}N_3O_4$ 404.25, found 404.3.

(b) 4-piperazin-1-yl-piperidine-1-carboxylic acid tert-butyl ester

The product of the previous step (9 g, 22.30 mmol) and palladium on carbon (1 g) in IPA (150 mL) were stirred at RT under hydrogen (50 psi) overnight, filtered, and the solvent was removed under vacuum to provide the title intermediate (5.57 g, 93% yield) as a colorless solid. (m/z): $[M+H]^+$ calcd for $C_{14}H_{27}N_3O_2$ 270.21, found 270.2. $^1$H NMR (MeOD, 400 MHz): δ (ppm) 4.11 (d, J=13.5 Hz, 2H), 2.98-2.64 (m, 11H), 1.85 (d, J=12.4 Hz, 2H), 1.44 (s, 9H), 1.44-1.34 (m, 2H).

Preparation 13

4-[4-(4-Bromo-2-chloro-5-trifluoromethoxy-phenylcarbamoyl)-piperazin-1-yl]-piperidine-1-carboxylic acid tert-butyl ester

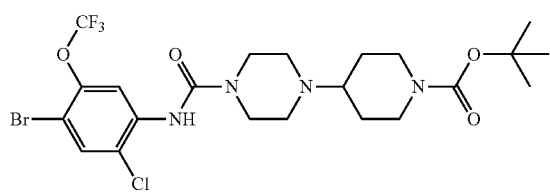 [SMILES: CC(C)(C)OC(=O)N1CCC(N2CCN(C(=O)Nc3cc(OC(F)(F)F)c(Br)cc3Cl)CC2)CC1]

To a solution of 4-bromo-2-chloro-5-trifluoromethoxyphenylamine (0.55 g, 1.90 mmol) in DCM (4.9 mL) was added CDI (0.34 g, 2.09 mmol). The reaction solution was stirred at RT overnight and then 4-piperazin-1-yl-piperidine-1-carboxylic acid tert-butyl ester (0.56 g, 2.09 mmol; Preparation 12) was added and the reaction mixture was stirred for 30 min at RT, concentrated under vacuum and purified by silica gel chromatography (0-5% MeOH/DCM). Pure fractions were combined and concentrated under vacuum to provide the title intermediate (0.67 g, 60% yield) as a white foam. (m/z): $[M+H]^+$ calcd for $C_{22}H_{29}BrClF_3N_4O_4$ 585.1 found 584.6.

Preparation 14

4-[4-(5-Chloro-4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester

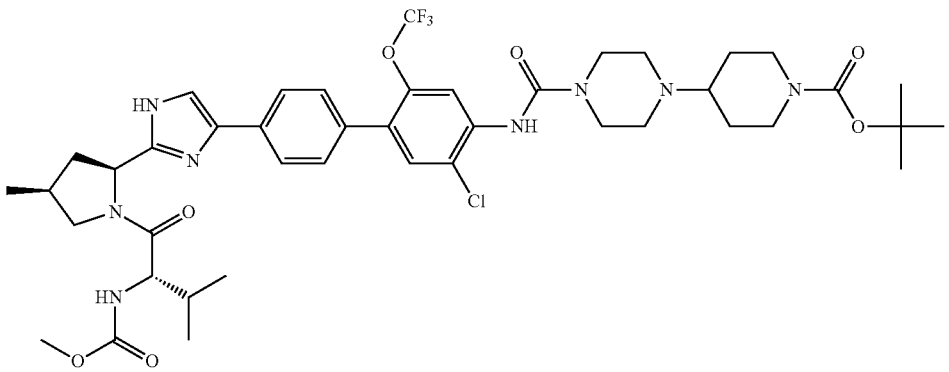 [SMILES: COC(=O)N[C@H](C(=O)N1C[C@@H](C)C[C@H]1c1nc(-c2ccc(-c3cc(Cl)c(NC(=O)N4CCN(C5CCN(C(=O)OC(C)(C)C)CC5)CC4)cc3OC(F)(F)F)cc2)c[nH]1)C(C)C]

A solution of [(S)-2-methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester (0.12 g, 0.24 mmol), 4-[4-(4-bromo-2-chloro-5-trifluoromethoxy-phenylcarbamoyl)-piperazin-1-yl]-piperidine-1-carboxylic acid tert-butyl ester (0.138 g, 0.235 mmol; Preparation 13) in 1,4-dioxane (1.84 mL) and water (0.28 mL) was degassed with nitrogen for 20 min and then $Pd_2(dba)_3$ (32.3 mg, 0.0353 mmol) and 2-dicyclohexylphosphino-2',4',6'-triisopropylbiphenyl (0.112 g, 0.235 mmol) were added and the reaction was degassed with nitrogen for a further 15 min. The resulting solution was heated at 90° C. for 60 h, cooled to RT and diluted with EtOAc (3 mL). The layers were separated and the aqueous layer was washed with EtOAc (3×3 mL). The combined organic extracts were washed with water and brine, dried over $MgSO_4$, filtered, concentrated, and purified by reverse phase HPLC. Fractions were combined and lyophilised overnight to provide the di-TFA salt of the title intermediate (65 mg, 25% yield).

Preparation 15

((S)-1-{(2S,4S)-2-[4-(4-Bromo-phenyl)-5-chloro-1H-imidazol-2-yl]-4-methyl-pyrrolidine-1-carbonyl}-2-methyl-propyl)-carbamic acid methyl ester

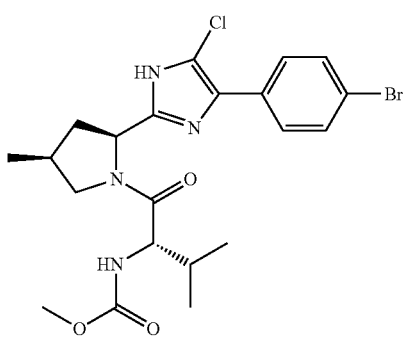

A mixture of ((S)-1-{(2S,4S)-2-[4-(4-bromo-phenyl)-1H-imidazol-2-yl]-4-methyl-pyrrolidine-1-carbonyl}-2-methyl-propyl)-carbamic acid methyl ester (175 mg, 0.38 mmol) and N-chlorosuccinimide (202 mg, 1.51 mmol) in acetonitrile (4 mL) was stirred at RT overnight. The reaction mixture was concentrated by rotary evaporation and purified by silica gel chromatography (24 g silica, 0-100% hexanes/EtOAc) to provide the title intermediate (208 mg) as a brown solid. (m/z): [M+H]$^+$ calcd for $C_{21}H_{27}BrClN_4O_3$ 497.09, found 497.4.

Preparation 16

4-[4-(4-Bromo-3-trifluoromethoxy-phenylcarbamoyl)-piperazin-1-yl]-piperidine-1-carboxylic acid tert-butyl ester

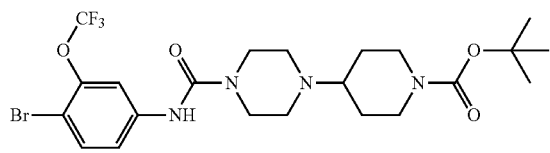

To a solution of 4-bromo-3-trifluoromethoxy-phenylamine (500 mg, 2 mmol) in DCM (5 mL) was added N,N-carbonyldiimidazole (348 mg, 2.15 mmol). The reaction mixture was stirred at RT overnight and then 4-piperazin-1-yl-piperidine-1-carboxylic acid tert-butyl ester (579 mg, 2.15 mmol, Preparation 12) was added and the reaction mixture was stirred at RT for 15 min, and concentrated by rotary evaporation and purified by silica gel chromatography (80 g silica, 0-10% MeOH/DCM) to provide the title intermediate (776 mg, 70% yield) as a yellow powder. (m/z): [M+H]$^+$ calcd for $C_{22}H_{30}BrF_3N_4O_4$ 551.14, found 551.3.

Preparation 17

4-{4-[4-(4,4,5,5-Tetramethyl-1,3,2-dioxaborolan-2-yl)-3-trifluoromethoxy-phenylcarbamoyl]-piperazin-1-yl}-piperidine-1-carboxylic acid tert-butyl ester

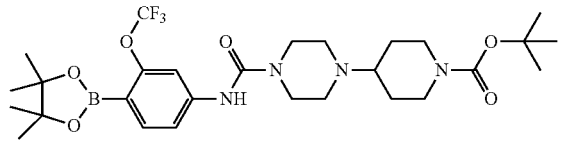 [SMILES: CC(C)(C)OC(=O)N1CCC(N2CCN(C(=O)Nc3ccc(B4OC(C)(C)C(C)(C)O4)c(OC(F)(F)F)c3)CC2)CC1]

To a solution of 4-[4-(4-bromo-3-trifluoromethoxy-phenylcarbamoyl)-piperazin-1-yl]-piperidine-1-carboxylic acid tert-butyl ester (200 mg, 0.4 mmol, Preparation 16) and 4,4,5,5,4',4',5',5'-octamethyl-[2,2']bi[[1,3,2]dioxaborolanyl] (115 mg, 0.45 mmol), potassium acetate (53.4 mg, 0.54 mmol) was added 1,4-dioxane (4 mL, 50 mmol). The resulting mixture was sparged with nitrogen, Pd(dppf)Cl$_2$.CH$_2$Cl$_2$ (88.9 mg, 0.11 mmol) was added, and the reaction mixture was heated at 100° C. overnight, and then filtered through a Celite® pad, which was washed with methanol. The eluent was concentrated, diluted in a minimal amount of DCM and purified via silica gel chromatography (40 g silica, 0-100% EtOAc/hexanes, flushed with 100% EtOAc) to provide the title intermediate (70 mg, 30% yield) as a brown solid. (m/z): [M+H]$^+$ calcd for $C_{28}H_{42}BF_3N_4O_6$ 599.31, found 599.5.

Preparation 18

{(S)-1-[(2S,4S)-2-(5-Chloro-4-{4'-[(4-piperidin-4-yl-piperazine-1-carbonyl)-amino]-2'-trifluoromethoxy-biphenyl-4-yl}-1H-imidazol-2-yl)-4-methyl-pyrrolidine-1-carbonyl]-2-methyl-propyl}-carbamic acid methyl ester

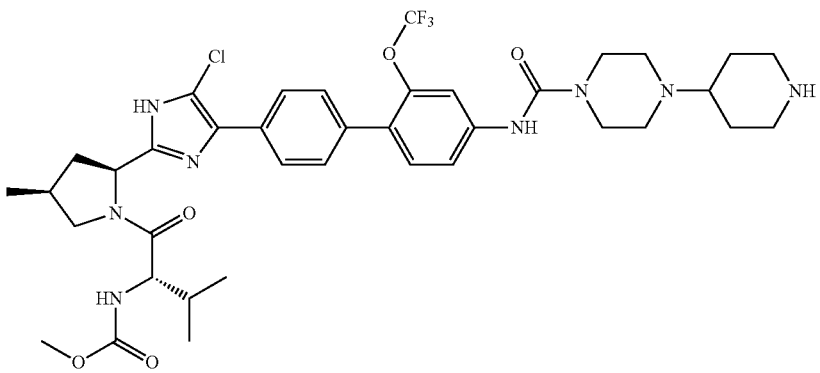 [SMILES: COC(=O)N[C@H](C(=O)N1C[C@@H](C)C[C@H]1c1nc(-c2ccc(-c3ccc(NC(=O)N4CCN(C5CCNCC5)CC4)cc3OC(F)(F)F)cc2)c(Cl)[nH]1)C(C)C]

(a) 4-[4-(4'-{5-Chloro-2-[(2S,4S)-1-((S)-2-methoxy-carbonylamino-3-methyl-butyryl)-4-methyl-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester A mixture of 4-{4-[4-(4,4,5,5-tetramethyl-1,3,2-dioxaborolan-2-yl)-3-trifluoromethoxy-phenylcarbamoyl]-piperazin-1-yl}-piperidine-1-carboxylic acid tert-butyl ester (70 mg, 0.12 mmol; Preparation 17), ((S)-1-{(2S,4S)-2-[4-(4-bromo-phenyl)-5-chloro-1H-imidazol-2-yl]-4-methyl-pyrrolidine-1-carbonyl}-2-methyl-propyl)-carbamic acid methyl ester (58 mg, 0.12 mmol; Preparation 15), and sodium bicarbonate (49 mg, 0.58 mmol) in 1,4-dioxane (2 mL) and water (0.5 mL) was purged with nitrogen and then 2-dicyclohexylphosphino-2',4',6'-triisopropylbiphenyl (Xphos) (56 mg, 0.12 mmol) and $Pd_2(dba)_3$ (21 mg, 0.023 mmol) were added. The reaction mixture was heated at 100° C. overnight, concentrated by rotary evaporation, dissolved in 1:1 acetic acid:water (4 mL), purified by reverse phase HPLC, and lyophilized to provide the TFA salt of the title intermediate (20 mg) as a yellow solid. (m/z): [M+H]$^+$ calcd for $C_{43}H_{56}ClF_3N_8O_7$ 889.39, found 889.4.

(b) {(S)-1-[(2S,4S)-2-(5-Chloro-4-{4'-[(4-yl-piperidin-4-yl-piperazine-1-carbonyl)-amino]-2'-trifluoromethoxy-biphenyl-4-yl}-1H-imidazol-2-yl)-4-methyl-pyrrolidine-1-carbonyl]-2-methyl-propyl}-carbamic acid methyl ester The product of the previous step was diluted in 4 M HCl in 1,4-dioxane (3 mL), stirred at RT, and concentrated to provide the tri-HCl salt of the title intermediate (20 mg, yield 20%) as a yellow solid. (m/z): [M+H]$^+$ calcd for $C_{38}H_{48}ClF_3N_8O_5$ 789.34, found 789.3.

Preparation 19

((2S,4S)-2-[4-(4-Bromo-phenyl)-5-fluoro-1H-imidazol-2-yl]-4-methyl-pyrrolidine-1-carboxylic acid tert-butyl ester

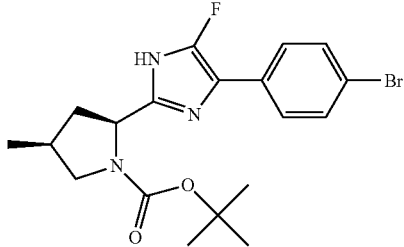 [SMILES: C[C@H]1C[C@@H](c2nc(-c3ccc(Br)cc3)c(F)[nH]2)N(C(=O)OC(C)(C)C)C1]

A solution of (2S,4S)-2-[4-(4-bromo-phenyl)-1H-imidazol-2-yl]-4-methyl-pyrrolidine-1-carboxylic acid tert-butyl ester (500 mg, 1.23 mmol) and 1-fluoro-4-hydroxy-1,4-diazoniabicyclo[2.2.2]octane bis(tetrafluoroborate) (436 mg, 1.36 mmol) in DMF (20 mL) was stirred at RT for 1 h, concentrated by rotary evaporation, and purified by silica gel chromatography (0-100% EtOAc/hexanes with 1% $Et_3N$). Desired fractions were collected and concentrated to provide the title intermediate (180 mg, 35% yield). (m/z): [M+H]$^+$ calcd for $C_{19}H_{24}BrFN_3O_2$ 424.10, 426.09 found 424.1.

Preparation 20

((S)-1-{(2S,4S)-2-[4-(4-Bromo-phenyl)-5-fluoro-1H-imidazol-2-yl]-4-methyl-pyrrolidine-1-carbonyl}-2-methyl-propyl)-carbamic acid methyl ester

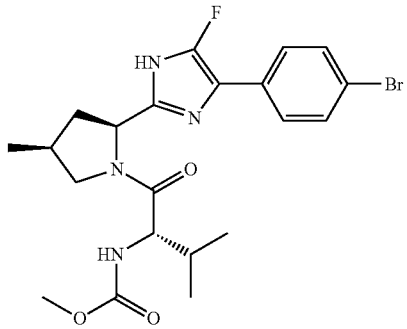 [SMILES: COC(=O)N[C@H](C(=O)N1C[C@@H](C)C[C@H]1c1nc(-c2ccc(Br)cc2)c(F)[nH]1)C(C)C]

A solution of (2S,4S)-2-[4-(4-bromo-phenyl)-5-fluoro-1H-imidazol-2-yl]-4-methyl-pyrrolidine-1-carboxylic acid tert-butyl ester (180 mg, 0.42 mmol; Preparation 19) in 4 M HCl in 1,4-dioxane (0.53 mL) and 1,4-dioxane (0.9 mL) was stirred at RT for 30 min and concentrated by rotary evaporation.

The crude material was dissolved in DMA (5.54 g) and then (S)-2-methoxycarbonylamino-3-methyl-butyric acid (89.2 mg, 0.51 mmol; Preparation 2), HCTU (0.21 g, 0.51 mmol), and DIPEA (0.27 g, 2.12 mmol) were added. The reaction mixture was stirred at RT overnight, concentrated by rotary evaporation, and purified by silica gel chromatography (0-100% EtOAc/hexanes). Desired fractions were collected and concentrated by rotary evaporation to provide the title intermediate (200 mg, 98% yield). (m/z): [M+H]$^+$ calcd for $C_{21}H_{26}BrFN_4O_3$ 481.12, 483.12 found 480.7.

Preparation 21

4-[4-(4'-{5-Fluoro-2-[(2S,4S)-1-((S) 2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester

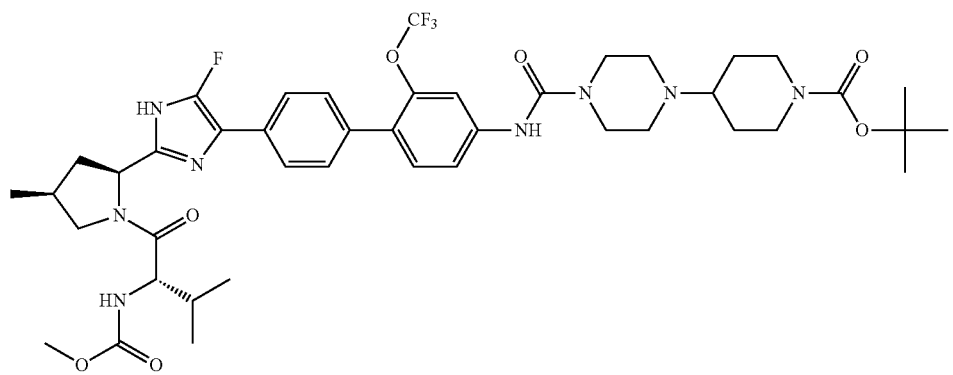 [SMILES: COC(=O)N[C@H](C(=O)N1C[C@@H](C)C[C@H]1c1nc(-c2ccc(-c3ccc(NC(=O)N4CCN(C5CCN(C(=O)OC(C)(C)C)CC5)CC4)cc3OC(F)(F)F)cc2)c(F)[nH]1)C(C)C]

A solution of 4-{4-[4-(4,4,5,5-tetramethyl-1,3,2-dioxaborolan-2-yl)-3-trifluoromethoxy-phenylcarbamoyl]-piperazin-1-yl}-piperidine-1-carboxylic acid tert-butyl ester (31.1 mg, 0.05 mmol), ((S)-1-{(2S,4S)-2-[4-(4-bromo-phenyl)-5-fluoro-1H-imidazol-2-yl]-4-methyl-pyrrolidine-1-carbonyl}-2-methyl-propyl)-carbamic acid methyl ester (25 mg, 0.05 mmol; Preparation 20) and sodium bicarbonate (22.7 mg, 0.27 mmol) in 1,4-dioxane (2.11 mL) and water (0.10 mL), was degassed with nitrogen for 15 min and then $Pd_2(dba)_3$ (9.51 mg, 0.01 mmol) and 2-dicyclohexylphosphino-2',4',6'-triisopropylbiphenyl (24.8 mg, 0.05 mmol) were added and the purple solution was degassed with nitrogen for a further 15 min. The solution was capped and heated at 90° C. for 12 h, concentrated under vacuum, dissolved in 1:1 acetic acid:water (5 mL), filtered through a pad of Celite®, and purified by reverse phase HPLC. Pure fractions were combined and lyophilised overnight to provide the di-TFA salt of the title intermediate (40 mg, 69% yield). (m/z): $[M+H]^+$ calcd for $C_{43}H_{56}F_4N_8O_7$ 873.42 found 873.6.

Preparation 22

(S)-3-Methyl-4-piperidin-4-yl-piperazine-1-carboxylic acid tert-butyl ester

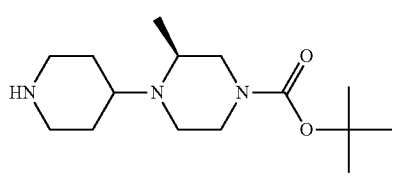 [SMILES: C[C@H]1CN(C(=O)OC(C)(C)C)CCN1C1CCNCC1]

(a) (S)-4-(1-Benzyloxycarbonyl-piperidin-4-yl)-3-methyl-piperazine-1-carboxylic acid tert-butyl ester To a solution of (S)-3-methyl-piperazine-1-carboxylic acid tert-butyl ester (1.0 g, mmol) and N-benzyloxycarbonyl-4-piperidone (1.2 g, 5 mmol) in methanol (8 mL) was added acetic acid (0.28 mL) and the solution was stirred at RT for 1 h. Sodium cyanoborohydride (310 mg, 5 mmol) was added and the reaction mixture was stirred at 45° C. overnight and then 1 N NaOH (5 mL) was added. The aqueous phase was extracted with EtOAc (3×15 mL). The combined organic extracts were washed with brine, dried over MgSO4, filtered, concentrated under vacuum, and purified by silica gel chromatography (0-5% MeOH/DCM). Pure fractions were combined and concentrated under vacuum to provide the title intermediate (0.71 g, 30% yield) as a clear oil. (m/z): $[M+H]^+$ calcd for $C_{23}H_{35}N_3O_4$ 418.26 found 418.1.

(b) (S)-3-Methyl-4-piperidin-4-yl-piperazine-1-carboxylic acid tert-butyl ester

A solution of the product of the previous step and 10% Pd/C, wet 50% (0.05:0.45:0.5, Palladium:carbon black:water, (362 mg, 0.17 mmol) in THF (7.5 mL) was purged with nitrogen. A balloon of hydrogen was bubbled through the solution for 15 min and the reaction mixture was stirred at RT under an atmosphere of hydrogen for 16 h, cooled, and filtered through a pad of Celite® and washed with THF. The crude product was purified by silica gel chromatography (10% MeOH in DCM). Desired fractions were combined and concentrated under vacuum to provide the title intermediate.

Preparation 23

(S)-4-[1-(4-Bromo-2-chloro-5-trifluoromethoxy-phenylcarbamoyl)-piperidin-4-yl]-3-methyl-piperazine-carboxylic acid tert-butyl ester

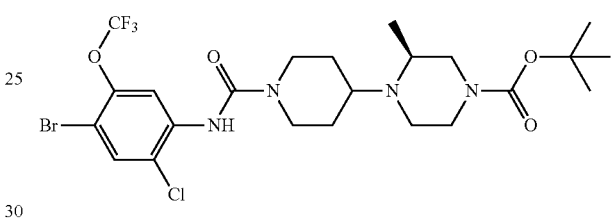

To a solution of 4-bromo-2-chloro-5-trifluoromethoxy-phenylamine (92.5 mg, 0.32 mmol) in DCM (0.82 mL) was added CDI (56.8 mg, 0.35 mmol). The reaction mixture was stirred at RT for 6 h and a solution of (S)-3-methyl-4-piperidin-4-yl-piperazine-1-carboxylic acid tert-butyl ester (99.3 mg, 0.35 mmol; Preparation 22) in DCM (1 mL) was added. The solution was concentrated under vacuum and purified by silica gel chromatography (0-5% MeOH/DCM). Product fractions were combined and concentrated under vacuum to provide the title intermediate (32 mg, 17% yield) as a clear oil. (m/z): $[M+H]^+$ calcd for $C_{23}H_{31}BrClF_3N_4O_4$ 599.12, 601.11 found 601.4.

Preparation 24

(S)-4-[1-(5-Chloro-4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-piperidin-4-yl]-3-methyl-piperazine-1-carboxylic acid tert-butyl ester

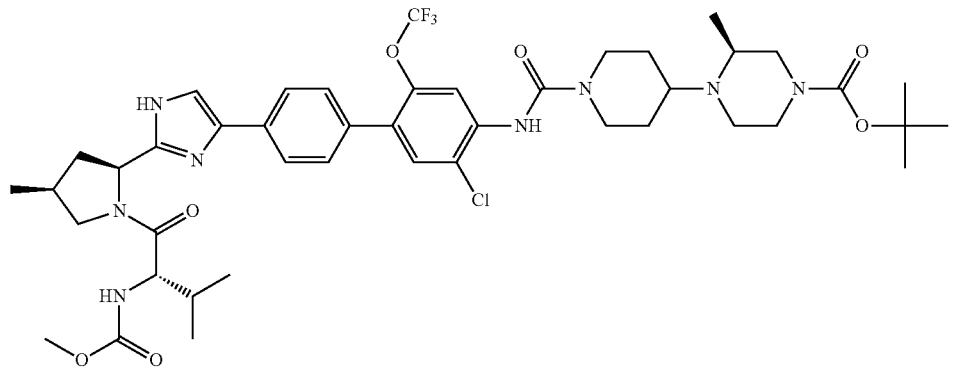 [SMILES: COC(=O)N[C@H](C(=O)N1C[C@@H](C)C[C@H]1c1nc(-c2ccc(-c3cc(Cl)c(NC(=O)N4CCC(N5CCN(C(=O)OC(C)(C)C)C[C@@H]5C)CC4)cc3OC(F)(F)F)cc2)c[nH]1)C(C)C]

A solution of [(S)-2-methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1 carbonyl)-propyl]-carbamic acid methyl ester (27.8 mg, 0.05 mmol, (S)-4-[1-(4-bromo-2-chloro-5-trifluoromethoxy-phenylcarbamoyl)-piperidin-4-yl]-3-methyl-piperazine-1-carboxylic acid tert-butyl ester (32.7 mg, 0.05 mmol; Preparation 23) and sodium bicarbonate (23.8 mg, 0.28 mmol) in 1,4-dioxane (2.2 mL) and water (0.1 mL) was degassed with nitrogen for 20 min and $Pd_2(dba)_3$ (10.0 mg, 0.01 mmol) and 2-dicyclohexylphosphino-2',4',6'-triisopropylbiphenyl (26.0 mg, 0.05 mmol) were added. The reaction mixture was purged with nitrogen for 15 min, heated at 90° C. for 60 h, concentrated, diluted with methanol, filtered through a pad of Celite®, concentrated under vacuum, and purified by reverse phase HPLC. Desired fractions were combined and lyophilised overnight to provide the di-TFA salt of the title intermediate (13 mg, 20% yield) as a white powder. (m/z): $[M+H]^+$ calcd for $C_{44}H_{58}ClF_3N_8O_7$ 903.41 found 903.6.

Preparation 25

((S)-1-{(2S,4S)-2-[5-(4-Bromo-phenyl)-1H-imidazol-2-yl]-4-methoxy-pyrrolidine-1-carbonyl}-2-methyl-propyl)-carbamic acid methyl ester

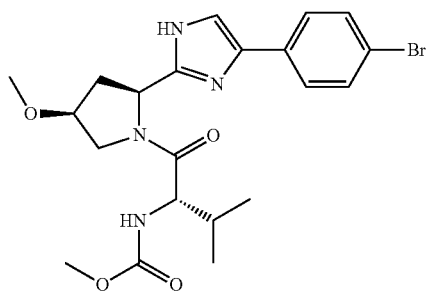 [SMILES: COC(=O)N[C@H](C(=O)N1C[C@@H](OC)C[C@H]1c1nc(-c2ccc(Br)cc2)c[nH]1)C(C)C]

(a) (2S,4S)-2-[5-(4-Bromo-phenyl)-1H-imidazol-2-yl]-4-methoxy-pyrrolidine-1-carboxylic acid tert-butyl ester To a solution of (2S,4S)-4-methoxy-pyrrolidine-1,2-dicarboxylic acid 1-tert-butyl ester (900 mg, 3.67 mmol), and p-bromophenacyl bromide (1.02 g, 3.67 mmol) in DCM (20 mL) under nitrogen, was added N,N-diisopropylethylamine (1.92 mL, 11.01 mmol). The resulting mixture was stirred at 35° C. for 3 h and concentrated under vacuum. The crude intermediate was dissolved in toluene (150 mL), ammonium acetate (5.66 g, 73.4 mmol) was added, and the resulting mixture was stirred at 95° C. overnight, cooled to RT, and washed with water (2×10 mL). The organic layer was dried over magnesium sulfate, filtered, concentrated and purified by silica gel chromatography (24 g, ethyl acetate/hexanes 0 to 60%) to give the title intermediate (1.49 g, 96% yield).

(b) 5-(4-Bromo-phenyl)-2-((2S,4S)-4-methoxy-pyrrolidin-2-yl)-1H-imidazole

The product of the previous step was treated with 4 M HCl in 1,4-dioxane (2 mL) for 1 h and concentrated by rotary evaporation to give the di-HCl salt of the title intermediate (1.40 g, 97% yield). (m/z): $[M+H]^+$ calcd for $C_{14}H_{16}BrN_3O$ 322.05, 324.05 found 324.

(c) ((S)-1-{(2S,4S)-2-[5-(4-Bromo-phenyl)-1H-imidazol-2-yl]-4-methoxy-pyrrolidine-1-carbonyl}-2-methyl-propyl)-carbamic acid methyl ester A mixture of (S)-2-methoxycarbonylamino-3-methyl-butyric acid (643 mg, 3.67 mmol) and HATU (1.67 g, 4.40 mmol) in DMA (5 mL) was stirred for 10 min, and then the product of the previous step (1.40 g, 3.54 mmol) and N,N-diisopropylethylamine (1.92 mL, 11.01 mmol) were added, and the resulting mixture was stirred at room temperature overnight, concentrated by rotary evaporation, dissolved in ethyl acetate (100 mL), and washed with water (2×10 mL). The organic layer was dried over magnesium sulfate, filtered, concentrated, and purified by silica gel chromatography (ethyl acetate/hexanes 30 to 80%) to give the title product (1.38 g, 79% yield). (m/z): $[M+H]^+$ calcd for $C_{21}H_{27}BrN_4O_4$ 479.12, 481.12 found 481.

Preparation 26

[(S)-1-((2S,4S)-4-Methoxy-2-{4-[4-(4,4,5,5-tetramethyl-1,3,2-dioxaborolan-2-yl)-phenyl]-1H-imidazol-2-yl}-pyrrolidine-1-carbonyl)-2-methyl-propyl]-carbamic acid methyl ester

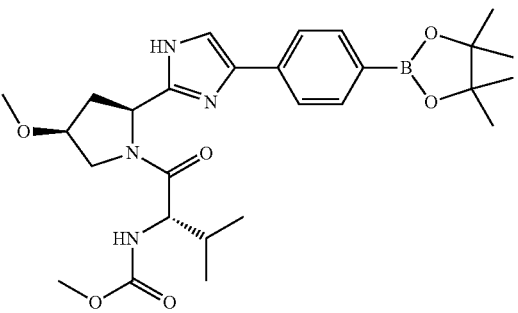

A solution of ((S)-1-{(2S,4S)-2-[5-(4-bromo-phenyl)-1H-imidazol-2-yl]-4-methoxy-pyrrolidine-1-carbonyl}-2-methyl-propyl)-carbamic acid methyl ester (1.05 g, 2.18 mmol; Preparation 25), 4,4,5,5,4',4',5',5'-octamethyl-[2,2']bi[[1,3,2]dioxaborolanyl](0.83 g, 3.27 mmol), and potassium acetate (0.39 g, 3.93 mmol) in 1,4-dioxane (5 mL) was purged with nitrogen for 5 min, then $Pd(dppf)Cl_2$ (95.80 mg, 0.13 mmol) was added, and the resulting mixture was stirred at 100° C. for 3 h, diluted with ethyl acetate (50 mL), and filtered through a pad of Celite® and silica gel. The pad was washed with ethyl acetate (150 ml); the filtrate was concentrated and purified by silica gel chromatography (ethyl acetate/hexanes 30 to 100%)

to give the title intermediate (669 mg 58% yield). (m/z): [M+H]+ calcd for $C_{27}H_{39}BN_4O_6$ 527.30 found 527.2.

Preparation 27

7-Bromo-2-((2S,4S)-4-methyl-pyrrolidin-2-yl)-3H-naphtho[1,2-d]imidazole

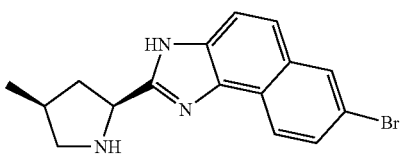 [SMILES: C[C@@H]1CN[C@H](c2nc3c(ccc4cc(Br)ccc43)[nH]2)C1]

(a) (2S,4S)-2-(2-Amino-6-bromo-naphthalen-1-yl-carbamoyl)-4-methyl-pyrrolidine-1-carboxylic acid tert-butyl ester To a solution of 6-bromo-naphthalene-1,2-diamine (2.0 g, 8.5 mmol) in DMF (150 mL) was added (2S,4S)-4-methyl-pyrrolidine-1,2-dicarboxylic acid 1-tert-butyl ester (2.14 g, 10.2 mmol), DIPEA (3.29 g, 25.5 mmol), and HATU (4.84 g, 12.7 mmol). The reaction mixture was stirred at RT overnight and extracted with EtOAc/H₂O (150 mL). The organic layer was dried over Na₂SO₄, filtered, concentrated, and purified by silica gel chromatography (2:1 EtOAc:petroleum ether) to provide the title intermediate (1.6 g)

(b) (2S,4S)-2-(7-Bromo-3H-naphtho[1,2-d]imidazol-2-yl)-4-methyl-pyrrolidine-1-carboxylic acid tert-butyl ester A solution of the product of the previous step (1.6 g, 3.57 mmol) in acetic acid (15 mL) was heated to 60° C. under nitrogen for 1 h, adjusted to pH 8-10 with 1 N NaOH, and extracted with DCM. The organic layer was dried over Na₂SO₄, filtered, and concentrated to give the title intermediate (1.5 g). (m/z): [M+H]+ calcd for $C_{21}H_{24}BrN_3O_2$ 430.11, 432.11 found 432.1.

(c) 7-Bromo-2-((2S,4S)-4-methyl-pyrrolidin-2-yl)-3H-naphtho[1,2-d]imidazole

To a solution of the product of the previous step (1.5 g, 3.5 mmol) in DCM (20 mL) was added TFA (2 mL). The mixture was stirred at RT for 5 h, adjusted to pH ~10 with 1 N NaOH (5 mL) and extracted with DCM (3×200 mL). The reaction mixture was dried over Na₂SO₄, filtered, and concentrated to give the title intermediate (1.1 g). (m/z): [M+H]+ calcd for $C_{16}H_{16}BrN_3$ 330.05, 332.05 found 330.2, 332.1.

Preparation 28

((S)-2-Methyl-1-{(2S,4S)-4-methyl-2-[7-(4,4,5,5-tetramethyl-[1,3,2]dioxaborolan-2-yl)-3H-naphtho[1,2-d]imidazol-2-yl]-pyrrolidine-1-carbonyl}-propyl)-carbamic acid methyl ester

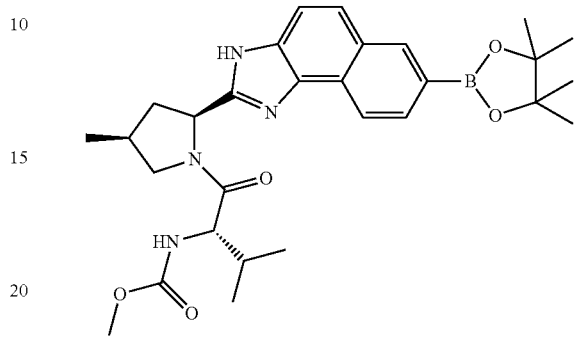

(a) {(S)-1-[(2S,4S)-2-(7-Bromo-3H-naphtho[1,2-d]imidazol-2-yl)-4-methyl-pyrrolidine-1-carbonyl]-2-methyl-propyl}-carbamic acid methyl ester To a solution of 7-bromo-2-((2S,4S)-4-methyl-pyrrolidin-2-yl)-3H-naphtho[1,2-d]imidazole (1.05 g, 3.2 mmol; Preparation 27) in DCM (20 mL) was added (S)-2-methoxycarbonylamino-3-methyl-butyric acid (672 mg, 3.84 mmol), DIPEA (825 mg, 6.4 mmol), and HATU (1.82 g, 4.8 mmol). The reaction mixture was stirred at RT for 4 h and extracted with DCM (3×250 mL). The organic layer was dried over Na₂SO₄, filtered, concentrated, and purified by silica gel chromatography (1:1 EtOAc:petroleum ether) to provide the title intermediate (1.2 g) (m/z): [M+H]+ calcd for $C_{23}H_{27}BrN_4O_3$ 487.13, 489.12 found 489.2.

(b) ((S)-2-Methyl-1-{(2S,4S)-4-methyl-2-[7-(4,4,5,5-tetramethyl-[1,3,2]dioxaborolan-2-yl)-3H-naphtho[1,2-d]imidazol-2-yl]-pyrrolidine-1-carbonyl}-propyl)-carbamic acid methyl ester To a solution of the product of the previous step (1.1 g, 2.2 mmol) in dioxane (20 mL) was added 4,4,5,5,4',4',5',5'-octamethyl-[2,2']bi[[1,3,2]dioxaborolanyl] (838 mg, 3.3 mmol), Pd(dppf)Cl₂ (161 mg, 0.22 mmol) and potassium acetate (646 mg, 6.6 mmol) at RT under nitrogen. The reaction mixture was stirred at 90° C. overnight and extracted with EtOAc/H₂O (3×150 mL). The organic layer was dried over Na₂SO₄, filtered, concentrated, and purified by silica gel chromatography (2:1 petroleum ether. EtOAc) to provide the title intermediate (450 mg. (m/z): [M+H]+ calcd for C29H39BN4O5 535.30 found 535.3. ¹H NMR: (DMSO-d₆, 400 MHz) δ(ppm) 0.64~0.86 (m, 6H), 1.09 (s, 3H), 1.31 (s, 12H), 1.85~1.90 (m, 2H), 2.20~2.38 (m, 1H), 2.51 (s, 1H), 3.31~3.33 (m, 1H), 3.51 (s, 3H), 4.01~4.07 (m, 1H), 4.11~4.16 (m, 1H), 5.09~5.10 (m, 1H), 7.15 (d, J=8.0 Hz, 2H), 7.60~7.79 (m, 3H), 8.23~8.37 (m, 2H), 12.5~13.55 (d, 1H).

Preparation 29

4-[4-(4-{2-[(2S,4S)-1-((S)-2-Methoxycarbonylamino-3-methyl-butyryl)-4-methyl-pyrrolidin-2-yl]-3H-naphtho[1,2-d]imidazol-7-yl}-3-trifluoromethoxy-phenylcarbamoyl)-piperazin-1-yl]-piperidine-1-carboxylic acid tert-butyl ester

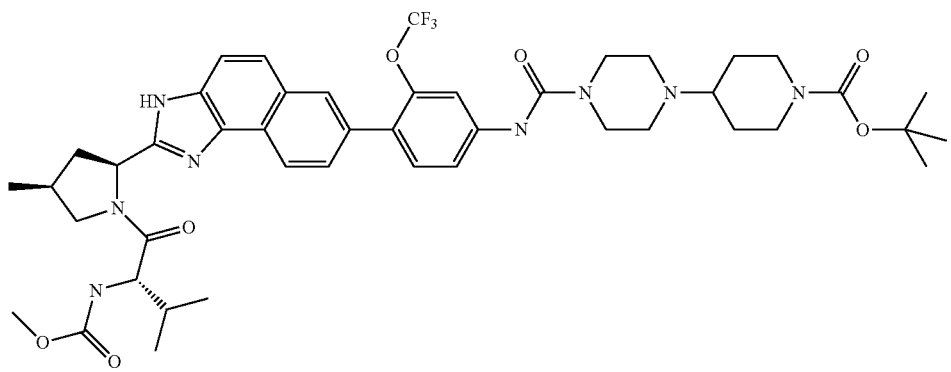 [SMILES: COC(=O)N[C@H](C(=O)N1C[C@@H](C)C[C@H]1c1nc2c(ccc3cc(-c4ccc(NC(=O)N5CCN(C6CCN(C(=O)OC(C)(C)C)CC6)CC5)cc4OC(F)(F)F)ccc32)[nH]1)C(C)C]

A solution of ((S)-2-methyl-1-{(2S,4S)-4-methyl-2-[7-(4,4,5,5-tetramethyl-1,3,2-dioxaborolan-2-yl)-3H-naphth[1,2-d]imidazol-2-yl]-pyrrolidine-1-carbonyl}-propyl)-carbamic acid methyl ester (72.7 mg, 0.13 mmol; Preparation 28), 4-[4-(4-bromo-3-trifluoromethoxy-phenylcarbamoyl)-piperazin-1-yl]-piperidine-1-carboxylic acid tert-butyl ester (75 mg, 0.14 mmol) and sodium bicarbonate (59.4 mg, 0.71 mmol) in 1,4-dioxane (5.7 mL) and water (260 µL) was degassed with nitrogen for 20 min. Pd$_2$(dba)$_3$ (24.91 mg, 0.027 mmol) and 2-dicyclohexylphosphino-2',4',6'-triisopropylbiphenyl (64.8 mg, 0.14 mmol) were added and the reaction mixture was degassed with nitrogen for 15 min, heated at 90° C. for 12 h, concentrated, diluted with methanol and filtered through a pad of Celite®. The solution was then concentrated under vacuum and purified by reverse phase HPLC. Fractions containing product were combined and lyophilised overnight to afford a white powder, which was dissolved in 1:1 acetic acid:water and purified by reverse phase HPLC to provide the di-TFA salt of the title intermediate (47 mg, 31% yield). (m/z): [M+H]$^+$ calcd for C$_{45}$H$_{54}$F$_3$N$_8$O$_7$ 879.43 found 879.5.

Preparation 30

4-[1-(2,2-Dimethyl-propionyl)-piperidin-4-yl]-piperazine-1-carboxylic acid (4-bromo-3-trifluoromethoxy-phenyl)-amide

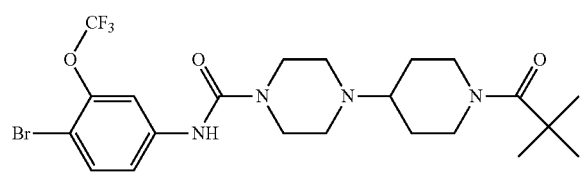 [SMILES: CC(C)(C)C(=O)N1CCC(N2CCN(C(=O)Nc3ccc(Br)c(OC(F)(F)F)c3)CC2)CC1]

(a) 4-Piperidin-4-yl-piperazine-1-carboxylic acid (4-bromo-3-trifluoromethoxy-phenyl)-amide A solution of 4-[4-(4-bromo-3-trifluoromethoxy-phenylcarbamoyl)-piperazin-1-yl]-piperidine-1-carboxylic acid tert-butyl ester (61.8 mg, 0.11 mmol) in 4 M of HCl in 1,4-dioxane (2.8 mL) was stirred at RT for 1 h to provide the title intermediate.

(b) 4-[1-(2,2-Dimethyl-propionyl)-piperidin-4-yl]-piperazine-1-carboxylic acid (4-bromo-3-trifluoromethoxy-phenyl)-amide To a solution of the product of the previous step in DMA (5.6 mL) was added 2,2-dimethylpropanoyl chloride (13.8 µL, 0.11 mmol) and DIPEA (97.6 µL, 0.56 mmol). The reaction mixture was stirred at RT for 1 h, concentrated under vacuum, and purified by silica gel chromatography (0-5% MeOH in DCM). The pure fractions were combined and concentrated under vacuum to provide the title intermediate (45 mg, 75% yield) as a white foam. (m/z): [M+H]$^+$ calcd for C$_{22}$H$_{30}$BrF$_3$N$_4$O$_3$ 535.15, 537.14 found 535.5.

Preparation 31

4-[1-(2,2-Dimethyl-propionyl)-piperidin-4-yl]-piperazine-1-carboxylic acid (4-bromo-3-trifluoromethoxy-phenyl)-amide

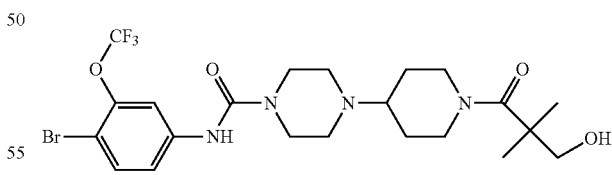

(a) 4-Piperidin-4-yl-piperazine-1-carboxylic acid (4-bromo-3-trifluoromethoxy-phenyl)-amide A solution of 4-[4-(4-bromo-3-trifluoromethoxy-phenylcarbamoyl)-piperazin-1-yl]-piperidine-1-carboxylic acid tert-butyl ester (61.8 mg, 0.11 mmol) in 4 M of HCl in 1,4-dioxane (2.8 mL) was stirred at RT for 1 h to provide the title intermediate.

(b) 4-[1-(3-Hydroxy-2,2-dimethyl-propionyl)-piperidin-4-yl]-piperazine-1-carboxylic acid (4-bromo-3-trifluoromethoxy-phenyl)-amide A solution of 2,2-dimethyl-3-hydroxypropionic acid (15.9 mg, 0.13 mmol) and HATU (51.1 mg, 0.13 mmol) in DMA (3 mL) was stirred at 50° C. for 15 min and then a solution of the product of the previous step in DMA (2.63 mL) was added, followed by DIPEA (97.6 µL, 0.56 mmol). The solution was stirred at 50° C. for 4 hours, concentrated under vacuum, and purified by silica gel chromatography (0-5% MeOH in DCM). The pure fractions were combined and concentrated under vacuum to provide the title intermediate (42 mg, 68% yield) as a white foam. (m/z): $[M+H]^+$ calcd for $C_{22}H_{30}BrF_3N_4O_4$ 551.14, 553.14 found 553.4.

Preparation 32

(2S,4S)-4-Methyl-2-{4-[4-(4,4,5,5-tetramethyl-1,3,2-dioxaborolan-2-yl)-phenyl]-1H-imidazol-2-yl}-pyrrolidine-1-carboxylic acid tert-butyl ester

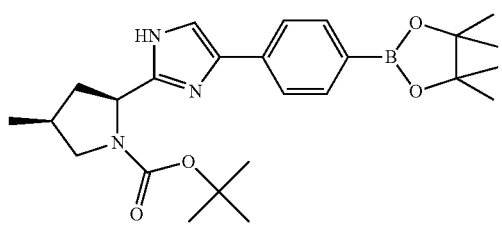

A solution of (2S,4S)-2-[4-(4-bromo-phenyl)-1H-imidazol-2-yl]-4-methyl-pyrrolidine-1-carboxylic acid tert-butyl ester (2.0 g, 4.9 mmol), bis(pinacolato)diboron (1.9 g, 7.4 mmol) and potassium acetate (0.72 g, 7.4 mmol) in 1,4-dioxane (16 mL) was degassed with nitrogen for 20 min and then Pd(dppf)Cl$_2$.CH$_2$Cl$_2$ (160 mg, 0.20 mmol) was added. The solution was degassed with nitrogen for 20 min, sealed, stirred at 100° C. overnight, cooled to RT, filtered through a pad of Celite®, washed with EtOAc (180 mL) and concentrated to give a black oil. The crude material was purified by silica gel chromatography (20-100% EtOAc/hexanes). Desired fractions were combined and concentrated to give the title intermediate (1.55 g, 69% yield) as a yellow solid. (m/z): $[M+H]^+$ calcd for $C_{25}H_{36}BN_3O_4$ 454.28 found 454.4.

Preparation 33

(2S,4S)-2-{4-[4'-({4-[4-(2,2-Dimethyl-pro piperazin-1-yl]-piperidine-1-carbonyl}-amino)-2'-trifluoromethoxy-biphenyl-4-yl]-1H-imidazol-2-yl}-4-methyl-pyrrolidine-1-carboxylic acid tert-butyl ester

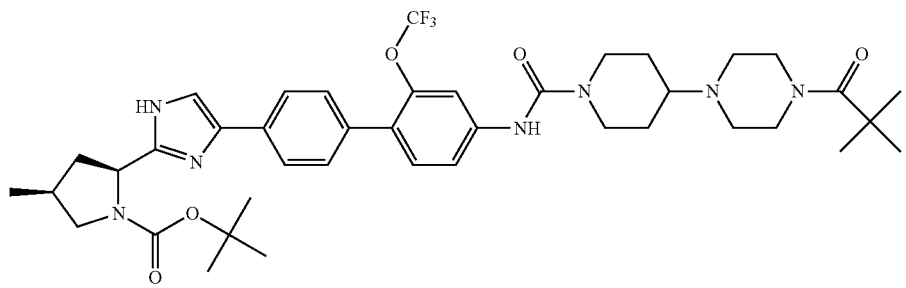 [SMILES: C[C@H]1C[C@@H](c2nc(-c3ccc(-c4ccc(NC(=O)N5CCC(N6CCN(C(=O)C(C)(C)C)CC6)CC5)cc4OC(F)(F)F)cc3)c[nH]2)N(C(=O)OC(C)(C)C)C1]

A solution of (2S,4S)-4-methyl-2-{4-[4-(4,4,5,5-tetramethyl-1,3,2-dioxaborolan-2-yl)-phenyl]-1H-imidazol-2-yl}-pyrrolidine-1-carboxylic acid tert-butyl ester (104 mg, 0.23 mmol; Preparation 32), 4-[1-(2,2-dimethyl-propionyl)-piperidin-4-yl]-piperazine-1-carboxylic acid (4-bromo-3-trifluoromethoxy-phenyl)-amide (122 mg, 0.23 mmol; Preparation 30) and sodium bicarbonate (100 mg, 1.19 mmol) in 1,4-dioxane (9.6 mL) and water (0.44 mL) was degassed with nitrogen for 20 min and then Pd$_2$(dba)$_3$ (41.8 mg, 0.046 mmol) and 2-dicyclohexylphosphino-2',4',6'-triisopropylbiphenyl (109 mg, 0.23 mmol) were introduced and the reaction was degassed with nitrogen for 15 min. The reaction solution was heated at 90° C. for 60 h, concentrated, diluted with methanol, filtered through a pad of Celite®, concentrated under vacuum, and purified by reverse phase HPLC. Desired fractions were combined and lyophilised overnight to afford a white powder. Impure fractions were combined and concentrated under vacuum, dissolved in a 1:1 acetic acid:water solution and purified by reverse phase HPLC to provide the di-TFA salt of the title intermediate (total 14.6 mg, 6% yield). (m/z): $[M+H]^+$ calcd for $C_{41}H_{54}F_3N7O_6$ 782.41 found 782.9.

Preparation 34

(S)-Methoxycarbonylamino-(tetrahydro-pyran-4-yl)-acetic acid

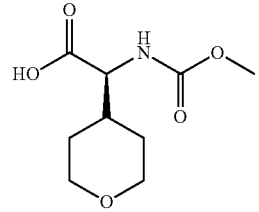

A solution of (S)-amino-(tetrahydro-pyran-4-yl)-acetic acid (1 g, 6.28 mmol) in saturated aqueous sodium bicarbonate solution (12.32 mL, 125.6 mmol) was stirred until all solids were dissolved. Methyl chloroformate (0.97 mL, 12.56 mmol) was added dropwise, the reaction mixture was stirred for 1 h, and 1N HCl was added to adjust pH to 1. The reaction mixture was extracted with ethyl acetate (3×15 mL) and the combined organic extracts were dried over sodium sulfate, filtered, concentrated and dried overnight under vacuum to give the title intermediate (1.36 g, 99% yield) as a white, sticky solid. (m/z): $[M+H]^+$ calcd for $C_9H_{15}NO_5$ 218.10 found 218.3.

Example 1

((S)-1-{(S)-2-[4-(4'-{[(S)-4-(1-Cyclopropanecarbonyl-piperidin-4-yl)-3-methyl-piperazine-1-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

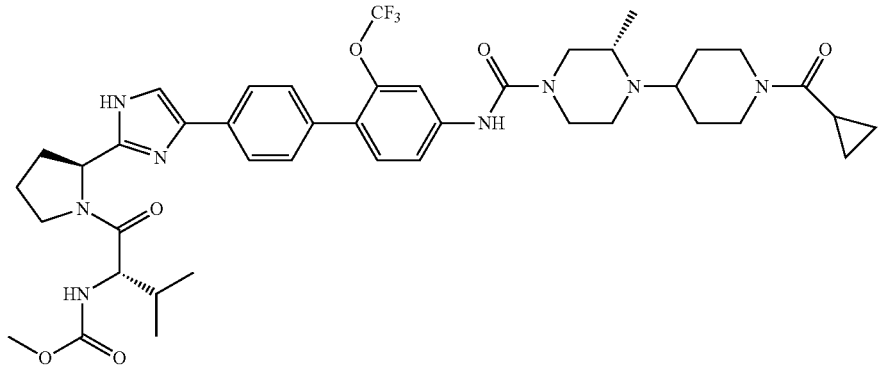 [SMILES: COC(=O)N[C@H](C(=O)N1CCC[C@H]1c1nc(-c2ccc(-c3ccc(NC(=O)N4CCN(C5CCN(C(=O)C6CC6)CC5)[C@@H](C)C4)cc3OC(F)(F)F)cc2)c[nH]1)C(C)C]

A mixture of ((S)-1-{(S)-2-[4-(4'-amino-2'-trifluoromethoxy-biphenyl-4-yl)-1H-imidazol-2-yl]-pyrrolidine-1-carbonyl}-2-methyl-propyl)-carbamic acid methyl ester (20 mg, 0.04 mmol) and p-nitrophenyl chloroformate (8.9 mg, 0.04 mmol) in DMA (5 mL) was stirred at RT for 30 min and then cyclopropyl-[4-((S)-2-methyl-piperazin-1-yl)-piperidin-1-yl]-methanone 2 HCl (18 mg, 0.06 mmol; Preparation 6) was added followed by DIPEA (32 μL, 0.18 mmol). The reaction mixture was stirred at RT for 1 h, concentrated, dissolved in 1:1 acetic acid:water (1.5 mL), and purified by reverse phase HPLC to provide the di-TFA salt of the title product (6.8 mg, 20% yield) (m/z): $[M+H]^+$ calcd for $C_{42}H_{53}F_3N_8O_6$ 823.40 found 823.6.

Example 2

[(S)-1-((S)-2-{4-[5'-Chloro-4'-({4-[1-(2,2-dichloro-cyclopropanecarbonyl)-piperidin-4-yl]-piperazine-1-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester

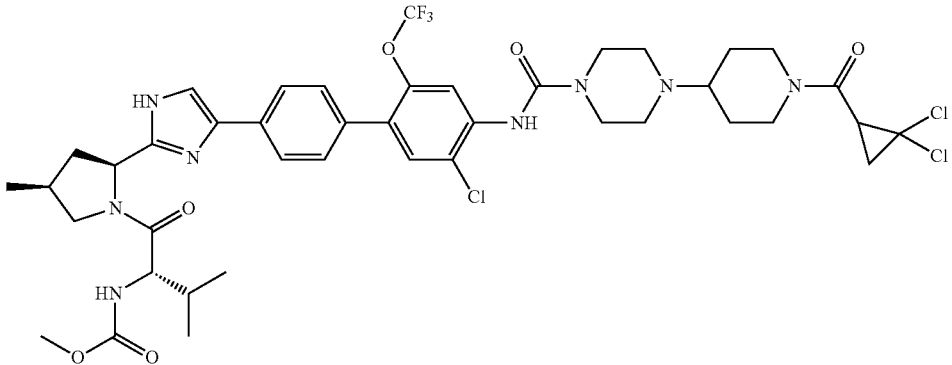 [SMILES: COC(=O)N[C@H](C(=O)N1C[C@@H](C)C[C@H]1c1nc(-c2ccc(-c3cc(Cl)c(NC(=O)N4CCN(C5CCN(C(=O)C6CC6(Cl)Cl)CC5)CC4)cc3OC(F)(F)F)cc2)c[nH]1)C(C)C]

A solution of 4-[4-(5-chloro-4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester 2TFA (12.94 mg, 0.012 mmol; Preparation 14) in 4 M HCl in 1,4-dioxane (0.21 mL) was stirred at RT for 30 min to provide the intermediate product {(S)-1-[(2S,4S)-2-(4-{5'-Chloro-4'-[(4-piperidin-4-yl-piperazine-1-carbonyl)-amino]-2'-trifluoromethoxy-biphenyl-4-yl}-1H-imidazol-2-yl)-4-methyl-pyrrolidine-1-carbonyl]-2-methyl-propyl}-carbamic acid methyl ester.

A solution of 0.5 M 2,2-dichlorocyclopropane-1-carboxylic acid in DMA (27.8 μL, 0.014 mmol), and HATU (5.28 mg, 0.014 mmol) in DMA (0.4 mL) was stirred at 50° C. for 15 min and then a solution of the intermediate product of the previous step (9.1 mg, 0.012 mmol) in DMA (0.58 mL, 6.25 mmol) was added followed by DIPEA (10.1 μL, 0.058 mmol). The reaction solution was stirred at 50° C. for 4 h, concentrated under vacuum and purified by reverse phase HPLC. Desired fractions were combined and lyophilized to provide the di-TFA salt of the title compound (8.2 mg, 61% yield). (m/z): [M+H]$^+$ calcd for $C_{42}H_{50}Cl_3F_3N_8O_6$ 925.29 found 925.8.

Examples 3-6

Following the procedure of Example 2, the intermediate product of the first step (9.1 mg, 0.012 mmol) in DMA (0.58 mL, 6.25 mmol) was reacted with the appropriate reagents to provide the following compounds:

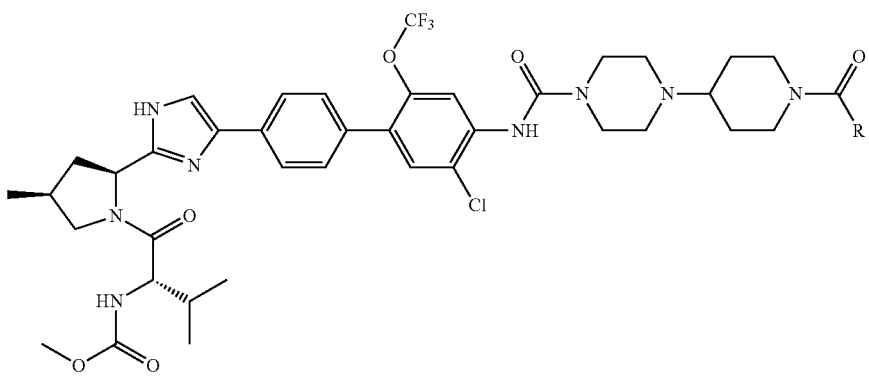

| Ex. No. | R | Reagent | Product |
|---|---|---|---|
| 3 | (S) | (S)-(+)-2,2-dimethylcyclopropane carboxylic acid in DMA (27.8 μL, 0.014 mmol) HATU (5.28 mg, 0.014 mmol) DIPEA (10 μL) | 2 TFA salt (7.4 mg) (m/z): [M + H]$^+$ calcd for $C_{44}H_{56}ClF_3N_8O_6$ 885.40 found 885.9 |
| 4 |  | 2,2-dimethylpropanoyl chloride (1.7 μL, 0.014 mmol) DIPEA (10 μL) | 2 TFA salt (5.8 mg) (m/z): [M + H]$^+$ calcd for $C_{43}H_{56}ClF_3N_8O_6$ 873.40 found 873.9 |
| 5 |  | 2,2-difluorocyclopropane carboxylic acid in DMA (27.8 μL, 0.014 mmol) HATU (5.28 mg, 0.014 mmol) DIPEA (10 μL) | 2 TFA salt (7.6 mg) (m/z): [M + H]$^+$ calcd for $C_{42}H_{50}ClF_5N_8O_6$ 893.35 found 893.6 |
| 6 |  | cyclobutane carboxylic acid (1.3 μL, .014 mm) HATU (5.28 mg, 0.014 mmol) DIPEA (10 μL) | 2 TFA salt (8.2 mg) (m/z): [M + H]$^+$ calcd for $C_{43}H_{54}ClF_3N_8O_6$ 871.38 found 871.9 |

Example 7

[(S)-1-((2S,4S)-2-{5-Chloro-4-[4'-({4-[1-(2,2-dimethyl-propionyl)-piperidin-4-yl]-piperazine-1-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester

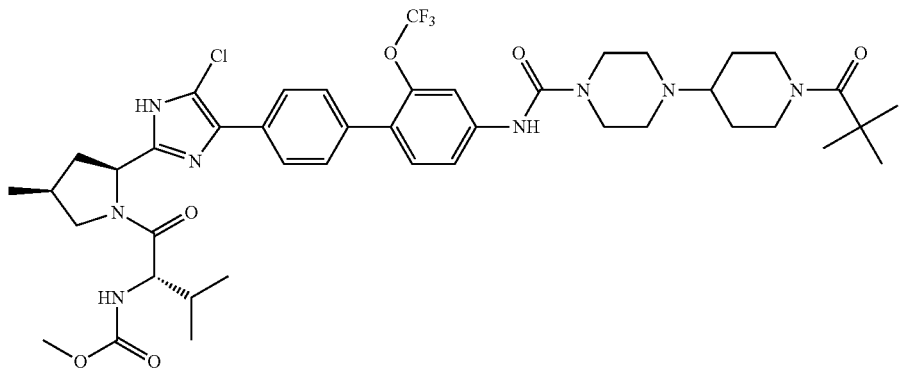 [SMILES: COC(=O)N[C@H](C(=O)N1C[C@@H](C)C[C@H]1c1nc(-c2ccc(-c3ccc(NC(=O)N4CCN(C5CCN(C(=O)C(C)(C)C)CC5)CC4)cc3OC(F)(F)F)cc2)c(Cl)[nH]1)C(C)C]

A mixture of {(S)-1-[(2S,4S)-2-(5-chloro-4-{4'-[(4-piperidin-4-yl-piperazine-1-carbonyl)-amino]-2'-trifluoromethoxy-biphenyl-4-yl}-1H-imidazol-2-yl)-4-methyl-pyrrolidine-1-carbonyl]-2-methyl-propyl}-carbamic acid methyl ester tri-HCl (10 mg, 0.01 mmol; Preparation 18) in DMA (1.5 mL) was stirred at RT to dissolution and then 2,2-dimethylpropanoyl chloride (1.4 μL, 0.011 mmol) was added followed by DIPEA (9.7 μL, 0.056 mmol). The reaction mixture was stirred at RT for 5 min, concentrated by rotary evaporation, dissolved in 1:1 acetic acid:water (4 mL), purified by reverse phase HPLC, and lyophilized to provide the TFA salt of the title intermediate (4 mg) as a yellow powder. (m/z): [M+H]$^+$ calcd for $C_{43}H_{56}ClF_3N_8O_6$ 873.40, found 873.4.

Example 8

[(S)-1-((2S,4S)-2-{4-[4'-({4-[1-(2,2-Dimethyl-propionyl)-piperidin-4-yl]-piperazine-1-carbonyl}-amino)-2'-trifluoromethoxy-biphenyl-4-yl]-5-fluoro-1H-imidazol-2-yl}-4-methyl-pyrrolidine-1-carbonyl)-2-methyl-propyl]-carbamic acid methyl ester (a) (S)-1-[(2S,4S)-2-(5-Fluoro-4-{4'-[(4-piperidin-4-yl-piperazine-1-carbonyl)-amino]-2'-trifluoromethoxy-biphenyl-4-yl}-1H-imidazol-2-yl)-4-methyl-pyrrolidine-1-carbonyl]-2-methyl-propyl}-carbamic acid methyl ester A solution of 4-[4-(4'-{5-fluoro-2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester di-TFA (11.5 mg, 0.01 mmol; Preparation 21) in 4 M of HCl in 1,4-dioxane (0.26 mL) was stirred at RT for 30 min, and concentrated under vacuum to afford a cream-colored solid.

(b) [(S)-1-((2S,4S)-2-{4-[4'-({4-[1-(2,2-Dimethyl-propionyl)-piperidin-4-yl]-piperazine-1-carbonyl}-amino)-2'-trifluoromethoxy-biphenyl-4-yl]-5-fluoro-1H-imidazol-2-yl}-4-methyl-pyrrolidine-1-carbonyl)-2-methyl-propyl]-carbamic acid methyl ester To the product of the previous step (8.1 mg, 0.01 mmol.) in DMA (0.52 mL) was added 2,2-dimethylpropanoyl chloride (1.29 μL, 0.01 mmol) and DIPEA (9.01 μL, 0.05 mmol). The reaction mixture was stirred at RT for 1 h and purified by reverse phase HPLC. Pure fractions were combined and lyophilised to provide the di-TFA salt of the title compound (4 mg, 33% yield). (m/z): [M+H]$^+$ calcd for $C_{43}H_{56}F_4N_8O_6$ 857.43, 858.43, found 858.7.

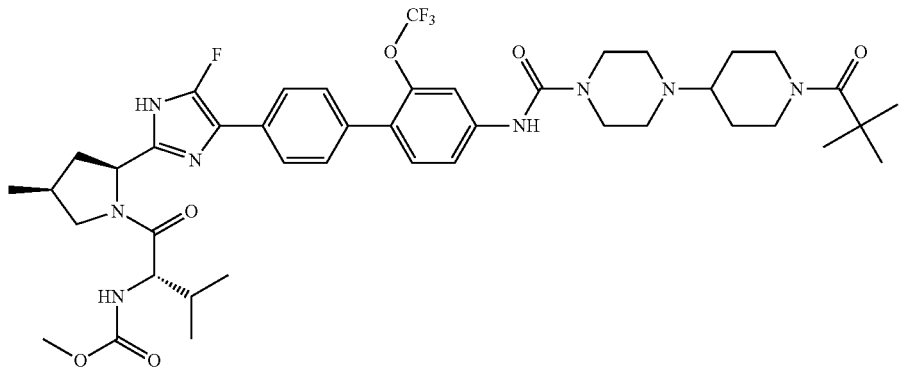 [SMILES: COC(=O)N[C@H](C(=O)N1C[C@@H](C)C[C@H]1c1nc(-c2ccc(-c3ccc(NC(=O)N4CCN(C5CCN(C(=O)C(C)(C)C)CC5)CC4)cc3OC(F)(F)F)cc2)c(F)[nH]1)C(C)C]

Examples 9-10

Following the procedure of Example 8, the product of step (a) (8.1 mg, 0.01 mmol) in DMA (0.52 mL) was reacted with the appropriate reagents to provide the following compounds:

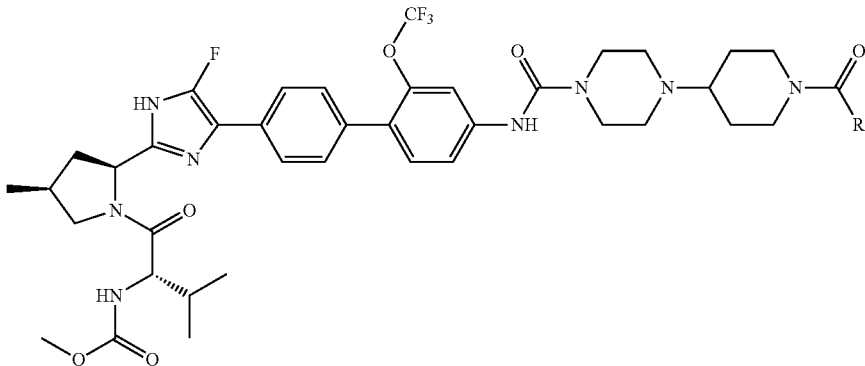

| Ex. No. | R | Reagent | Product |
|---|---|---|---|
| 9 | | cyclopropanoyl chloride (0.959 µL, 0.010 mmol) DIPEA (9.01 µL, 0.05 mmol) | 2 TFA salt (2.6 mg) (m/z): [M + H]+ calcd for $C_{42}H_{52}F_4N_8O_6$ 841.29 found 841.8 |
| 10 | | 0.5 M (S)-(+)-2,2-dimethylcyclopropane carboxylic acid in DMA (25.1 µL, 0.013 mmol) DIPEA (9.01 µL, 0.05 mmol) HATU (4.77 mg, 0.013 mmol) | 2 TFA salt (3 mg) (m/z): [M + H]+ calcd for $C_{44}H_{56}F_4N_8O_6$ 869.43 found 870.0 |

Example 11

((S)-1-{(2S,4S)-2-[4-(5'-Chloro-4'-{[4-((S)-4-dimethylcyclopropane-carbonyl-2-methyl-piperazin-1-yl)-piperidine-1-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester (a) ((S)-1-{(2S,4S)-2-[4-(5'-Chloro-4'-{[4-((S)-2-methyl-piperazin-1-yl)-piperidine-1-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester A solution of (S)-4-[1-(5-Chloro-4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphe-

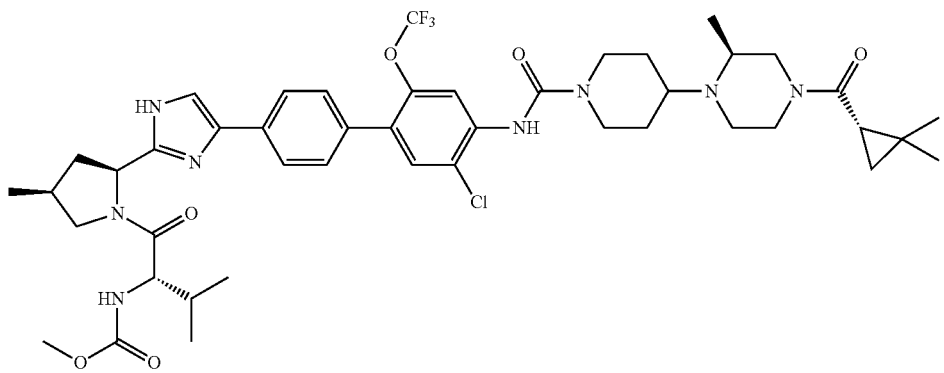

nyl-4-ylcarbamoyl)-piperidin-4-yl]-3-methyl-piperazine-1-carboxylic acid tert-butyl ester 2 TFA (6.35 mg, 0.006 mmol; Preparation 24) in 4.0 M HCl in 1,4-dioxane (0.1 mL) was stirred at RT for 30 min and concentrated under vacuum to provide the title intermediate. (m/z): [M+H]$^+$ calcd for $C_{39}H_{50}ClF_3N_8O_5$ 803.35 found 803.8.

(b) ((S)-1-{(2S,4S)-2-[4-(5'-Chloro-4'-{[4-((S)-4-dimethylcyclopropane-carbonyl-2-methyl-piperazin-1-yl)-piperidine-1-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester A solution of 0.5 M (S)-(+)-2,2-dimethylcyclopropane carboxylic acid in DMA (13.5 μL, 0.007 mmol) and HATU (2.56 mg, 0.007 mmol) in DMA (0.3 mL) was stirred at 50° C. for 15 min. and then the product of the previous step (4.5 mg, 0.006 mmol) and DIPEA (4.9 μL, 0.028 mmol) in DMA (0.3 mL) was added. The solution was stirred at 50° C. for 2 h, dissolved in 1:1 acetic acid:water (1.5 mL), purified by reverse phase HPLC to provide the di-TFA salt of the title product (2 mg, 40% yield). (m/z): [M+H]$^+$ calcd for $C_{45}H_{58}ClF_3N_8O_6$ 899.41 found 901.8.

Example 12

[(S)-1-((2S,4S)-2-{4-[5'-Chloro-4'-({4-[(S)-4-(2,2-dimethyl-propionyl)-2-methyl-piperazin-1-yl]-piperidine-1-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester

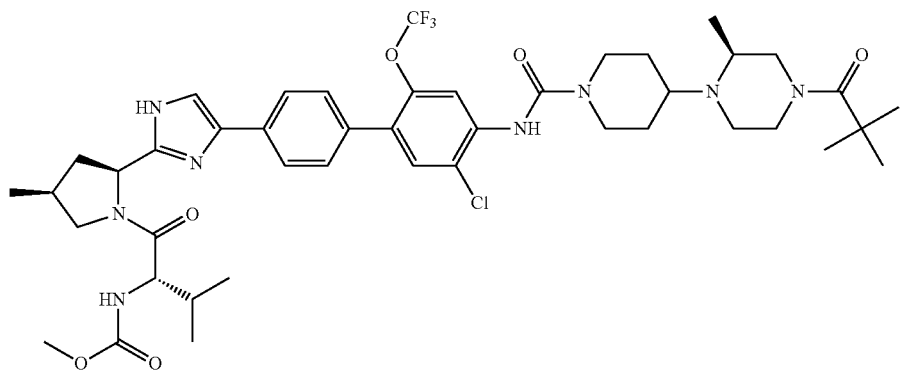 [SMILES: COC(=O)N[C@H](C(=O)N1C[C@@H](C)C[C@H]1c1nc(-c2ccc(-c3cc(Cl)c(NC(=O)N4CCC(N5CCN(C(=O)C(C)(C)C)C[C@@H]5C)CC4)cc3OC(F)(F)F)cc2)c[nH]1)C(C)C]

Following a procedure similar to that of Example 11, the product of Example 11, step (a) (4.5 mg, 0.006 mmol) in DMA (0.3 mL) was combined with 2,2-dimethyl-propanoyl chloride (0.7 μL, 0.006 mmol) and DIPEA (4.89 μL) to provide the di-TFA salt of the title compound (2 mg, 40% yield). (m/z): [M+H]$^+$ calcd for $C_{44}H_{58}ClF_3N_8O_6$ 887.41 found 887.8.

Example 13

4-[4-(4'-{2-[(2S,4S)-4-Methoxy-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester

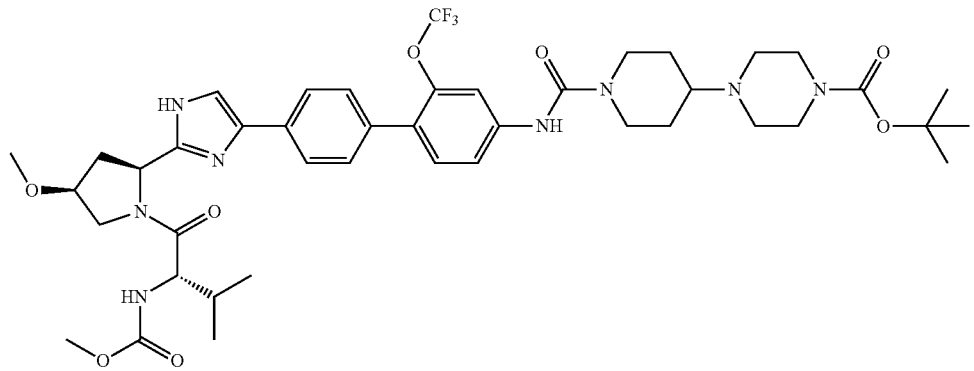 [SMILES: COC(=O)N[C@H](C(=O)N1C[C@@H](OC)C[C@H]1c1nc(-c2ccc(-c3ccc(NC(=O)N4CCC(N5CCN(C(=O)OC(C)(C)C)CC5)CC4)cc3OC(F)(F)F)cc2)c[nH]1)C(C)C]

A solution of [(S)-1-((2S,4S)-4-methoxy-2-{4-[4-(4,4,5,5-tetramethyl-1,3,2-dioxaborolan-2-yl)-phenyl]-1H-imidazol-2-yl}-pyrrolidine-1-carbonyl)-2-methyl-propyl]-carbamic acid methyl ester (35.5 mg, 0.067 mmol; Preparation 26), 4-[4-(4-bromo-3-trifluoromethoxy-phenylcarbamoyl)-piperazin-1-yl]-piperidine-1-carboxylic acid tert-butyl ester (37.1 mg, 0.067 mmol) and sodium bicarbonate (29.4 mg, 0.35 mmol) in 1,4-dioxane (2.8 mL) and water (129 µL) was degassed with nitrogen for 20 min. Pd₂(dba)₃ (12.33 mg, 0.013 mmol) and 2-dicyclohexylphosphino-2',4',6'-triisopropylbiphenyl (Xphos) (32.09 mg, 0.067 mmol) were added and the reaction was degassed with nitrogen for 15 min. The resulting solution was heated at 90° C. for 60 h, concentrated, diluted with methanol, filtered through a pad of Celite®, concentrated under vacuum, and purified by reverse phase HPLC. Fractions containing product were combined and lyophilised overnight to afford a white powder. Impure fractions were combined and concentrated under vacuum, dissolved in 1:1 acetic acid:ACN solution to provide the di-TFA salt of the title compound (40 mg, 54% yield) (m/z): [M+H]⁺ calcd for $C_{43}H_{57}F_3N_8O_8$ 871.43 found 871.8.

Example 14

[(S)-1-((2S,4S)-2-{4-[4'-({4-[4-(2,2-Dimethyl-cyclobutanecarbonyl)-piperazin-1-yl]-piperidine-1-carbonyl}-amino)-2'-trifluoromethoxy-biphenyl-4-yl]-1H-imidazol-2-yl}-4-methoxy-pyrrolidine-1-carbonyl)-2-methyl-propyl]-carbamic acid methyl ester (a) {(S)-1-[(2S,4S)-4-Methoxy-2-(4-{4'-[(4-piperidin-4-yl-piperazine-1-carbonyl)-amino]-2'-trifluoromethoxy-biphenyl-4-yl}-1H-imidazol-2-yl)-pyrrolidine-1-carbonyl]-2-methyl-propyl}-carbamic acid methyl ester A solution of 4-[4-(4'-{2-[(2S,4S)-4-Methoxy-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-piperazin-1-yl]-piperidine-1-carboxylic acid tert-butyl ester 2 TFA (9.7 mg, 0.009 mmol; Example 13) in 4.0 M HCl in 1,4-dioxane (0.22 mL) was stirred at RT for 30 min, and concentrated under vacuum to afford the title intermediate as a cream-colored powder.

(b) [(S)-1-((2S,4S)-2-{4-[4'-({4-[4-(2,2-Dimethyl-cyclobutanecarbonyl)-piperazin-1-yl]-piperidine-1-carbonyl}-amino)-2'-trifluoromethoxy-biphenyl-4-yl]-1H-imidazol-2-yl}-4-methoxy-pyrrolidine-1-carbonyl)-2-methyl-propyl]-carbamic acid methyl ester A solution of 2,2-dimethyl-cyclobutane carboxylic acid (1.36 mg, 0.011 mmol) and HATU (4.03 mg, 0.011 mmol) in DMA (0.44 mL) was stirred at 50° C. for 15 min. A solution of the intermediate product of the previous step in DMA (0.2 mL) was added, followed by DIPEA (7.7 µL, 0.044 mmol). The reaction mixture was stirred at 50° C. for 2 h, concentrated under vacuum, dissolved in 1:1 acetic acid:ACN (1.5 mL) and purified by reverse phase HPLC to provide the di-TFA salt of the title compound (0.9 mg). (m/z): [M+H]⁺ calcd for $C_{44}H_{59}F_3N_8O_7$ 881.45 found 881.8.

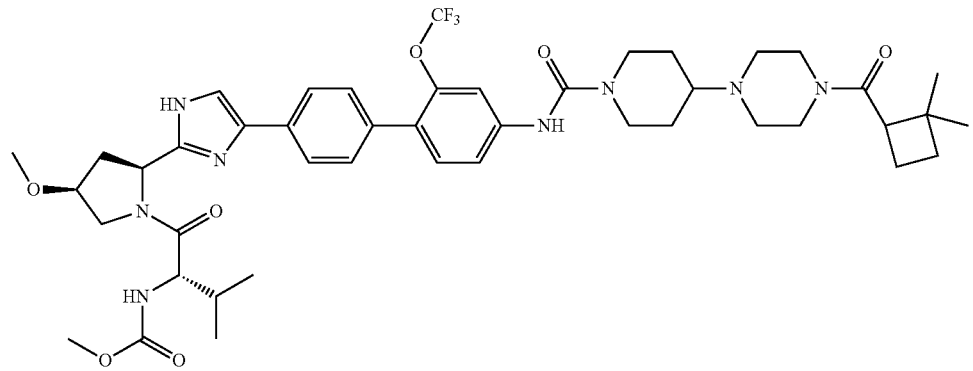

Example 15

[(S)-1-((2S,4S)-2-{7-[4-({4-[1-(2,2-Dimethyl-propionyl)-piperidin-4-yl]-piperazine-1-carbonyl}-amino)-2-trifluoromethoxy-phenyl]-3H-naphtho[1,2-d]imidazol-2-yl}-4-methyl-pyrrolidine-1-carbonyl)-2-methyl-propyl]-carbamic acid methyl ester

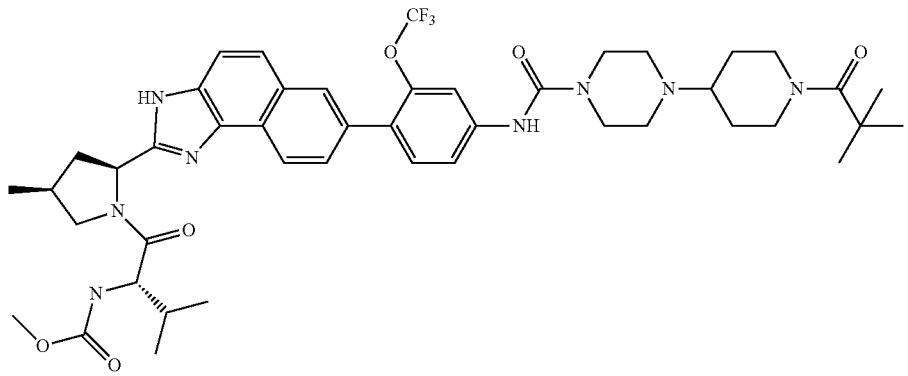 [SMILES: COC(=O)N[C@H](C(=O)N1C[C@@H](C)C[C@H]1c1nc2c(ccc3cc(-c4ccc(NC(=O)N5CCN(C6CCN(C(=O)C(C)(C)C)CC6)CC5)cc4OC(F)(F)F)ccc32)[nH]1)C(C)C]

(a) {(S)-2-Methyl-1-[(2S,4S)-4-methyl-2-(7-{4-[(4-piperidin-4-yl-piperazine-1-carbonyl)-amino]-2-trifluoromethoxy-phenyl}-3H-naphtho[1,2-d]imidazol-2-yl)-pyrrolidine-1-carbonyl]-propyl}-carbamic acid methyl ester A solution of 4-[4-(4-{2-[(2S,4S)-1-((S)-2-methoxycarbonylamino-3-methyl-butyryl)-4-methyl-pyrrolidin-2-yl]-3H-naphth[1,2-d]imidazol-7-yl}-3-trifluoromethoxy-phenylcarbamoyl)-piperazin-1-yl]-piperidine-1-carboxylic acid tert-butyl ester 2 TFA (8.8 mg, 0.008 mmol; Preparation 29) in 4.0 M HCl in 1,4-dioxane (0.20 mL) was stirred at RT for 30 min and concentrated under vacuum to afford the title intermediate as a white powder. (m/z): [M+H]$^+$ calcd for $C_{40}H_{49}F_3N_8O_5$ 779.38 found 779.8.

(b) [(S)-1-((2S,4S)-2-{7-[4-({4-[1-(2,2-Dimethyl-propionyl)-piperidin-4-yl]-piperazine-1-carbonyl}-amino)-2-trifluoromethoxy-phenyl]-3H-naphtho[1,2-d]imidazol-2-yl}-4-methyl-pyrrolidine-1-carbonyl)-2-methyl-propyl]-carbamic acid methyl ester To a solution of the product of the previous step in DMA (0.40 mL) was added 2,2-dimethylpropanoyl chloride (1.0 μL, 0.008 mmol) and DIPEA (6.9 μL, 0.04 mmol). The reaction mixture was stirred at RT for 30 min, concentrated under vacuum, dissolved in 1:1 acetic acid:water (1.5 mL) and purified by reverse phase HPLC to provide the di-TFA salt of the title compound (5 mg, 54% yield). (m/z): [M+H]$^+$ calcd for $C_{45}H_{57}F_3N_8O_6$ 863.44 found 863.8.

Example 16

((S)-1-{(2S,4S)-2-[7-(4-{[4-(1-Cyclopropanecarbonyl-piperidin-4-yl)-piperazine-1-carbonyl]-amino}-2-trifluoromethoxy-phenyl)-3H-naphth[1,2-d]imidazol-2-yl]-4-methyl-pyrrolidine-1-carbonyl}-2-methyl-propyl)-carbamic acid methyl ester

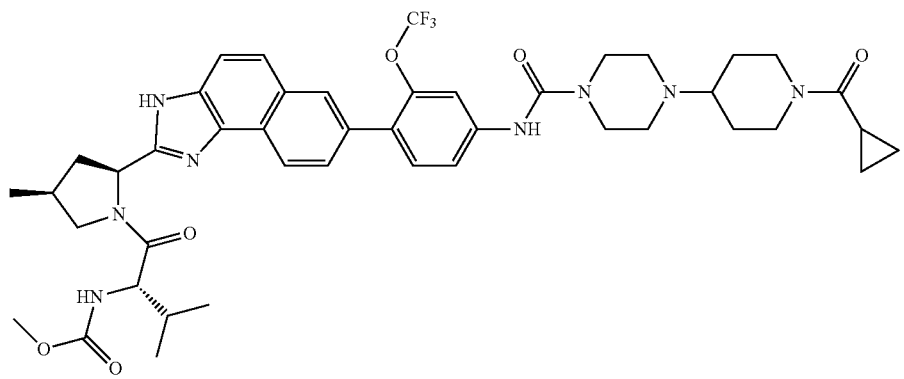 [SMILES: COC(=O)N[C@H](C(=O)N1C[C@@H](C)C[C@H]1c1nc2c(ccc3cc(-c4ccc(NC(=O)N5CCN(C6CCN(C(=O)C7CC7)CC6)CC5)cc4OC(F)(F)F)ccc32)[nH]1)C(C)C]

Following the procedure of Example 15, substituting cyclopropanecarbonyl chloride (0.76 µL, 0.008 mmol) for the 2,2-dimethylpropanoyl chloride (1.0 µL, 0.008 mmol), the di-TFA salt of the title compound was obtained (5 mg, 63% yield). (m/z): [M+H]⁺ calcd for $C_{44}H_{53}F_3N_8O_6$ 847.40 found 847.8.

Example 17

[(S)-2-((2S,4S)-2-{4-[4'-({4-[4-(2,2-Dimethyl-propionyl)-piperazin-1-yl]-piperidine-1-carbonyl}-amino)-2'-trifluoromethoxy-biphenyl-4-yl]-1H-imidazol-2-yl}-4-methyl-pyrrolidin-1-yl)-2-oxo-1-(tetrahydro-pyran-4-yl)-ethyl]-carbamic acid methyl ester

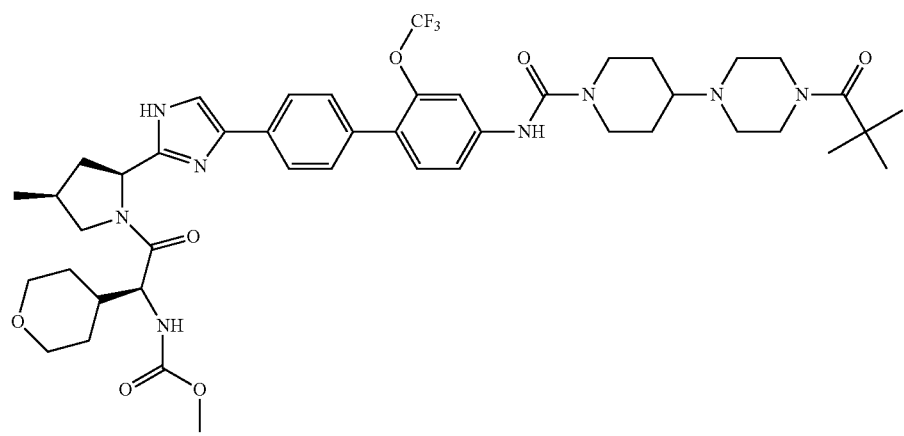 [SMILES: COC(=O)N[C@H](C(=O)N1C[C@@H](C)C[C@H]1c1nc(-c2ccc(-c3ccc(NC(=O)N4CCC(N5CCN(C(=O)C(C)(C)C)CC5)CC4)cc3OC(F)(F)F)cc2)c[nH]1)C1CCOCC1]

(a) 4-[1-(2,2-Dimethyl-propionyl)-piperidin-4-yl]-piperazine-1-carboxylic acid {4'-[2-((2S,4S)-4-methyl-pyrrolidin-2-yl)-1H-imidazol-4-yl]-2-trifluoromethoxy-biphenyl-4-yl}-amide A solution of (2S,4S)-2-{4-[4'-({4-[4-(2,2-dimethyl-propionyl)-piperazin-1-yl]-piperidine-1-carbonyl}-amino)-2'-trifluoromethoxy-biphenyl-4-yl]-1H-imidazol-2-yl}-4-methyl-pyrrolidine-1-carboxylic acid tert-butyl ester 2 TFA (12.3 mg, 0.012 mmol; Preparation 33) in 4 M HCl in 1,4-dioxane (0.23 mL) was stirred at RT for 30 min and concentrated under vacuum to provide the title intermediate as a cream-colored solid.

(b) [(S)-2-((2S,4S)-2-{4-[4'-({4-[4-(2,2-Dimethyl-propionyl)-piperazin-1-yl]-piperidine-1-carbonyl}-amino)-2'-trifluoromethoxy-biphenyl-4-yl]-1H-imidazol-2-yl}-4-methyl-pyrrolidin-1-yl)-2-oxo-1-(tetrahydro-pyran-4-yl)-ethyl]-carbamic acid methyl ester A solution of (S)-methoxycarbonylamino-(tetrahydro-pyran-4-yl)-acetic acid (3.44 mg, 0.016 mmol; Preparation 34) and HATU (6.02 mg, 0.016 mmol) in DMA (0.3 mL) was stirred at 50° C. for 30 min. A solution of the product of the previous step in DMA (0.61 mL) was added, followed by DIPEA (10.6 µL, 0.061 mmol). The solution was stirred at 50° C. for 1 h, concentrated under vacuum, and purified by reverse phase HPLC. Pure fractions were combined and lyophilised overnight to provide the di-TFA salt of the title compound (2 mg, 16% yield). (m/z): [M+H]⁺ calcd for $C_{45}H_{59}F_3N_8O_7$ 881.45 found 881.7.

Using similar synthetic procedures, the compounds of Tables 1 to 9 were prepared, where a blank in any column denotes hydrogen.

TABLE 1

| Ex No. | R$^{7a}$ | R$^{7d}$ | * | R$^{8a}$ | R$^{8b(\#)}$ | R$^{11}$ | Formula | Calc [M + H]$^+$ | Found [M + H]$^+$ |
|---|---|---|---|---|---|---|---|---|---|
| 1-1 | | | | | | -O-C(CH$_3$)$_3$ | C$_{41}$H$_{56}$N$_8$O$_6$ | 757.43 | 756.9 |
| 1-2 | | | | | | O-benzyl | C$_{44}$H$_{54}$N$_8$O$_6$ | 791.42 | 791.40 |
| 1-3 | | | | | | (S)-2,2-dimethylcyclopropyl | C$_{42}$H$_{56}$N$_8$O$_5$ | 753.44 | 753.4 |
| 1-4 | | | | | | (a) | C$_{49}$H$_{68}$N$_{10}$O$_8$ | 925.52 | 925.4 |
| 1-5 | | | | | | 1H-imidazol-4-yl-methyl | C$_{40}$H$_{50}$N$_{10}$O$_5$ | 751.4 | 751.4 |
| 1-6 | | | | | | (S)-methyl (3-methyl-1-oxobutan-2-yl)carbamate | C$_{43}$H$_{59}$N$_9$O$_7$ | 814.45 | 814.4 |
| 1-7 | | | | | | NHCH$_3$ | C$_{38}$H$_{51}$N$_9$O$_5$ | 714.40 | 714.4 |
| 1-8 | | | | | | cyclopropyl | C$_{40}$H$_{52}$N$_8$O$_5$ | 725.41 | 725.4 |
| 1-9 | | | | | | OCH$_3$ | C$_{38}$H$_{50}$N$_8$O$_6$ | 715.39 | 715.4 |
| 1-10 | OCF$_3$ | | | | | 3-hydroxyadamantyl | C$_{48}$H$_{61}$F$_3$N$_8$O$_7$ | 919.46 | 919.4 |
| 1-11 | OCF$_3$ | | | | | norbornyl | C$_{45}$H$_{57}$F$_3$N$_8$O$_6$ | 863.44 | 863.4 |

TABLE 1-continued

| Ex No. | R$^{7a}$ | R$^{7d}$ | * | R$^{8a}$ | R$^{8b(\#)}$ | R$^{11}$ | Formula | Calc [M + H]$^+$ | Found [M + H]$^+$ |
|---|---|---|---|---|---|---|---|---|---|
| 1-12 | OCF$_3$ | | | | | (S) 1,1-dimethylcyclopropyl | C$_{43}$H$_{55}$F$_3$N$_8$O$_6$ | 837.42 | 837.4 |
| 1-13 | OCF$_3$ | | | | | cyclopropyl-dimethyl | C$_{41}$H$_{51}$F$_3$N$_8$O$_6$ | 809.39 | 809.4 |
| 1-14 | OCF$_3$ | | | | | O-tBu dimethyl | C$_{42}$H$_{55}$F$_3$N$_8$O$_7$ | 841.41 | 841.4 |
| 1-15 | OCF$_3$ | | | | | NH-C(O)-NH$_2$ group | C$_{41}$H$_{53}$F$_3$N$_{10}$O$_7$ | 855.41 | 855.4 |
| 1-16 | OCF$_3$ | | | | | (a) | C$_{50}$H$_{67}$F$_3$N$_{10}$O$_9$ | 1009.50 | 1009.4 |
| 1-17 | OCF$_3$ | | | | | CH$_2$OH dimethyl | C$_{42}$H$_{55}$F$_3$N$_8$O$_7$ | 841.41 | 841.4 |
| 1-18 | OCF$_3$ | | (R) | CH$_3$ | | cyclopropyl-methyl | C$_{42}$H$_{53}$F$_3$N$_8$O$_6$ | 823.4 | 823.4 |
| 1-19 | OCF$_3$ | | (R) | CH$_3$ | | O-tBu methyl | C$_{43}$H$_{57}$F$_3$N$_8$O$_7$ | 855.43 | 855.4 |
| 1-20 | OCF$_3$ | F | | | | O-tBu dimethyl | C$_{42}$H$_{54}$F$_4$N$_8$O$_7$ | 859.41 | 859.8 |
| 1-21 | OCF$_3$ | | | | | pyrimidin-2-yl dimethyl | C$_{42}$H$_{49}$F$_3$N$_{10}$O$_6$ | 847.38 | 847.8 |

TABLE 1-continued

| Ex No. | R⁷ᵃ | R⁷ᵈ | * | R⁸ᵃ | R⁸ᵇ⁽#⁾ | R¹¹ | Formula | Calc [M + H]⁺ | Found [M + H]⁺ |
|---|---|---|---|---|---|---|---|---|---|
| 1-22 | OCF₃ | | | | | (CH₂-pyrazole group) | $C_{42}H_{51}F_3N_{10}O_6$ | 849.39 | 849.8 |
| 1-23 | OCF₃ | | | | | (imidazole group) | $C_{41}H_{49}F_3N_{10}O_6$ | 835.38 | 835.8 |
| 1-24 | OCF₃ | | | | | NHCH₃ | $C_{39}H_{50}F_3N_9O_6$ | 798.38 | 798.8 |
| 1-25 | OCF₃ | | | | | (CH₂NHAc group) | $C_{41}H_{52}F_3N_9O_7$ | 840.39 | 840.8 |
| 1-26 | OCF₃ | F | | | | (S)-dimethylcyclopropyl group | $C_{43}H_{54}F_4N_8O_6$ | 855.41 | 855.8 |
| 1-27 | OCF₃ | F | | | | (a) | $C_{50}H_{66}F_4N_{10}O_9$ | 1027.50 | 1028.0 |
| 1-28 | OCF₃ | F | | | | (cyclopropyl group) | $C_{41}H_{50}F_4N_8O_6$ | 827.38 | 827.8 |
| 1-29 | OCF₃ | | | | | (S)-NHCO₂Me group | $C_{44}H_{58}F_3N_9O_8$ | 898.44 | 898.6 |
| 1-30 | OCF₃ | | | | | (R)-NEt₂ group | $C_{46}H_{64}F_3N_9O_6$ | 896.49 | 896.6 |
| 1-31 | OCF₃ | | | | | (b) | $C_{49}H_{65}F_3H_{10}O_9$ | 995.49 | 995.0 |

TABLE 1-continued

| Ex No. | R^{7a} | R^{7d} | * | R^{8a} | R^{8b(#)} | R^{11} | Formula | Calc [M + H]^+ | Found [M + H]^+ |
|---|---|---|---|---|---|---|---|---|---|
| 1-32 | OCF$_3$ | | | | | 1-phenyl-1-(N,N-diethylamino)-tert-butyl (R) | C$_{49}$H$_{62}$F$_3$N$_9$O$_6$ | 930.48 | 930.6 |
| 1-33 | OCF$_3$ | Cl | | | | cyclopropyl-dimethyl | C$_{41}$H$_{50}$ClF$_3$N$_8$O$_6$ | 843.35 | 843.6 |
| 1-34 | OCF$_3$ | Cl | | | | (S)-dimethylcyclopropyl-dimethyl | C$_{43}$H$_{54}$ClF$_3$N$_8$O$_6$ | 871.38 | 871.6 |
| 1-35 | OCF$_3$ | Cl | | | | (a) | C$_{50}$H$_{66}$ClF$_3$N$_{10}$O$_9$ | 1043.47 | 1043.6 |
| 1-36 | OCF$_3$ | Cl | | | | O-tBu dimethyl | C$_{42}$H$_{54}$ClF$_3$N$_8$O$_7$ | 875.38 | 875.6 |
| 1-37 | OCF$_3$ | | | CH$_3$ | | (S)-dimethylcyclopropyl-dimethyl | C$_{44}$H$_{57}$F$_3$N$_8$O$_6$ | 851.44 | 851.8 |
| 1-38 | OCF$_3$ | | | CH$_3$ | | O-tBu dimethyl | C$_{43}$H$_{57}$F$_3$N$_8$O$_7$ | 855.43 | 855.8 |
| 1-39 | OCF$_3$ | | | CH$_3$ | | NHCH$_3$ | C$_{40}$H$_{52}$F$_3$N$_9$O$_6$ | 812.40 | 812.8 |
| 1-40 | OCF$_3$ | | | CH$_3$ | | cyclopropyl-dimethyl | C$_{42}$H$_{53}$F$_3$N$_8$O$_6$ | 823.40 | 823.8 |
| 1-41 | OCF$_3$ | | (S) | CH$_3$ | | cyclopropyl-dimethyl | C$_{42}$H$_{53}$F$_3$N$_8$O$_6$ | 823.40 | 823.8 |

TABLE 1-continued
| Ex No. | R^7a | R^7d | * | R^8a | R^8b(#) | R^11 | Formula | Calc [M + H]+ | Found [M + H]+ |
|---|---|---|---|---|---|---|---|---|---|
| 1-42 | OCF$_3$ | | | | CH$_2$OH | | C$_{43}$H$_{57}$F$_3$N$_8$O$_7$ | 855.43 | 855.8 |
| 1-43 | OCF$_3$ | | | | CH$_2$OH | NHCH$_3$ | C$_{40}$H$_{52}$F$_3$N$_9$O$_7$ | 828.39 | 828.8 |
| 1-44 | OCF$_3$ | | | | CH$_2$OH | | C$_{42}$H$_{53}$F$_3$N$_8$O$_7$ | 839.40 | 839.8 |
| 1-45 | OCF$_3$ | | | | CH$_2$OH | | C$_{44}$H$_{57}$F$_3$N$_8$O$_7$ | 867.43 | 868.0 |
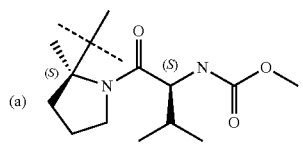
(a)
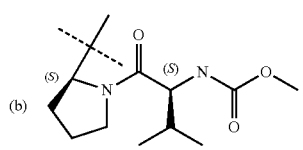
(b)
(#) For all compounds, when the substituent R^8b is present, the orientation of the chiral carbon atom bearing the substituent R^8b is (R).

TABLE 2
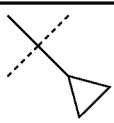
| Ex No. | R7a | R7d | R10 | R11 | Formula | Calc [M + H]+ | Found [M + H]+ |
|---|---|---|---|---|---|---|---|
| 2-1 | OCF3 | | | 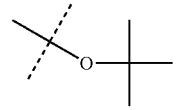 | C42H53F3N8O6 | 823.4 | 824.0 |
| 2-2 | OCF3 | F | |  | C43H56F4N8O7 | 873.42 | 873.8 |
| 2-3 | OCF3 | F | |  | C42H52F4N8O6 | 841.39 | 841.8 |
| 2-4 | OCF3 | F | | NHCH3 | C40H51F4N9O6 | 830.39 | 830.8 |
| 2-5 | OCF3 | F | | 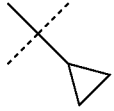 | C43H56F4N8O6 | 857.43 | 857.8 |
| 2-6 | OCF3 | Cl | | 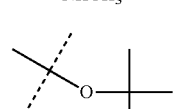 | C42H52ClF3N8O6 | 857.37 | 857.8 |
| 2-7 | OCF3 | Cl | | NHCH3 | C40H51ClF3N9O6 | 846.36 | 846.8 |
| 2-8 | OCF3 | Cl | |  | C43H56ClF3N8O7 | 889.39 | 889.8 |
| 2-9 | OCF3 | | |  | C43H57F3N8O6 | 839.44 | 839.8 |
| 2-10 | OCF3 | | | 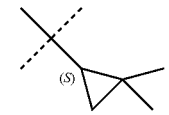 | C42H51F5N8O6 | 859.39 | 859.8 |
| 2-11 | OCF3 | | |  | C44H57F3N8O6 | 851.44 | 851.8 |
| 2-12 | OCF3 | | | NHCH3 | C40H52F3N9O6 | 812.40 | 812.8 |

TABLE 2-continued

| Ex No. | $R^{7a}$ | $R^{7d}$ | $R^{10}$ | $R^{11}$ | Formula | Calc [M + H]$^+$ | Found [M + H]$^+$ |
|---|---|---|---|---|---|---|---|
| 2-13 | OCF$_3$ | F | | cyclopropyl-CD$_3$,CD$_3$ | C$_{44}$H$_{50}$D$_6$F$_4$N$_8$O$_6$ | 875.46 | 876.6 |
| 2-14 | OCF$_3$ | F | | cyclopropyl-Cl,F | C$_{42}$H$_{50}$ClF$_5$N$_8$O$_6$ | 893.35 | 893.8 |
| 2-15 | OCF$_3$ | F | | cyclopropyl-Cl,Cl | C$_{42}$H$_{50}$Cl$_2$F$_4$N$_8$O$_6$ | 909.32 | 909.8 |
| 2-16 | OCF$_3$ | F | | (S)-cyclopropyl-Me | C$_{44}$H$_{56}$F$_4$N$_8$O$_6$ | 869.43 | 869.8 |
| 2-17 | OCF$_3$ | | Cl | (S)-cyclopropyl-Me | C$_{44}$H$_{56}$ClF$_3$N$_8$O$_6$ | 885.40 | 885.8 |
| 2-18 | OCF$_3$ | | Cl | OtBu | C$_{43}$H$_{56}$ClF$_3$N$_8$O$_7$ | 889.39 | 889.8 |
| 2-19 | OCF$_3$ | | | cyclobutyl | C$_{43}$H$_{55}$F$_3$N$_8$O$_6$ | 837.42 | 837.8 |
| 2-20 | OCF$_3$ | | | cyclopropyl-CD$_3$,CD$_3$ | C$_{44}$H$_{51}$D$_6$F$_3$N$_8$O$_6$ | 857.45 | 857.8 |
| 2-21 | OCF$_3$ | | | OtBu | C$_{43}$H$_{57}$F$_3$N$_8$O$_7$ | 855.43 | 855.8 |

TABLE 2-continued
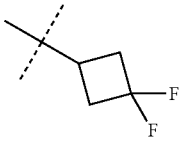
| Ex No. | R^{7a} | R^{7d} | R^{10} | R^{11} | Formula | Calc [M + H]^+ | Found [M + H]^+ |
|---|---|---|---|---|---|---|---|
| 2-22 | OCF$_3$ | Cl | | 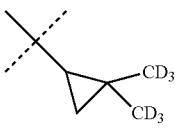 | C$_{43}$H$_{52}$ClF$_5$N$_8$O$_6$ | 907.36 | 907.8 |
| 2-23 | OCF$_3$ | Cl | | 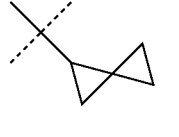 | C$_{44}$H$_{50}$ClD$_6$F$_3$N$_8$O$_6$ | 891.41 | 892.0 |
| 2-24 | OCF$_3$ | Cl | | 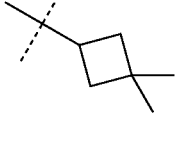 | C$_{44}$H$_{54}$ClF$_3$N$_8$O$_6$ | 883.38 | 883.8 |
| 2-25 | OCF$_3$ | Cl | | 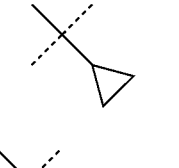 | C$_{45}$H$_{58}$ClF$_3$N$_8$O$_6$ | 899.41 | 899.8 |
| 2-26 | OCF$_3$ | | Cl | 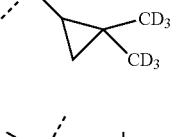 | C$_{42}$H$_{52}$ClF$_3$N$_8$O$_6$ | 857.37 | 857.8 |
| 2-27 | OCF$_3$ | | Cl | 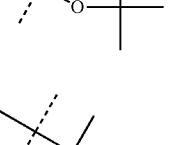 | C$_{44}$H$_{50}$ClD$_6$F$_3$N$_8$O$_6$ | 891.41 | 891.8 |
| 2-28 | OCF$_3$ | F | | 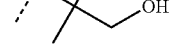 | C$_{43}$H$_{56}$F$_4$N$_8$O$_7$ | 873.42 | 873.8 |
| 2-29 | OCF$_3$ | | |  | C$_{43}$H$_{57}$F$_3$N$_8$O$_7$ | 855.43 | |

TABLE 3
| Ex No. | R7a | * | R9b | R11 | Formula | Calc [M + H]+ | Found [M + H]+ |
|---|---|---|---|---|---|---|---|
| 3-1 | | | | (tBuO-C(CH3)2-) | $C_{41}H_{56}N_8O_6$ | 757.43 | 756.9 |
| 3-2 | | | | (S)-2,2-dimethylcyclopropyl | $C_{42}H_{56}N_8O_5$ | 753.44 | 753.4 |
| 3-3 | | | | cyclopropyl-C(CH3)2- | $C_{40}H_{52}N_8O_5$ | 725.41 | 725.4 |
| 3-4 | | | | (1H-imidazol-4-yl)-C(CH3)2- | $C_{40}H_{50}N_{10}O_5$ | 751.40 | 751.7 |
| 3-4 | | | | (a) | $C_{49}H_{68}N_{10}O_8$ | 925.52 | 925.6 |
| 3-5 | | | | NHCH3 | $C_{38}H_{51}N_9O_5$ | 714.40 | 714.4 |
| 3-6 | | | | OCH3 | $C_{38}H_{50}N_8O_6$ | 715.39 | 715.4 |
| 3-7 | OCF3 | (R) | CH3 | (tBuO-C(CH3)2-) | $C_{43}H_{57}F_3N_8O_7$ | 855.43 | 855.4 |
| 3-8 | OCF3 | (R) | CH3 | (S)-2,2-dimethylcyclopropyl | $C_{44}H_{57}F_3N_8O_6$ | 851.44 | 851.4 |
| 3-9 | OCF3 | (R) | CH3 | (a) | $C_{51}H_{69}F_3N_{10}O_9$ | 1023.52 | 1023.4 |
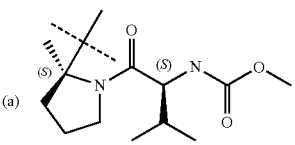
(a)

TABLE 4

| Ex No. | R⁷ᵈ | * | R⁹ᵃ | # | R⁹ᵇ | R¹¹ | Formula | Calc [M + H]⁺ | Found [M + H]⁺ |
|---|---|---|---|---|---|---|---|---|---|
| 4-1 | Cl | | | (S) | CH₃ | *tert-butoxy-dimethyl group* | $C_{44}H_{58}ClF_3N_8O_7$ | 903.41 | 903.8 |
| 4-2 | Cl | | | (S) | CH₃ | *(S)-1,2-dimethylcyclopropyl* | $C_{45}H_{58}ClF_3N_8O_6$ | 899.41 | 889.9 |
| 4-3 | Cl | | | (S) | CH₃ | *tert-butyl* | $C_{44}H_{58}ClF_3N_8O_6$ | 887.41 | 887.8 |
| 4-4 | Cl | | | (S) | CH₃ | NHCH₃ | $C_{41}H_{53}ClF_3N_9O_6$ | 860.38 | 860.8 |
| 4-5 | Cl | | | (S) | CH₃ | *1-methylcyclopropyl* | $C_{43}H_{54}ClF_3N_8O_6$ | 871.38 | 871.8 |
| 4-6 | F | | | | | *tert-butoxy-dimethyl group* | $C_{43}H_{56}F_4N_8O_7$ | 873.42 | 873.8 |
| 4-7 | F | | | | | *tert-butyl* | $C_{43}H_{56}F_4N_8O_6$ | 857.43 | 857.8 |
| 4-8 | F | | | | | *(S)-1,2-dimethylcyclopropyl* | $C_{44}H_{56}F_4N_8O_6$ | 869.43 | 869.8 |
| 4-9 | F | | | | | *1-methylcyclopropyl* | $C_{42}H_{52}F_4N_8O_6$ | 841.39 | 841.8 |
| 4-10 | | | | | | *tert-butyl* | $C_{43}H_{57}F_3N_8O_6$ | 839.44 | 839.8 |

TABLE 4-continued

| Ex No. | R$^{7d}$ | * | R$^{9a}$ | # | R$^{9b}$ | R$^{11}$ | Formula | Calc [M + H]$^+$ | Found [M + H]$^+$ |
|---|---|---|---|---|---|---|---|---|---|
| 4-11 | | | | | | (S)-2,2-dimethylcyclopropyl | C$_{44}$H$_{57}$F$_3$N$_8$O$_6$ | 851.44 | 851.8 |
| 4-12 | Cl | | | | | OC(CH$_3$)$_3$ | C$_{43}$H$_{56}$ClF$_3$N$_8$O$_7$ | 889.39 | 889.8 |
| 4-13 | Cl | | | | | C(CH$_3$)$_3$ | C$_{43}$H$_{56}$ClF$_3$N$_8$O$_6$ | 873.40 | 873.8 |
| 4-14 | Cl | | | | | (S)-2,2-dimethylcyclopropyl | C$_{44}$H$_{56}$ClF$_3$N$_8$O$_6$ | 885.40 | 885.8 |
| 4-15 | Cl | | | | | cyclopropyl-methyl | C$_{42}$H$_{52}$ClF$_3$N$_8$O$_6$ | 857.37 | 857.8 |
| 4-16 | Cl | (R) | CH$_3$ | | | C(CH$_3$)$_3$ | C$_{44}$H$_{58}$ClF$_3$N$_8$O$_6$ | 887.41 | 887.7 |
| 4-17 | Cl | (R) | CH$_3$ | | | (S)-2,2-dimethylcyclopropyl | C$_{45}$H$_{58}$ClF$_3$N$_8$O$_6$ | 899.41 | 899.8 |

TABLE 5
| Ex No. | R<sup>7a</sup> | R<sup>11</sup> | Formula | Calc [M + H]<sup>+</sup> | Found [M + H]<sup>+</sup> |
|---|---|---|---|---|---|
| 5-1 | OCF$_3$ | 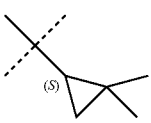 | C$_{43}$H$_{57}$F$_3$N$_8$O$_7$ | 855.43 | 855.8 |
| 5-2 | OCF$_3$ | 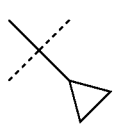 | C$_{44}$H$_{57}$F$_3$N$_8$O$_7$ | 867.43 | 867.8 |
| 5-3 | OCF$_3$ | 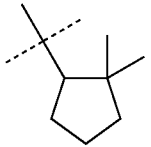 | C$_{42}$H$_{53}$F$_3$N$_8$O$_7$ | 839.40 | 839.8 |
| 5-4 | OCF$_3$ | 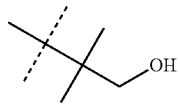 | C$_{46}$H$_{61}$F$_3$N$_8$O$_7$ | 895.46 | 895.8 |
| 5-5 | OCF$_3$ |  | C$_{43}$H$_{57}$F$_3$N$_8$O$_8$ | 871.43 | 871.8 |

TABLE 6

| Ex No. | R⁷ᵃ | R¹¹ | Formula | Calc [M + H]⁺ | Found [M + H]⁺ |
|---|---|---|---|---|---|
| 6-1 | OCF₃ | (S)-1,2-dimethylcyclopropyl | $C_{46}H_{57}F_3N_8O_6$ | 875.44 | 875.8 |
| 6-2 | OCF₃ | OC(CH₃)₃-C(CH₃)₂ | $C_{45}H_{57}F_3N_8O_7$ | 879.43 | 879.8 |
| 6-3 | OCF₃ | 1,1-dimethyl-(2,2-dimethylcyclobutyl) | $C_{47}H_{59}F_3N_8O_6$ | 889.45 | 889.8 |
| 6-4 | OCF₃ | C(CH₃)₂C(CH₃)₂CH₂OH | $C_{45}H_{57}F_3N_8O_7$ | 879.43 | 879.8 |

TABLE 7

| Ex No. | R⁷ᵃ | R¹¹ | Formula | Calc [M + H]⁺ | Found [M + H]⁺ |
|---|---|---|---|---|---|
| 7-1 | OCF₃ | C(CH₃)₂-O-C(CH₃)₃ | $C_{47}H_{59}F_3N_8O_8$ | 921.44 | 921.8 |

TABLE 7-continued
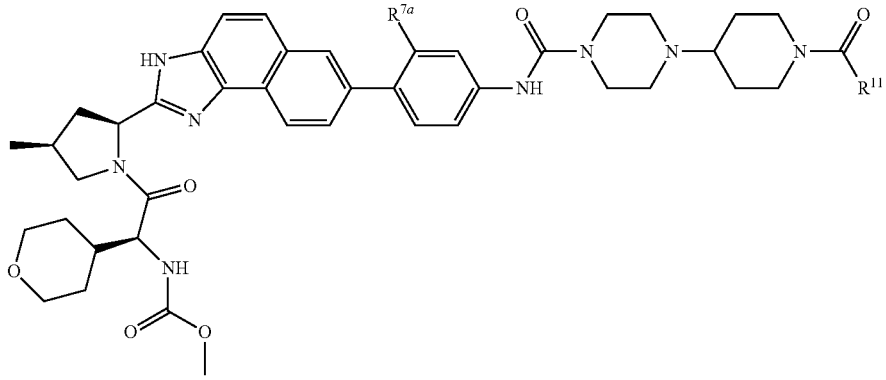
| Ex No. | R^{7a} | R^{11} | Formula | Calc [M + H]^+ | Found [M + H]^+ |
|---|---|---|---|---|---|
| 7-2 | OCF$_3$ | 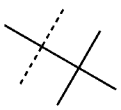 | C$_{47}$H$_{59}$F$_3$N$_8$O$_7$ | 905.45 | 905.8 |
| 7-3 | OCF$_3$ | 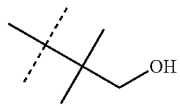 | C$_{47}$H$_{59}$F$_3$N$_8$O$_8$ | 921.44 | 921.8 |
| 7-4 | OCF$_3$ | 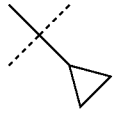 | C$_{46}$H$_{55}$F$_3$N$_8$O$_7$ | 889.41 | 889.8 |
| 7-5 | OCF$_3$ | 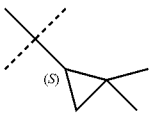 | C$_{48}$H$_{59}$F$_3$N$_8$O$_7$ | 917.45 | 918.0 |
TABLE 8
| Ex No. | Formula | Calc [M + H]^+ | Found [M + H]^+ |
|---|---|---|---|
| 8-1 | C$_{43}$H$_{53}$F$_3$N$_8$O$_6$ | 835.4 | 836.0 |
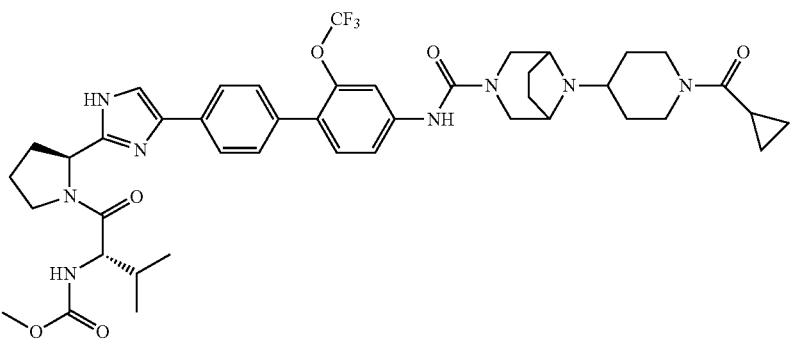 [SMILES: COC(=O)N[C@H](C(=O)N1CCC[C@H]1c1nc(-c2ccc(-c3ccc(NC(=O)N4CC5CCC(C4)N5C4CCN(C(=O)C5CC5)CC4)cc3OC(F)(F)F)cc2)c[nH]1)C(C)C]

TABLE 8-continued

| Ex No. | Formula | Calc [M + H]+ | Found [M + H]+ |
|---|---|---|---|
| 8-2 | C₄₄H₅₇F₃N₈O₇ | 867.43 | 868.0 |
| 8-3 | C₄₃H₅₇F₃N₈O₆ | 839.44 | 839.8 |
| 8-4 | C₄₂H₅₃F₃N₈O₆ | 823.4 | 823.8 |
| 8-5 | C₄₄H₅₇F₃N₈O₆ | 851.44 | 851.8 |

TABLE 9

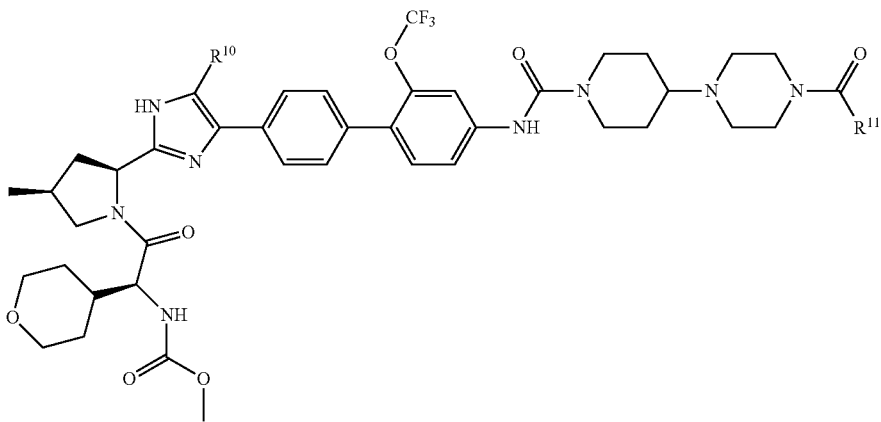

| Ex No. | R[10] | R[11] | Formula | Calc [M + H]+ | Found [M + H]+ |
|---|---|---|---|---|---|
| 9-1 | | 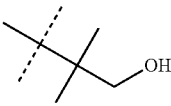 | C45H59F3N8O8 | 897.44 | 897.8 |
| 9-2 | F | 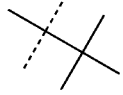 | C45H58F4N8O7 | 899.44 | 899.8 |
| 9-3 | F |  | C45H58F4N8O8 | 915.43 | 915.8 |

Biological Assays

The hepatitis C virus has been classified into six major different genotypes on the basis of nucleotide sequence, and further divided into subtypes within genotypes. Compounds of the invention demonstrated inhibition of HCV replication in one or more of the following HCV replicon assays.

Assay 1: HCV Genotype 1b Replicon Assay

The HCV genotype 1b replicon cell line was obtained from Apath LLC (Brooklyn, N.Y.) (APC144; Huh7 cell background). This subgenomic replicon contains the N-terminus of the HCV core protein fused to the neomycin-resistance selectable marker. The EMCV IRES lies downstream and drives expression of humanized Renilla luciferase fused to the non-structural proteins NS3-NS5B. This cell line was used to determine compound potency using the luciferase activity readout as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 500 µg/mL G418 (Invitrogen). On day 1 of the assay, cells were plated at 10,000 cells/well in white 96-well tissue culture plates (Costar) in 200 µL media lacking G418. Four hours later, once the cells have adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 hours. At the end of the incubation period, media and compound were removed from the plates and the luciferase activity was determined using Promega Renilla-Glo reagents.

To analyze the data, the luciferase activity was plotted vs. the compound concentration, and $EC_{50}$ values were determined from a 4-parameter robust fit model with the GraphPad Prism software package (GraphPad Software, Inc., San Diego, Calif.). Results are expressed as the negative decadic logarithm of the $EC_{50}$ value, $pEC_{50}$.

Test compounds having a higher $pEC_{50}$ value in this assay show greater inhibition of HCV genotype 1b replication. Compounds of the invention tested in this assay typically exhibited $pEC_{50}$ values between about 7 and about 12.

Assay 2: HCV Genotype 1a Replicon Assay

The HCV genotype 1a replicon cell line was obtained from Apath LLC (APC89; Huh7.5 cell background). This subgenomic replicon contains the N-terminus of the HCV core protein fused to the neomycin-resistance selectable marker. The EMCV IRES lies downstream and drives expression of the non-structural proteins NS3-NS5B. Compound potencies were determined using the NS3-specific protease activity in lysates as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 850 µg/mL G418 (Invitrogen). On day 1 of the assay, cells were plated at 15,000 cells/well in black 96-well tissue culture plates (Costar) in 200 µL media lacking G418. Four hours later, once the cells had adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 or 72 hours. At the end of the incubation period, media and compound were removed from the plates.

To determine the NS3-specific protease activity in lysates, the cells were lysed at room temperature in 50 μL/well of 50 mM Hepes pH 7.5, 150 mM NaCl, 15% Glycerol, 0.15% Triton X-100, 10 mM DTT for 20 minutes with shaking. 50 μL of an NS3/4a protease-specific FRET substrate (Anaspec RET SI Cat#22991) was then added to the wells at a final concentration of 15 μM. The plates were incubated at 37° C. for 20 minutes, which corresponds to a timepoint at which the protease activity is still in the linear phase. Protease activity was determined by measuring fluorescence (Excitation: 340 nm; Emission: 509 nm).

To analyze the data, the fluorescence was plotted vs. the compound concentration, and EC50 values were determined from a 4-parameter robust fit model using GraphPad Prism software. Compounds of the invention tested in this assay typically exhibited $pEC_{50}$ values between about 6 and about 11.5.

Assay 3: Replicon Assays Against Resistant Mutants

To create replicon cells with resistant mutations of interest, the mutation was first introduced into the parental plasmid by site-directed mutagenesis. Mutations in genotype 1b included L31V, Y93H, and the L31V/Y93H double mutant. Mutations in genotype 1a included Q30R and L31V. The replicon plasmid was then linearized and in vitro transcribed to RNA. The RNA was used to stably transfect Huh7 cells by electroporation, and new cell lines were selected with 500 μg/mL G418. Potencies of test compounds against these mutant cell lines were determined as previously described above for the HCV Genotype 1b and 1a replicon assays.

Potencies of test compounds against additional mutations of interest were determined using transient transfection assays. These mutants included and genotype 1a Y93C, Y93H, M28T, Q30E, Q30K. The mutation was first introduced into the parental plasmid by site-directed mutagenesis. The replicon plasmid was then linearized and in vitro transcribed to RNA. The RNA was used to transiently transfect Huh-LUNET cells (obtained from ReBLikon GmbH, Schriesheim, Germany) by electroporation, and the potencies of test compounds against the mutants were determined as previously described.

Assay 4: Additional Replicon Assays

Potencies of test compounds against NS5A sequences of other genotypes were determined by creating intergenotypic chimeras. The entire NS5A gene from genotypes 2-6, or the nucleotide sequence encoding amino acids 11-118 of NS5A, was subcloned into a genotype 1b replicon. These chimeric replicon plasmids were then linearized and in vitro transcribed to RNA. The RNA was used to transiently or stably transfect Huh-LUNET cells by electroporation, and the potencies of test compounds against the chimeras were determined as previously described.

Assay Results

All of the compounds of Examples 1 to 17 and Tables 1 to 9 were tested in one or more of the assays described above. For example, the following results were obtained in the HCV genotype 1a and 1b replicon assays where A represents a $pEC_{50}$ value between 6 and 8 ($EC_{50}$ between 1 μM and 10 nM), B represents $pEC_{50}$ between 8 and 9 ($EC_{50}$ between 1 and 10 nM), C represents $pEC_{50}$ between and 9 and about 10, ($EC_{50}$ between 1 nM and 0.1 nM), and D represents $pEC_{50}$>10 ($EC_{50}$<0.1 nM).

TABLE 1

| Example No. | Genotype 1a | Genotype 1b |
|---|---|---|
| 1 | C | |
| 2 | B | |
| 3 | C | |
| 4 | C | |
| 5 | C | |
| 6 | C | |
| 7 | D | D |
| 8 | D | |
| 9 | D | |
| 10 | D | |
| 11 | D | D |
| 12 | C | |
| 13 | C | |
| 14 | C | |
| 15 | D | |
| 16 | D | D |
| 17 | C | D |
| 1-1 | C | D |
| 1-2 | B | |
| 1-3 | C | |
| 1-4 | B | |
| 1-5 | B | |
| 1-6 | A | |
| 1-7 | B | |
| 1-8 | C | D |
| 1-9 | B | |
| 1-10 | B | |
| 1-11 | C | |
| 1-12 | C | D |
| 1-13 | C | D |
| 1-14 | C | D |
| 1-15 | B | |
| 1-16 | C | D |
| 1-17 | C | D |
| 1-18 | C | |
| 1-19 | C | |
| 1-20 | C | |
| 1-21 | B | |
| 1-22 | C | |
| 1-23 | C | |
| 1-24 | C | |
| 1-25 | C | |
| 1-26 | C | |
| 1-27 | C | |
| 1-28 | C | |
| 1-29 | A | |
| 1-30 | A | |
| 1-31 | A | |
| 1-32 | A | |
| 1-33 | C | |
| 1-34 | C | |
| 1-35 | C | |
| 1-36 | C | |
| 1-37 | B | |
| 1-38 | B | |
| 1-39 | B | |
| 1-40 | B | |
| 1-41 | B | |
| 1-42 | B | |
| 1-43 | A | |
| 1-44 | A | |
| 1-45 | B | |

TABLE 2

| Example No. | Genotype 1a | Genotype 1b |
|---|---|---|
| 2-1 | D | |
| 2-2 | D | |
| 2-3 | D | |
| 2-4 | D | |
| 2-5 | D | D |
| 2-6 | D | D |

TABLE 2-continued

| Example No. | Genotype 1a | Genotype 1b |
|---|---|---|
| 2-7 | C | |
| 2-8 | C | |
| 2-9 | D | D |
| 2-10 | C | |
| 2-11 | D | |
| 2-12 | C | |
| 2-13 | D | |
| 2-14 | C | |
| 2-15 | C | |
| 2-16 | D | D |
| 2-17 | D | D |
| 2-18 | C | |
| 2-19 | C | D |
| 2-20 | D | D |
| 2-21 | D | D |
| 2-22 | B | |
| 2-23 | C | |
| 2-24 | B | |
| 2-25 | B | |
| 2-26 | D | |
| 2-27 | D | |
| 2-28 | D | |
| 2-29 | C | |

TABLE 3

| | | |
|---|---|---|
| 3-1 | A | |
| 3-2 | B | D |
| 3-3 | A | |
| 3-4 | A | |
| 3-4 | B | |
| 3-5 | A | |
| 3-6 | A | |
| 3-7 | B | |
| 3-8 | B | |
| 3-9 | C | |

TABLE 4

| Example No. | Genotype 1a | Genotype 1b |
|---|---|---|
| 4-1 | A | |
| 4-2 | C | |
| 4-3 | B | |
| 4-4 | B | |
| 4-5 | B | |
| 4-6 | B | |
| 4-7 | C | |
| 4-8 | C | |
| 4-9 | C | |
| 4-10 | C | |
| 4-11 | C | |
| 4-12 | B | |
| 4-13 | B | |
| 4-14 | C | |
| 4-15 | B | |
| 4-16 | C | |
| 4-17 | C | |

TABLE 5

| 5-1 | C |
| 5-2 | C |
| 5-3 | C |
| 5-4 | C |
| 5-5 | C |

TABLE 6

| 6-1 | D | D |
| 6-2 | D | |
| 6-3 | D | |
| 6-4 | D | D |

TABLE 7

| 7-1 | D |
| 7-2 | D |
| 7-3 | C |
| 7-4 | D |
| 7-5 | D |

TABLE 8

| 8-1 | B |
| 8-2 | C |
| 8-3 | C |
| 8-4 | C |
| 8-5 | C |

TABLE 9

| 9-1 | C | D |
| 9-2 | D | D |
| 9-3 | C | D |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:
1. A compound of formula (I):

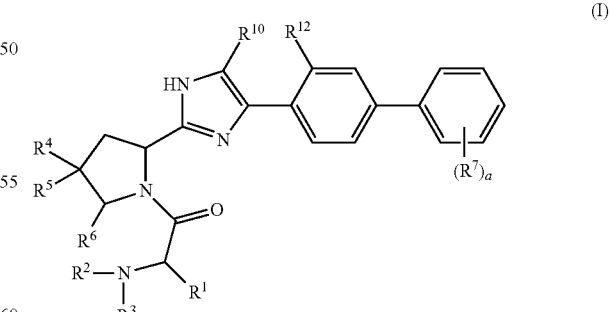

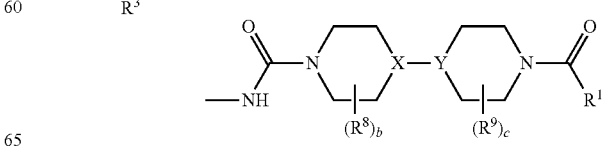

wherein
- $R^1$ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —$OR^a$, amino, —$SR^e$, heterocycle, or heteroaryl, $C_{1-6}$alkoxy is optionally substituted with —$OR^a$, and heterocycle is optionally substituted with —$OR^a$, amino, or —$C(O)OC_{1-6}$alkyl, or with one or two $C_{1-3}$alkyl;
- $R^2$ is selected from hydrogen and $C_{1-6}$alkyl;
- $R^3$ is selected from hydrogen, $C_{1-6}$alkyl, —$C(O)OC_{1-6}$alkyl, —$C(O)NR^mR^n$, —$C(O)C_{3-6}$cycloalkyl, and —$S(O)_2C_{1-3}$alkyl;
- $R^4$, $R^5$, and $R^6$ are each hydrogen;
- or $R^4$ is selected from $C_{1-6}$alkyl, —$NR^bR^c$, —$OR^d$, —CN, —$C(O)NR^aR^b$, and halo; and $R^5$ and $R^6$ are hydrogen;
- or $R^4$ and $R^5$ are independently $C_{1-6}$alkyl or halo and $R^6$ is hydrogen;
- or $R^4$ and $R^5$ taken together form —O—$(CH_2)_2$—O— and $R^6$ is hydrogen;
- or $R^4$ is hydrogen and $R^5$ and $R^6$ taken together form —$(CH_2)_n$—, wherein n is 1, 2, 3, or 4;
- or $R^4$ and $R^5$ are hydrogen, and $R^6$ is $C_{1-6}$alkyl,
- $R^7$ is selected from halo, $C_{1-3}$alkyl, and $C_{1-3}$alkoxy wherein $C_{1-3}$alkyl and $C_{1-3}$alkoxy are optionally substituted with one, two, three, four, or five halo;
- a is 0, 1, or 2;
- $R^8$ is $C_{1-3}$alkyl optionally substituted with —$OR^h$;
- b is 0, 1 or 2;
- or when b is 2, two $R^8$ can be joined to form —$(CH_2)_2$—;
- $R^9$ is $C_{1-3}$alkyl;
- c is 0, 1 or 2;
- $R^{10}$ is hydrogen, halo, or $C_{1-3}$alkyl substituted with one, two, or three halo, or with —$OR^h$;
- $R^{11}$ is selected from $C_{1-6}$alkyl, $C_{3-10}$cycloalkyl, $C_{1-6}$alkoxy, —$NR^fR^g$, heteroaryl, heterocycle, and —$CH_2$-heteroaryl;
- wherein:
  - $C_{1-6}$alkyl is optionally substituted with one or two substituents independently selected from —$OR^h$, —$NR^jR^k$, and phenyl;
  - $C_{1-6}$alkoxy is optionally substituted with —$OR^h$ or with phenyl;
  - any $C_{3-10}$cycloalkyl is optionally substituted with one or two substituents independently selected from $C_{1-3}$alkyl, —$CD_3$, halo, and —$OR^h$;
  - any heterocycle is optionally substituted with one, two, or three substituents independently selected from $C_{1-3}$alkyl, halo, —$C(O)OC_{1-3}$alkyl, and —$C(O)C_{1-6}$alkyl, wherein any —$C(O)C_{1-6}$alkyl is optionally substituted with —$NHC(O)OC_{1-3}$alkyl;
  - any heteroaryl is optionally substituted with one or two $C_{1-3}$alkyl;
- $R^{12}$ is hydrogen or $R^{10}$ and $R^{12}$ taken together form —CH=CH— or —$(CH_2)_2$—;
- $R^a$, $R^b$, $R^c$, $R^d$, $R^e$, $R^f$, $R^h$, $R^j$, $R^m$, and $R^n$ are each independently hydrogen or $C_{1-3}$alkyl;
- $R^g$ is selected from hydrogen, $C_{1-6}$alkyl, and $C_{3-6}$cycloalkyl;
- $R^k$ is selected from hydrogen, —$C(O)C_{1-3}$alkyl, —$C(O)OC_{1-3}$alkyl, —$C(O)ONR^bR^c$; and —$C(O)NR^bR^c$; and
- X is N and Y is CH or X is CH and Y is N;
- provided that when X is CH, b is 0 and when Y is CH, c is 0;
- or a pharmaceutically-acceptable salt or stereoisomer thereof.

2. The compound of claim 1 wherein the compound of formula (I) is a compound of formula (II):

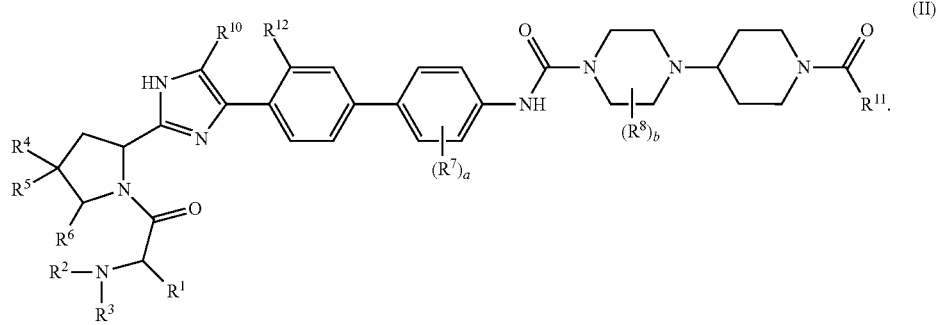

(II)

3. The compound of claim 1 wherein the compound of formula (I) is a compound of formula (III):

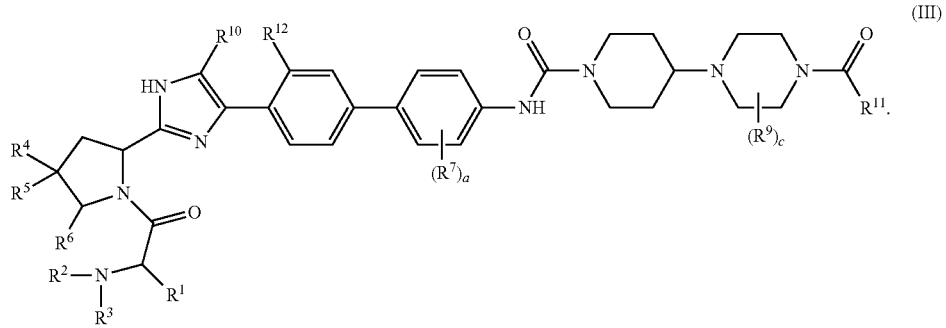

(III)

4. The compound of claim 1 wherein $R^1$ is selected from $C_{1-6}$alkyl optionally substituted with hydroxy or methoxy, and tetrahydropyran.

5. The compound of claim 1 wherein $R^4$ is methyl, methoxy, fluoro, or —C(O)NH$_2$ and $R^5$ and $R^6$ are hydrogen.

6. The compound of claim 1 wherein $R^{10}$ and $R^{12}$ taken together form —CH=CH—.

7. The compound of claim 1 wherein a is 1 or 2.

8. The compound of claim 1 wherein the compound is a compound of formula (IV):

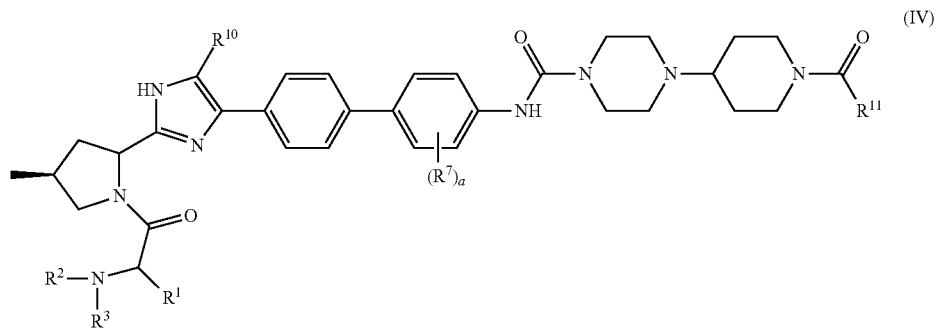

wherein:
- $R^1$ is selected from $C_{1-6}$alkyl optionally substituted with hydroxy or methoxy, tetrahydropyran and phenyl;
- $R^2$ is hydrogen;
- $R^3$ is —C(O)OC$_{1-6}$alkyl;
- $R^7$ is selected from fluoro, chloro, —CF$_3$, and —OCF$_3$;
- $R^{11}$ is selected from $C_{1-6}$alkyl, $C_{3-6}$cycloalkyl, and $C_{1-6}$alkoxy wherein $C_{1-6}$alkyl is optionally substituted with —OR$^h$ and $C_{3-6}$cycloalkyl is optionally substituted with one or two $C_{1-3}$alkyl;
- $R^{10}$ is hydrogen, chloro, or fluoro; and
- a is 1 or 2;

or a pharmaceutically-acceptable salt thereof.

9. The compound of claim 8 wherein $R^{11}$ is selected from tert-butyl, cyclopropyl, 2,2-dimethylcyclopropyl, cyclobutyl, 2,2-dimethylcyclobutyl, 3-hydroxy-2,2-dimethylpropyl, and tert-butoxy.

10. The compound of claim 1 wherein the compound is a compound of formula (V):

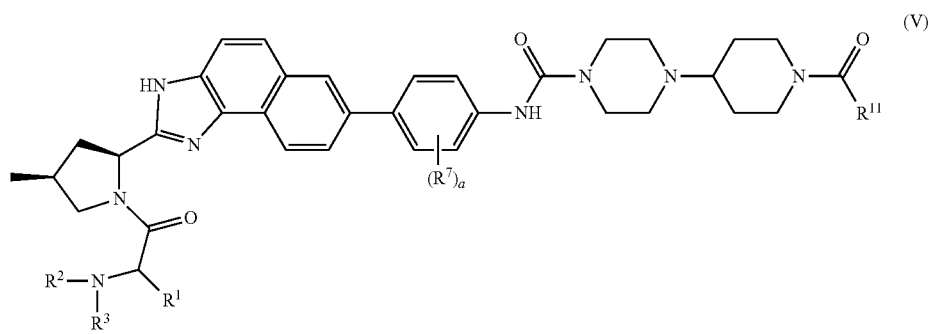

wherein:
- $R^1$ is selected from $C_{1-6}$alkyl optionally substituted with hydroxy or methoxy, tetrahydropyran and phenyl;
- $R^2$ is hydrogen;
- $R^3$ is —C(O)OC$_{1-6}$alkyl;
- $R^7$ is selected from fluoro, chloro, —CF$_3$, and —OCF$_3$;
- $R^{11}$ is selected from $C_{1-6}$alkyl, $C_{3-6}$cycloalkyl, and $C_{1-6}$alkoxy wherein $C_{1-6}$alkyl is optionally substituted with —OR$^h$ and $C_{3-6}$cycloalkyl is optionally substituted with one or two $C_{1-3}$alkyl; and
- a is 1 or 2;

or a pharmaceutically-acceptable salt thereof.

11. The compound of claim 10 wherein $R^{11}$ is selected from tert-butyl, cyclopropyl, 2,2-dimethylcyclopropyl, cyclobutyl, 2,2-dimethylcyclobutyl, 3-hydroxy-2,2-dimethylpropyl, and tert-butoxy.

12. The compound of claim 1 wherein the compound is selected from

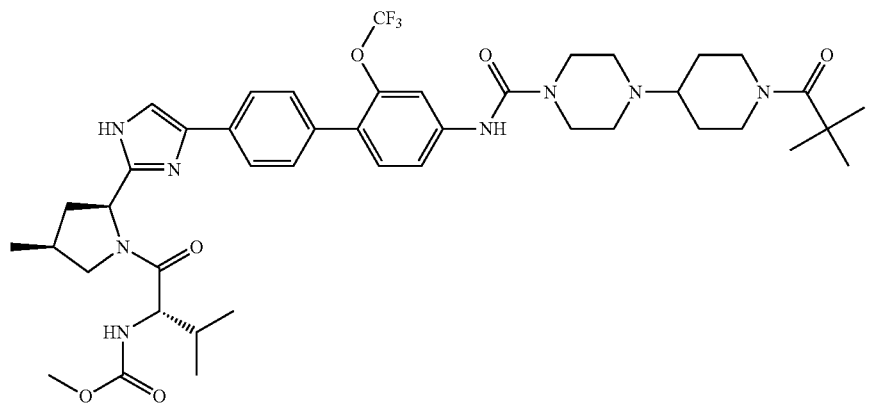
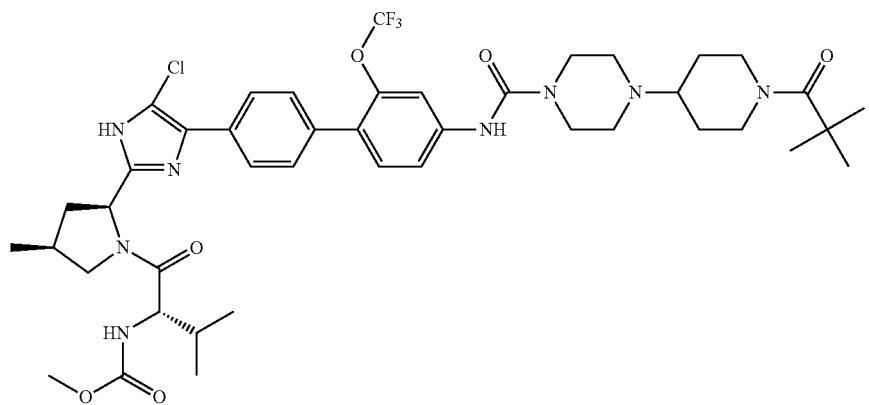
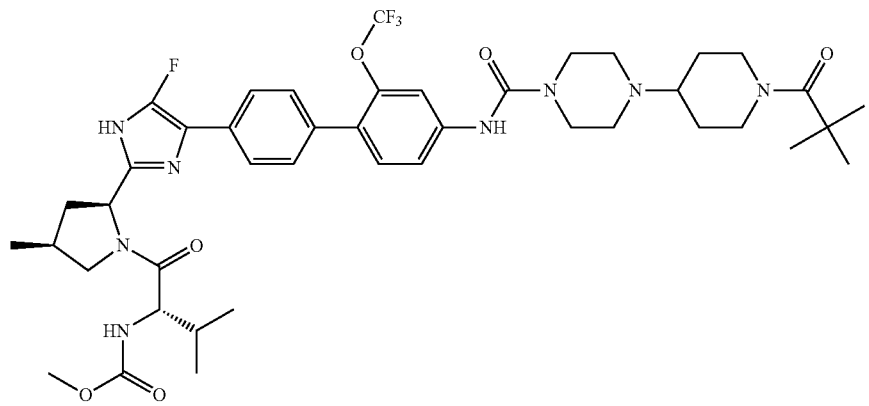
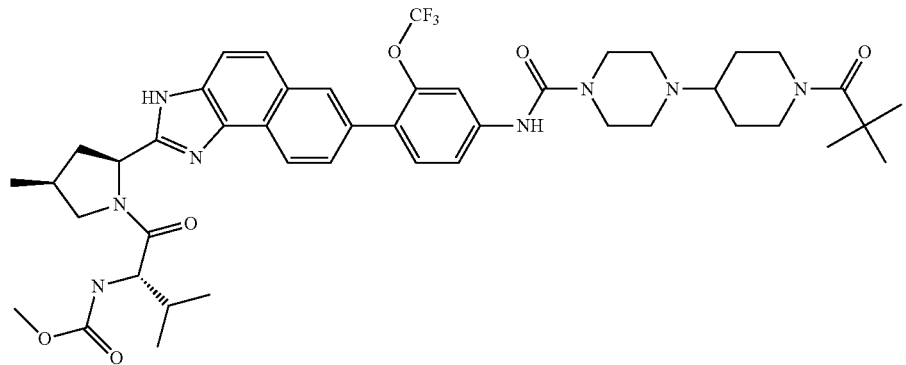

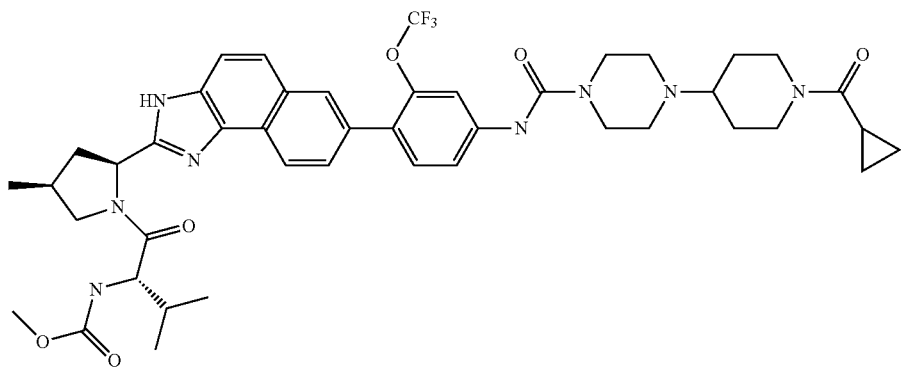
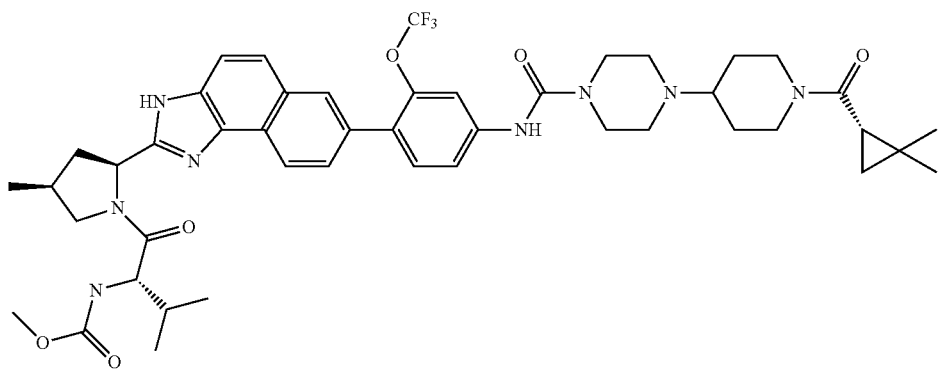
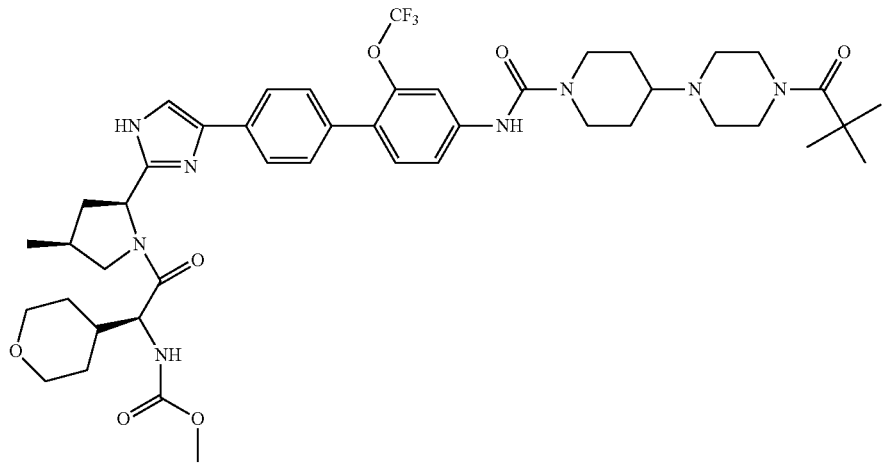
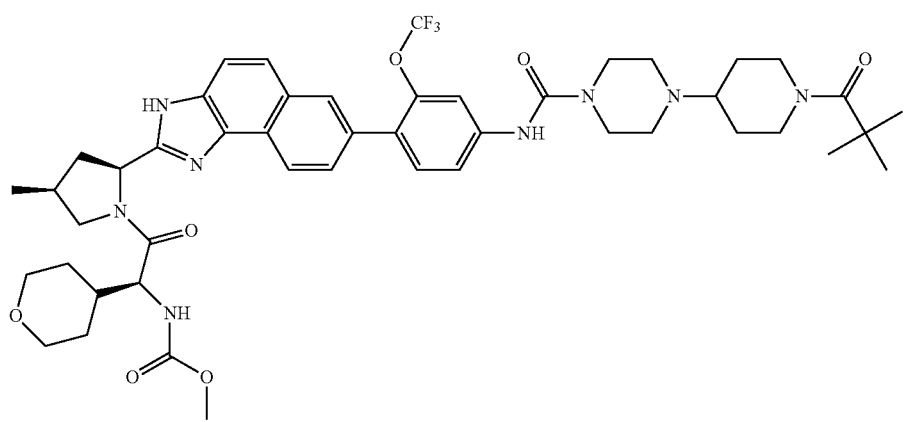

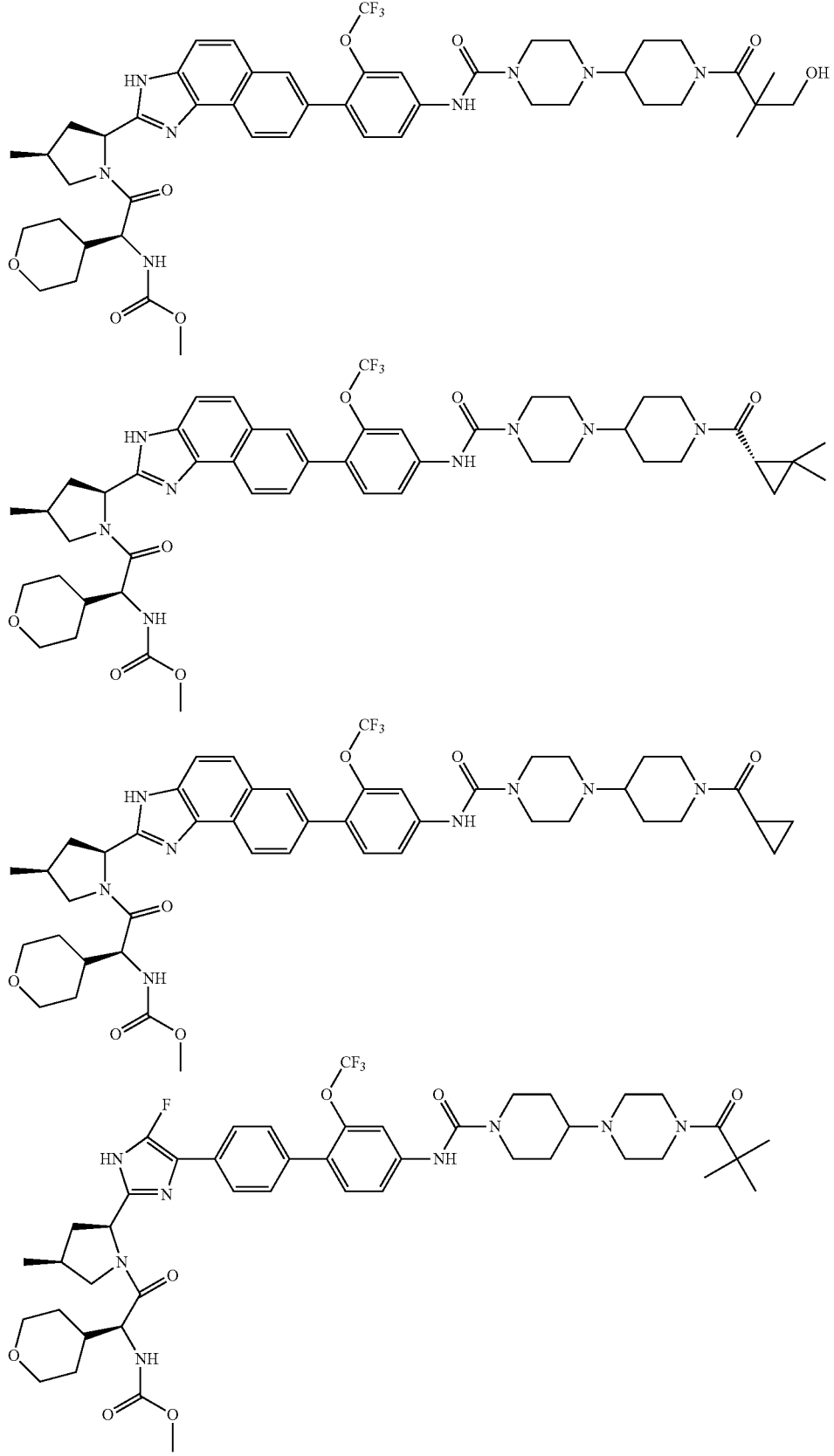
and pharmaceutically-acceptable salts thereof.

13. A pharmaceutical composition comprising a compound of claim 1 and a pharmaceutically-acceptable carrier.

14. The pharmaceutical composition of claim 13 further comprising one or more therapeutic agents useful for alleviating the symptoms of hepatitis C viral infections.

15. The pharmaceutical composition of claim 14 wherein the one or more therapeutic agents is selected from HCV NS3 protease inhibitors, and HCV NS5B nucleoside and non-nucleoside polymerase inhibitors.

16. A method of treating hepatitis C viral infection in a mammal, the method comprising administering to a mammal having hepatitis C viral infection a pharmaceutical compositions comprising a compound of claim 1 and a pharmaceutically acceptable carrier.

17. The method of claim 16 wherein the method further comprises administering one or more therapeutic agents useful for treating hepatitis C viral infections.

18. The method of claim 17 wherein the one or more therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin and related nucleoside analogs.

19. A method of inhibiting replication of the hepatitis C virus in a mammal, the method comprising administering to the mammal a pharmaceutical composition comprising a compound of claim 1 and a pharmaceutically-acceptable carrier.

20. The method of claim 19 wherein the method further comprises administering to the mammal one or more therapeutic agents useful for inhibiting replication of the hepatitis C virus in a mammal.

21. The method of claim 20 wherein the one or more therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin and related nucleoside analogs.

\* \* \* \* \*